US010046047B2

(12) United States Patent
Schreiber et al.

(10) Patent No.: US 10,046,047 B2
(45) Date of Patent: Aug. 14, 2018

(54) VECTOR CO-EXPRESSING VACCINE AND COSTIMULATORY MOLECULES

(71) Applicant: HEAT BIOLOGICS, INC., Durham, NC (US)

(72) Inventors: Taylor Schreiber, Durham, NC (US); George Fromm, Durham, NC (US)

(73) Assignee: Heat Biologics, Inc., Durham, NC (US)

( * ) Notice: Subject to any disclaimer, the term of this patent is extended or adjusted under 35 U.S.C. 154(b) by 237 days.

(21) Appl. No.: 15/016,375

(22) Filed: Feb. 5, 2016

(65) Prior Publication Data

US 2016/0250322 A1    Sep. 1, 2016

Related U.S. Application Data

(60) Provisional application No. 62/174,942, filed on Jun. 12, 2015, provisional application No. 62/113,153, filed on Feb. 6, 2015.

(51) Int. Cl.
| | |
|---|---|
| C07K 14/705 | (2006.01) |
| C07K 16/28 | (2006.01) |
| C12N 15/62 | (2006.01) |
| C12N 15/63 | (2006.01) |
| C12N 15/86 | (2006.01) |
| A61K 39/39 | (2006.01) |
| A61K 39/42 | (2006.01) |
| A61K 48/00 | (2006.01) |
| A61K 39/00 | (2006.01) |
| A61K 39/395 | (2006.01) |
| C07K 14/47 | (2006.01) |

(52) U.S. Cl.
CPC .......... *A61K 39/39* (2013.01); *A61K 39/0011* (2013.01); *A61K 39/3955* (2013.01); *A61K 39/42* (2013.01); *A61K 48/00* (2013.01); *C07K 14/4702* (2013.01); *C07K 14/70532* (2013.01); *C07K 14/70575* (2013.01); *C07K 16/2878* (2013.01); *C12N 15/86* (2013.01); *A61K 2039/505* (2013.01); *A61K 2039/525* (2013.01); *A61K 2039/5258* (2013.01); *A61K 2039/53* (2013.01); *A61K 2039/55516* (2013.01); *A61K 2039/57* (2013.01); *C07K 2317/75* (2013.01); *C07K 2319/30* (2013.01); *C07K 2319/40* (2013.01); *C07K 2319/75* (2013.01); *Y02A 50/412* (2018.01)

(58) Field of Classification Search
None
See application file for complete search history.

(56) References Cited

U.S. PATENT DOCUMENTS

| | | | |
|---|---|---|---|
| 4,690,915 A | 9/1987 | Rosenberg | |
| 5,188,964 A | 2/1993 | McGuire et al. | |
| 5,217,891 A | 6/1993 | Brake et al. | |
| 5,232,833 A | 8/1993 | Sanders et al. | |
| 5,348,945 A | 9/1994 | Berberian et al. | |
| 5,719,044 A | 2/1998 | Shoseyov et al. | |
| 5,747,332 A | 5/1998 | Wallen et al. | |
| 5,750,119 A | 5/1998 | Srivastava | |
| 5,830,464 A | 11/1998 | Srivastava | |
| 5,837,251 A | 11/1998 | Srivastava | |
| 5,948,646 A | 9/1999 | Srivastava | |
| 5,961,979 A | 10/1999 | Srivastava | |
| 5,985,270 A | 11/1999 | Srivastava | |
| 5,997,873 A | 12/1999 | Srivastava | |
| 6,007,821 A | 12/1999 | Srivastava et al. | |
| 6,017,540 A | 1/2000 | Srivastava et al. | |
| 6,017,544 A | 1/2000 | Srivastava | |
| 6,030,618 A | 2/2000 | Srivastava | |
| 6,048,530 A | 4/2000 | Srivastava | |
| 6,130,087 A | 10/2000 | Srivastava et al. | |
| 6,136,315 A | 10/2000 | Srivastava | |
| 6,156,302 A | 12/2000 | Srivastava | |
| 6,162,436 A | 12/2000 | Srivastava | |
| 6,168,793 B1 | 1/2001 | Srivastava | |
| 6,322,790 B1 | 11/2001 | Srivastava | |
| 6,328,957 B1 | 12/2001 | Colston et al. | |
| 6,331,299 B1 | 12/2001 | Rothman et al. | |
| 6,383,493 B1 | 5/2002 | Srivastava et al. | |
| 6,383,494 B1 | 5/2002 | Srivastava et al. | |
| 6,387,374 B1 | 5/2002 | Srivastava et al. | |
| 6,399,070 B1 | 6/2002 | Srivastava et al. | |
| 6,403,095 B1 | 6/2002 | Srivastava et al. | |
| 6,406,700 B1 | 6/2002 | Srivastava | |
| 6,410,026 B1 | 6/2002 | Srivastava | |
| 6,410,027 B1 | 6/2002 | Srivastava | |

(Continued)

FOREIGN PATENT DOCUMENTS

| | | |
|---|---|---|
| CA | 2158655 A1 | 9/1994 |
| DE | 196 02 985 A1 | 7/1997 |

(Continued)

OTHER PUBLICATIONS

Tosti et al. (2009) Expert Rev Vaccines 8 (11): 1513-1526.*
Bloch et al. (2013) Neuro-Oncology. 16: 274-279.*
Moran et al. (2013) Current Opinion in Immunology, 25: 230-237.*
Schreiber et al. (2012) J Immunol. 189(7): 3311-3318.*
Curti et al. (2013) Cancer Res. 73(24): 7189-7198.*
Liu et al. Cancer Res. 2005; 65:9126-9131.*
Anderson et al., Lag-3, Tim-3, and TIGIT: Co-inhibitory Receptors with Specialized Functions in Immune Regulation, Immunity, 2016 vol. 44, pp. 989-1004.
Callahan et al., "Targeting T Cell Co-receptors for Cancer Therapy", Immunity, 2016, vol. 44, pp. 1069-1078.

(Continued)

*Primary Examiner* — Ilia I Ouspenski
(74) *Attorney, Agent, or Firm* — Morgan, Lewis & Bockius LLP

(57) ABSTRACT

Compositions and methods for co-expressing a secretable vaccine protein (such as gp96-Ig) and T-cell co-stimulatory molecules from a single vector, among others, are provided herein. Materials and methods for using gp96-Ig vaccination and T-cell co-stimulation to treat a clinical condition (e.g., cancer) in a subject also are provided.

13 Claims, 31 Drawing Sheets

(56) References Cited

U.S. PATENT DOCUMENTS

| | | |
|---|---|---|
| 6,410,028 B1 | 6/2002 | Srivastava |
| 6,436,404 B1 | 8/2002 | Srivastava et al. |
| 6,447,780 B1 | 9/2002 | Srivastava et al. |
| 6,447,781 B1 | 9/2002 | Srivastava |
| 6,451,316 B1 | 9/2002 | Srivastava |
| 6,455,048 B1 | 9/2002 | Srivastava et al. |
| 6,455,503 B1 | 9/2002 | Srivastava |
| 6,461,615 B1 | 10/2002 | Srivastava |
| 6,468,540 B1 | 10/2002 | Srivastava |
| 6,475,490 B1 | 11/2002 | Srivastava et al. |
| 6,605,464 B1 | 8/2003 | Rothman et al. |
| 6,610,659 B1 | 8/2003 | Pramod |
| 6,641,812 B2 | 11/2003 | Rothman et al. |
| 6,656,679 B2 | 12/2003 | Rothman et al. |
| 6,663,868 B1 | 12/2003 | Rothman et al. |
| 6,673,348 B2 | 1/2004 | Rothman et al. |
| 6,719,974 B1 | 4/2004 | Rothman et al. |
| 6,761,892 B1 | 7/2004 | Rothman et al. |
| 6,797,480 B1 | 9/2004 | Srivastava |
| 6,984,389 B2* | 1/2006 | Li ............... A61K 31/496 424/277.1 |
| 7,132,109 B1 | 11/2006 | Srivastava |
| 8,475,785 B2 | 7/2013 | Podack et al. |
| 8,685,384 B2 | 4/2014 | Podack et al. |
| 8,968,720 B2 | 3/2015 | Podack et al. |
| 9,238,064 B2 | 1/2016 | Podack et al. |
| 2003/0170756 A1 | 9/2003 | Berd |
| 2005/0019752 A1 | 1/2005 | Franchini et al. |
| 2005/0221395 A1* | 10/2005 | Zabrecky ............ A61K 31/19 435/7.9 |
| 2007/0141666 A1 | 6/2007 | Dupraz et al. |
| 2008/0019972 A1 | 1/2008 | Andrieu |
| 2008/0089901 A1 | 4/2008 | Hanke et al. |
| 2009/0162404 A1 | 6/2009 | Podack |
| 2010/0136032 A1* | 6/2010 | Weinberg ............ A61K 38/191 424/178.1 |
| 2010/0247562 A1* | 9/2010 | Gong ............... C07K 16/18 424/193.1 |
| 2011/0059041 A1* | 3/2011 | Truneh ............. A61K 39/245 424/85.2 |
| 2011/0086057 A1* | 4/2011 | Soto-Jara ........... C07K 14/52 424/185.1 |
| 2011/0123552 A1* | 5/2011 | Bakker ............. A61K 31/00 424/173.1 |
| 2011/0171211 A1 | 7/2011 | Podack et al. |
| 2011/0250229 A1 | 10/2011 | Podack et al. |
| 2012/0034242 A1* | 2/2012 | Jooss ............... A61K 38/193 424/173.1 |
| 2012/0093825 A1* | 4/2012 | Renauld ........... C07K 14/70575 424/140.1 |
| 2012/0100173 A1* | 4/2012 | Leclair ............. A61K 39/0011 424/193.1 |
| 2012/0258046 A1 | 10/2012 | Mutzke |
| 2013/0045202 A1 | 2/2013 | Irving et al. |
| 2013/0052160 A1 | 2/2013 | Zitvogel et al. |
| 2013/0121960 A1* | 5/2013 | Sadelain ........... A61K 39/0011 424/85.2 |
| 2013/0195800 A1* | 8/2013 | Roeth .............. C07K 14/5434 424/93.2 |
| 2013/0209511 A1* | 8/2013 | Mebatsion ......... A61K 39/008 424/209.1 |
| 2014/0037682 A1 | 2/2014 | Podak et al. |
| 2014/0107391 A1* | 4/2014 | Srivastava ......... A61K 31/7048 600/1 |
| 2014/0134650 A1 | 5/2014 | Hawtin et al. |
| 2014/0286991 A1 | 9/2014 | Podack et al. |
| 2014/0335050 A1 | 11/2014 | Haggerty et al. |
| 2014/0335086 A1 | 11/2014 | Podack et al. |
| 2015/0191525 A1* | 7/2015 | Epstein ........... C07K 14/70578 424/134.1 |
| 2015/0368350 A1* | 12/2015 | Tykocinski ........ A61K 39/3955 424/134.1 |
| 2016/0024176 A1* | 1/2016 | Damschroder .. C07K 14/70575 424/134.1 |
| 2016/0256527 A1* | 9/2016 | Gurney ............... C07K 14/525 |
| 2016/0289645 A1* | 10/2016 | Tufaro ............... A61K 35/761 |
| 2017/0182156 A1* | 6/2017 | Khleif ................ A61K 39/39 |

FOREIGN PATENT DOCUMENTS

| | | |
|---|---|---|
| GB | 2 251 186 A | 7/1992 |
| WO | 198912455 A1 | 12/1989 |
| WO | 199002564 A1 | 3/1990 |
| WO | 199102077 A1 | 2/1991 |
| WO | 199115572 A1 | 10/1991 |
| WO | 199201717 A1 | 2/1992 |
| WO | 199208484 A1 | 5/1992 |
| WO | 199208488 A1 | 5/1992 |
| WO | 199403599 A1 | 2/1993 |
| WO | 199314118 A1 | 7/1993 |
| WO | 199317712 A1 | 9/1993 |
| WO | 199318146 A2 | 9/1993 |
| WO | 199318147 A1 | 9/1993 |
| WO | 199321529 A1 | 10/1993 |
| WO | 199403208 A1 | 2/1994 |
| WO | 199404676 A1 | 3/1994 |
| WO | 199411513 A1 | 5/1994 |
| WO | 199504824 A1 | 2/1995 |
| WO | 199506725 A1 | 3/1995 |
| WO | 199524923 A2 | 9/1995 |
| WO | 199601611 A1 | 1/1996 |
| WO | 199602143 A1 | 2/1996 |
| WO | 199610411 A1 | 4/1996 |
| WO | 199610419 A2 | 4/1996 |
| WO | 199631613 A1 | 10/1996 |
| WO | 199706685 A1 | 2/1997 |
| WO | 199706821 A1 | 2/1997 |
| WO | 199706828 A1 | 2/1997 |
| WO | 199710000 A1 | 3/1997 |
| WO | 199710001 A1 | 3/1997 |
| WO | 199710002 A1 | 3/1997 |
| WO | 199726910 A2 | 7/1997 |
| WO | 199735619 A1 | 10/1997 |
| WO | 199823735 A1 | 6/1998 |
| WO | 199942121 A1 | 8/1999 |
| WO | 2003005964 A2 | 1/2003 |
| WO | 2004032865 A2 | 4/2004 |
| WO | 2005030136 A2 | 4/2005 |
| WO | 2005092373 A1 | 10/2005 |
| WO | 2009114085 A2 | 9/2009 |
| WO | 2009114110 A1 | 9/2009 |
| WO | 2009117116 A2 | 9/2009 |
| WO | 2010060026 A1 | 5/2010 |
| WO | 2011146828 A2 | 11/2011 |
| WO | 2012116142 A2 | 8/2012 |
| WO | 2012166617 A2 | 12/2012 |
| WO | 2014140884 A2 | 9/2014 |
| WO | 2014140904 A2 | 9/2014 |

OTHER PUBLICATIONS

Curran et al., Editorial: Advances in Combination Tumor Immunotherapy, Frontiers in Oncology, 2015, vol. 5, No. 198, pp. 1-2.
de Visser et al., "Paradoxical Roles of the Immune System during Cancer Development", Nature, 2006, vol. 6, pp. 24-37.
Guo et al., PD-1 Blockade and OX40 Triggering Synergistically Protects against Tumor Growth in a Murine Model of Ovarian Cancer, PLOS ONE, vol. 9, No. 2, pp. 1-10.
International Search Report and Written Opinion PCT/US2016/016682, dated Jun. 2, 2016, 8 pages.
Khalil et al., "The Future of Cancer Treatment: Immunomodulation, Cars and Combination Immunotherapy", Nature Reviews Clinical Oncology, 2016, pp. 1-18.
Ledford, H., "The Perfect Blend", Nature, 2016, vol. 532, pp. 162-164.
Linch et al., "OX40 Agonists and Combination Immunotherapy: Putting the Pedal to the Metal", Frontiers in Oncology, 2015, vol. 5, No. 34, pp. 1-14.

(56) References Cited

OTHER PUBLICATIONS

Mahoney et al., Combination Cancer Immunotherapy and New Immunomodulatory Targets, Nature Reviews Drug Discovery, 2015, vol. 14, pp. 561-584.

Mellman et al., "Cancer immunotherapy comes of age", Nature, 2010, vol. 480, pp. 480-489.

Oizumi, et al., "Molecular and Cellular Requirements for Enhanced Antigen Cross-Presentation to CD8 Cytotoxic T Lymphocytes", The Journal of Immunology, 2007, vol. 179, pp. 2310-2317.

Oizumi, et al., "Surmounting Tumor-induced Immune Suppression by Frequent Vaccination or Immunization in the Absence of B Cells", J Immunother, 2008, vol. 31, No. 4, pp. 394-401.

Pardall, "The Blockade of Immune Checkpoints in Cancer Immunotherapy" Nature Reviews Cancer, 2012, vol. 12, pp. 252-264.

Raez et al "CD8 T Cell Response in a Phase I Study of Therapeutic Vaccination of Advanced NSCLC with Allogeneic Tumor Cells Secreting Endoplasmic Reticulum-Chaperone Gp96-Ig-Peptide Complexes" Advances in Lung Cancer, 2013, vol. 2, No. 1, pp. 9-18.

Schildberg et al., "Coinhibitory Pathways in the B7-CD28 Ligand-Receptor Family", Immunity, 2016 vol. 44, pp. 955-972.

Schreiber et al,. "Tumor-Induced Suppression of CTL Expansion and Subjugation by gp96-Ig Vaccination", Cancer Res, 2009, vol. 69 No. 5, pp. 2026-2033.

Schreiber et al., "Tumor Immunogenicity and Responsiveness to Cancer Vaccine Therapy: The State of the Art", Seminars in Immunology, 2010, vol. 22 pp. 105-112.

Strbo et al., "Cell-secreted Gp96-Ig-Peptide Complexes Induce Lamina Propria and Intraepithelial CD8+ Cytotoxic T Lymphocytes in the Intestinal Mucosa", Nature, 2010, vol. 3, No. 2, pp. 182-192.

Ward-Kavanagh et al., "The TNF Receptor Superfamily in Co-stimulating and Co-inhibitory Responses", 2016, Immunity, vol. 44, pp. 1005-1019.

Yamazaki et al. "Cutting Edge: Tumor Secreted Heat Shock-Fusion Protein Elicits CD8 Cells for Rejection", J Immunol, 1999, vol. 163, pp. 5178-5182.

\* cited by examiner

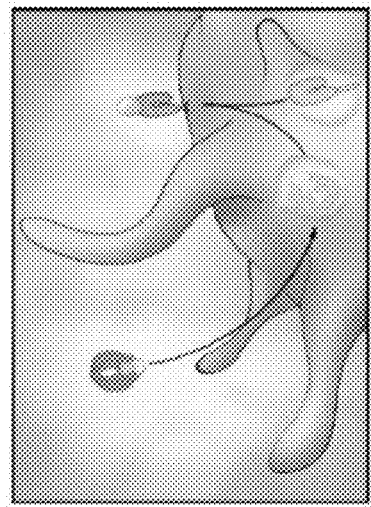
FIG. 4A
Vaccine cells secrete gp96-Ig together with cell-derived shared tumor antigens
FIG. 4B
Gp96-Ig/antigen complexes are taken up by APCs and antigens are transferred to MHC I
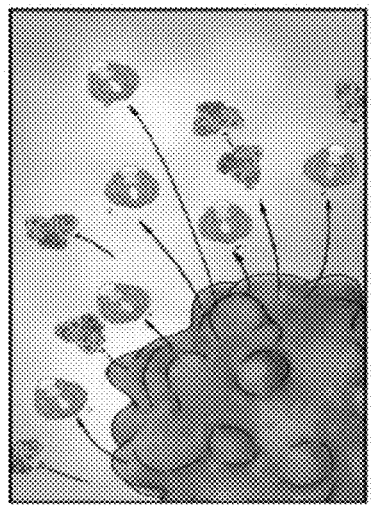
FIG. 4C
Antigen cross-presentation leads to exclusive activation of CD8+ T cells
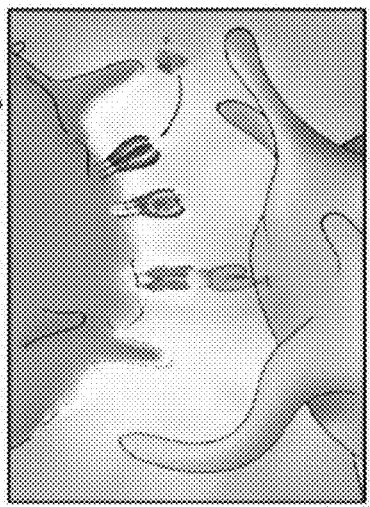
FIG. 4D
Activated CD8+ T cells can recognize shared tumor antigen on distant tumors and destroy them

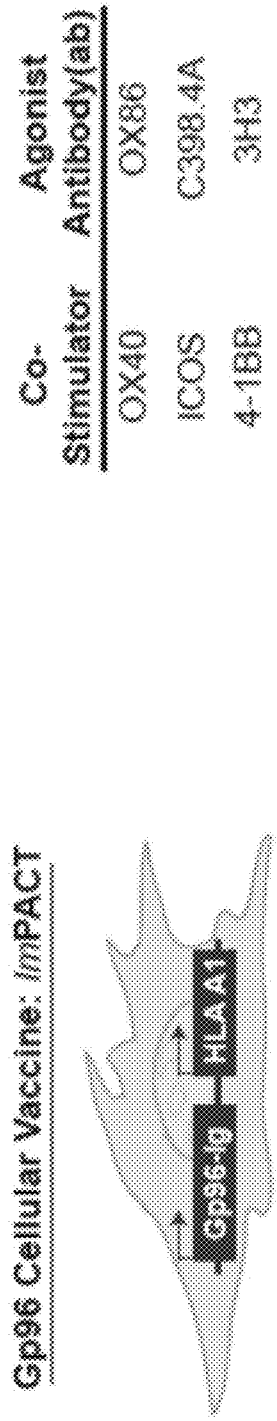

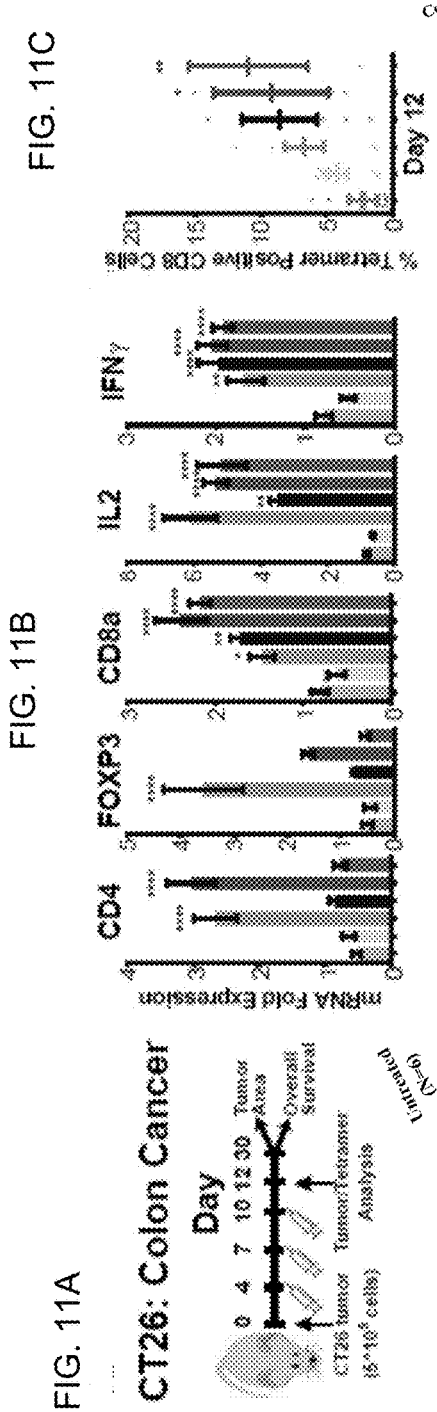
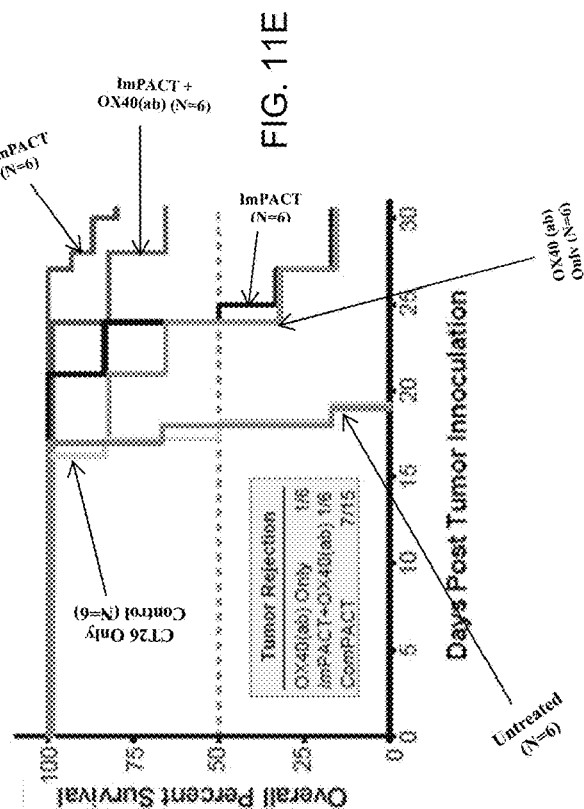
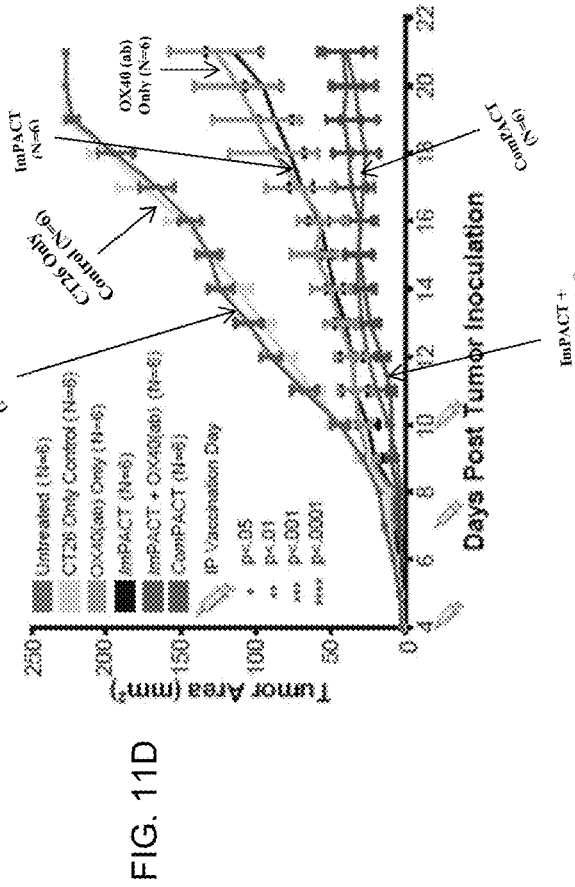
FIG. 11A, FIG. 11B, FIG. 11C, FIG. 11D, FIG. 11E

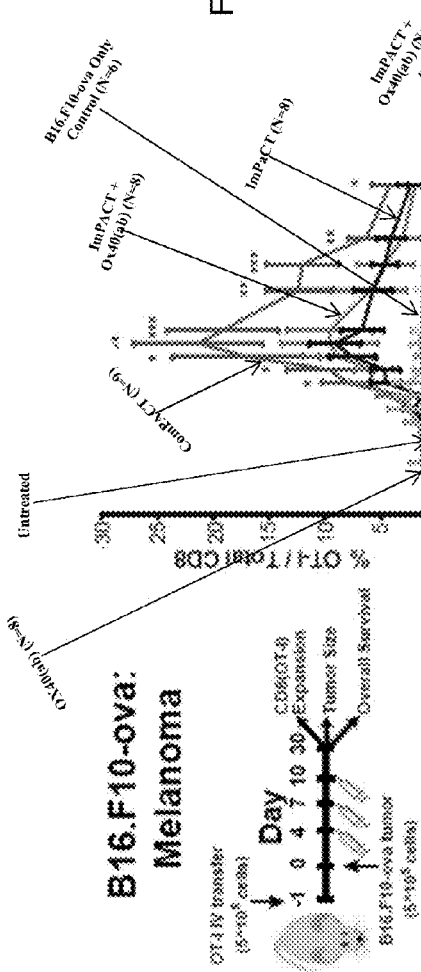
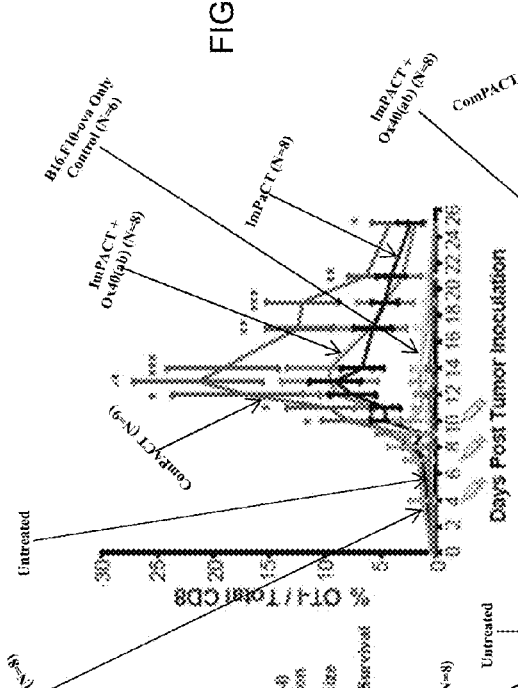
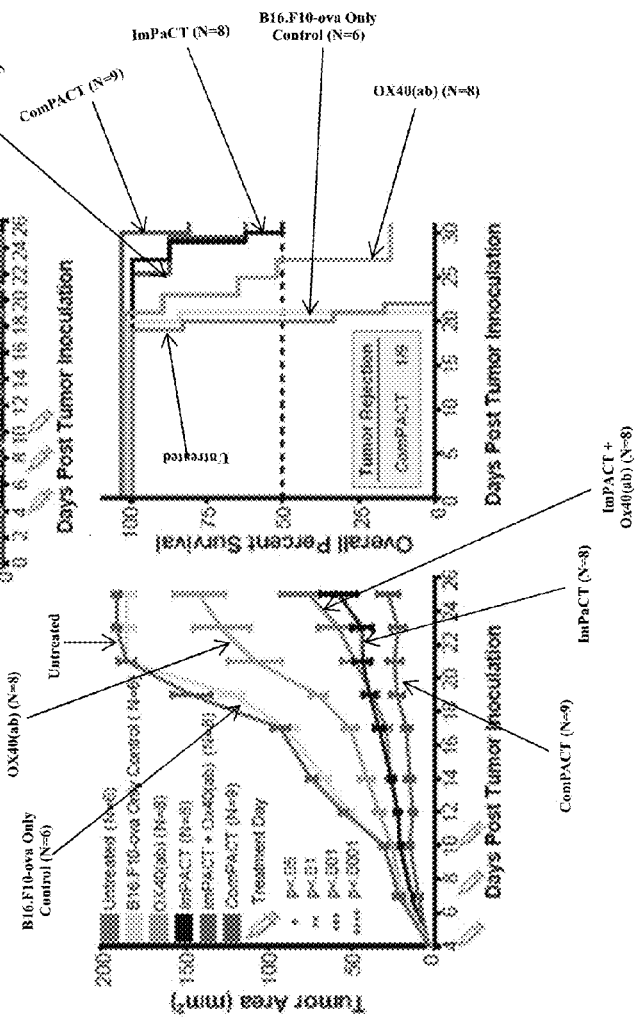
FIG. 12A
FIG. 12B
FIG. 12C
FIG. 12D

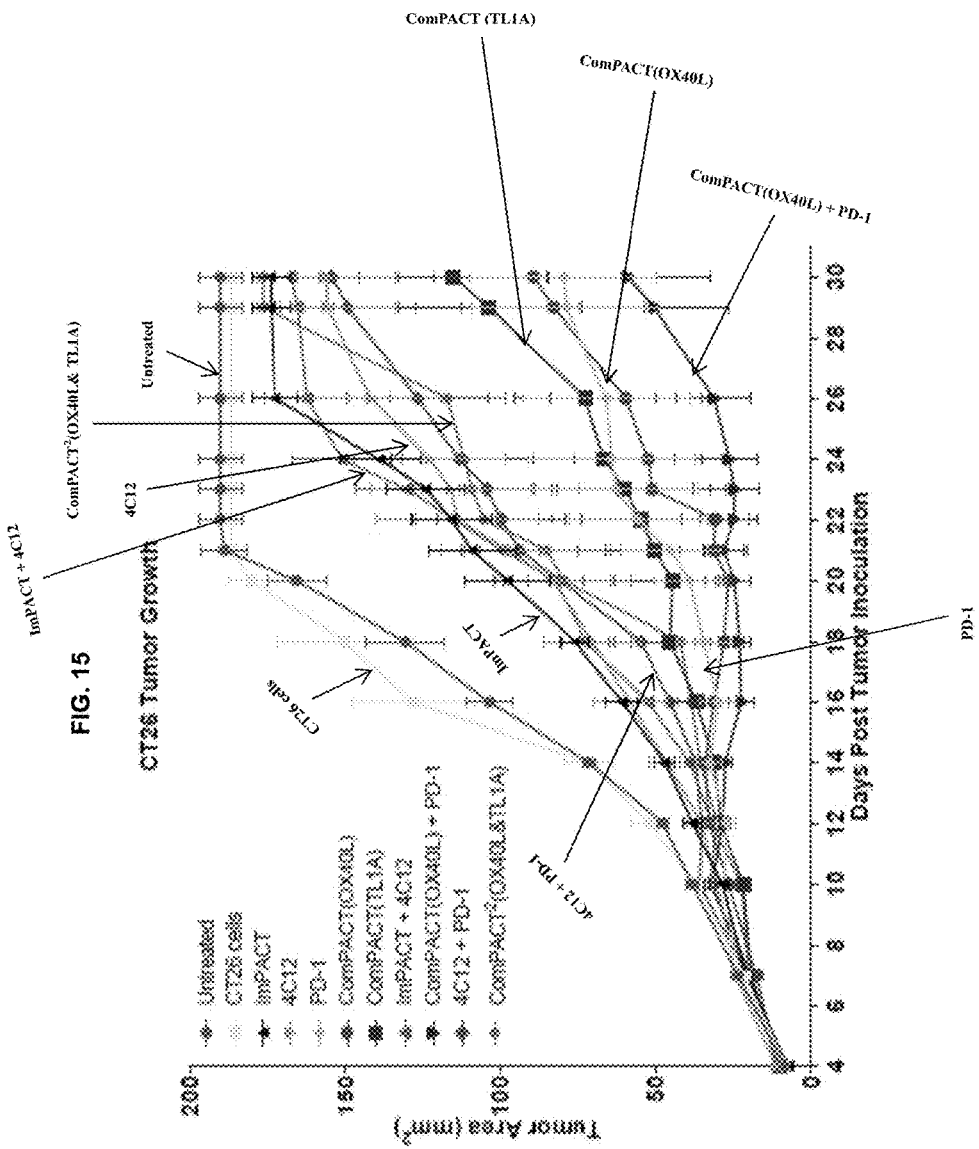

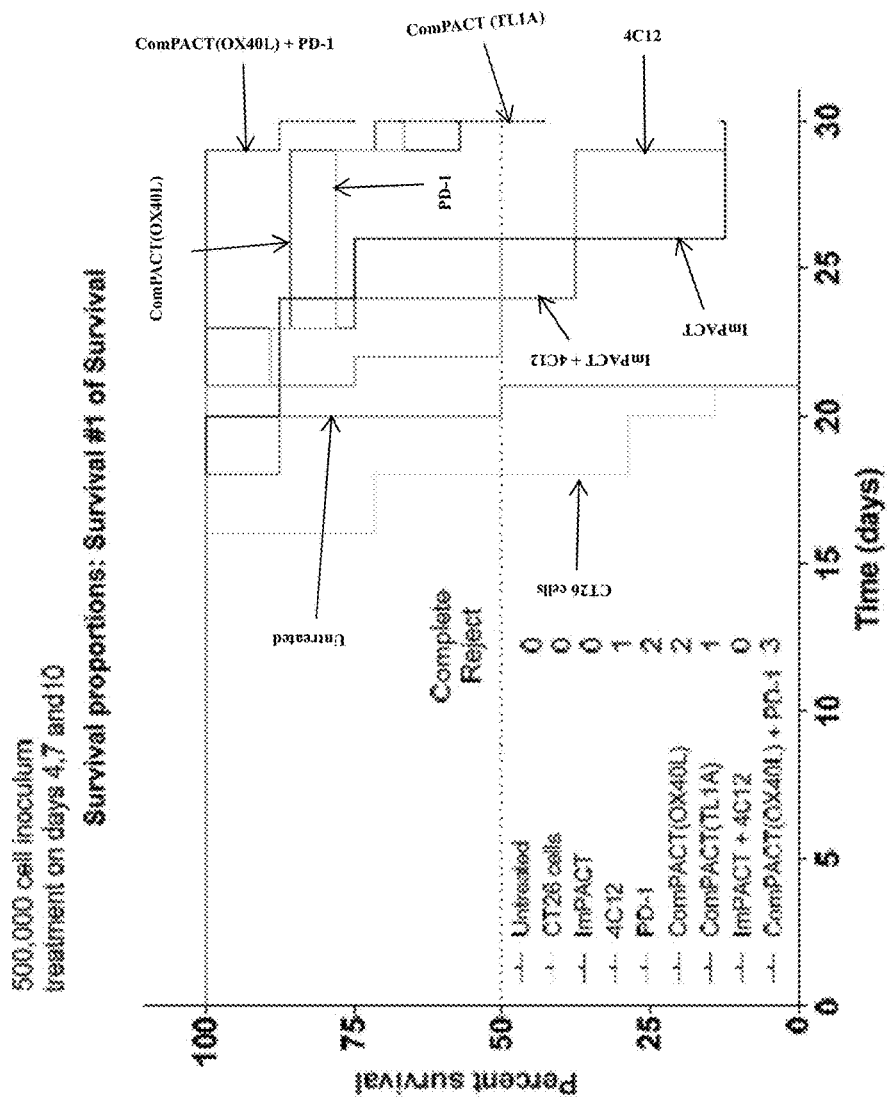

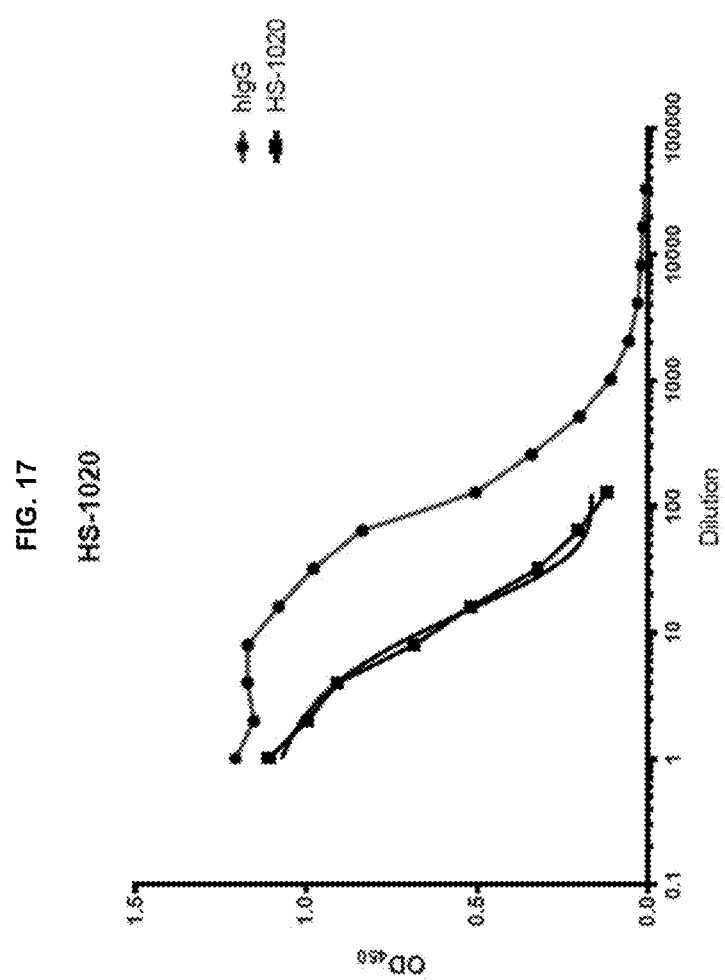

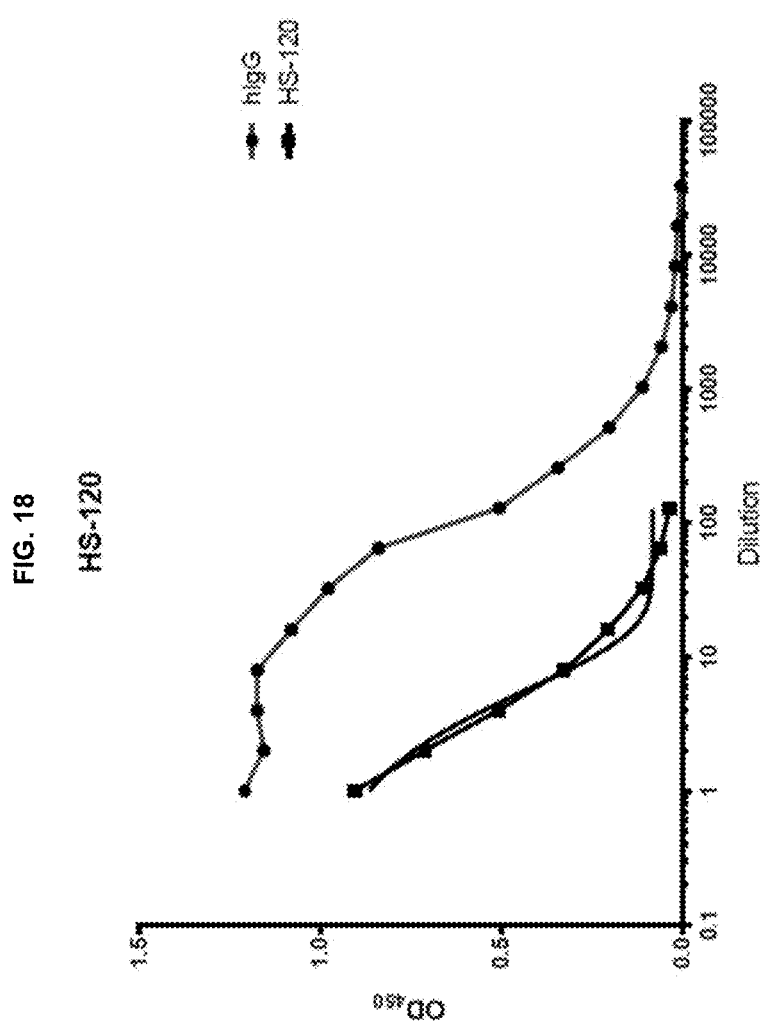

VECTOR CO-EXPRESSING VACCINE AND COSTIMULATORY MOLECULES

RELATED APPLICATIONS

The present application claims priority to U.S. Provisional Patent Application Nos. 62/113,153, filed Feb. 6, 2015, and 62/174,942, filed Jun. 12, 2015, the entire contents of all of which are hereby incorporated by reference.

TECHNICAL FIELD

This document relates, inter alia, to materials and methods for using vaccination and T-cell co-stimulation to treat a clinical condition in a subject, including materials and methods for co-expressing a vaccine (e.g. gp96-Ig) and T-cell co-stimulatory molecules from a single vector.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename HTB-021-SequenceListing.txt; date recorded: Feb. 4, 2016; file size: 73 KB).

BACKGROUND

Cancer is a disease that arises from a prolonged period of genetic instability that extends the lifespan of a normal cell. The triggering event that marks the beginning of this period is variable between cell types, but commonly is the acquisition of a mutation in a tumor suppressor gene such as p53 or Rb, a mutation in a proto-oncogene such as KRAS or myc, or infection of a cell with an oncogenic virus such as HPV16 or EBV. Whatever the origin, cells that acquire mutations in genes that enable them to escape normal growth controls or cell death pathways become more likely to acquire additional mutations. Once a cell has acquired "enough" mutations, typically thought to be at least six, it no longer is responsive to intrinsic or extrinsic signals that would restrain its growth or trigger apoptosis.

Because tumors arise from host cells, the body's immune system is initially tolerant to those cells. The acquisition of tumorigenic mutations may or may not lead to production of a mutated protein containing an epitope that is sufficiently non-self to become immunogenic. If a cell acquires an immunogenic mutation, it can be sought out and destroyed by the host immune system, a process known as immuno-surveillance (Smyth et al., *Adv Immunol* 2006, 90:1-50). Murine studies have provided support for the immune surveillance hypothesis (Dunn et al., *Nat Immunol* 2002, 3:991-998; Shankaran et al., *Nature* 2001, 410:1107-1111; and Dunn et al., *Annu Rev Immunol* 2004, 22:329-360), and also suggested that innate in addition to so-called adaptive immune responses may facilitate rejection of immunogenic tumors (Unni et al., *Proc Natl Acad Sci USA* 2008, 105:1686-1691; Taieb et al., *Nat Med* 2006, 12:214-219; and Raulet and Guerra, *Nat Rev Immunol* 2009, 9:568-580). Innate responses can be evoked through induced expression of NK activating signals such as NKG2D ligand expression or following DNA damage incurred as a result of mutagenic or viral processes. Some cells that acquire immunogenic mutations also gain the capacity to engage normal immune regulatory systems that dampen anti-self immune responses (Rabinovich et al., *Annu Rev Immunol* 2007, 25:267-296). The pathways driving the activation of host regulatory mechanisms are poorly understood. Still other cells may gain a number of oncogenic mutations without ever producing an immunogenic peptide that leads to activation of the host immune system. Therefore, tumor cells that produce an immunogenic peptide during their transformation must continuously evade anti-tumor immune responses in order to survive, whereas tumors that become transformed without activating the immune system may not rely on such immune regulatory mechanisms for survival.

SUMMARY

It is possible that combination therapies including combinations or subcombinations of one or more checkpoint inhibitors, one or more vaccines, and one or more T cell costimulatory molecules may expand the base of cancer patients that can benefit from immunotherapy. Vaccines may contribute to this response by increasing both the frequency of tumor-antigen specific CD8+ T cells and also the number of tumor antigens recognized by those CD8+ T cells. T cell costimulatory molecules may enhance the response by further increasing the frequency and/or enhancing the activation of tumor antigen-specific T cells, and also by increasing the expression of tumor-killing effector molecules by CD8+ T cells. When used in combination with checkpoint inhibitors, it may be possible to generate a broad range of highly activated CD8+ T cells that will be able to infiltrate tumors and will not be inhibited by various checkpoint pathways once infiltration has occurred. An impediment to the success of combination therapies, however, is that they traditionally require administration of at least three different drug products (a vaccine, a T cell costimulatory, and a checkpoint inhibitor), each of which has a significant cost and, in some cases, toxicity.

This document is based, at least in part, on the discovery that a combination of a vaccination, e.g. gp96-Ig vaccination, and T cell costimulation with one or more agonists of OX40, ICOS, 4-1BB, TNFRSF25, CD40, CD27, and/or GITR, among others, provides a synergistic anti-tumor benefit. Pre-clinical models have evaluated independent compositions of 96-Ig vaccines combined with agonistic antibodies targeting OX40, ICOS, 4-1BB, and TNFRSF25, and demonstrated variable effects on mechanistic and anti-tumor complementarity. The materials and methods described herein are advantageous in that, inter alia, they provide a single composition that can achieve both vaccination with, for example, gp96-Ig, and T cell costimulation without the need for independent products. These materials and methods achieve this goal by creating a single vaccine protein (e.g., gp96-Ig) expression vector that has been genetically modified to simultaneously express an costimulatory molecule, including without limitation, fusion proteins such as ICOSL-Ig, 4-1BBL-Ig, TL1A-Ig, OX40L-Ig, CD40L-Ig, CD70-Ig, or GITRL-Ig to provide T cell costimulation. The vectors, and methods for their use, can provide a costimulatory benefit without the need for an additional antibody therapy to enhance the activation of antigen-specific CD8+ T cells. Thus, combination immuno-therapy can be achieved by vector re-engineering to obviate the need for vaccine/antibody/fusion protein regimens, which may reduce both the cost of therapy and the risk of systemic toxicity.

In one aspect, this document features an expression vector containing a first nucleotide sequence that encodes a secretable vaccine protein, and a second nucleotide sequence that encodes a T cell costimulatory fusion protein, wherein the T cell costimulatory fusion protein enhances activation of antigen-specific T cells when administered to a subject. In some embodiments, this document features an expression vector containing a first nucleotide sequence that encodes a secretable gp96-Ig fusion protein, and a second nucleotide sequence that encodes a T cell costimulatory fusion protein, wherein the T cell costimulatory fusion protein enhances activation of antigen-specific T cells when administered to a subject. The expression vector can be a mammalian expression vector. In an embodiment, the secretable gp96-Ig fusion protein can lack the gp96 KDEL (SEQ ID NO:3) sequence. The Ig tag in the gp96-Ig fusion protein can include the Fc region of human IgG1, IgG2, IgG3, IgG4, IgM, IgA, or IgE. The T cell costimulatory fusion protein can be OX40L-Ig or a portion thereof that binds to OX40, ICOSL-Ig or a portion thereof that binds to ICOS, 4-1BBL-Ig or a portion thereof that binds to 4-1BBR, TL1A-Ig or a portion thereof that binds to TNFRSF25, GITRL-Ig or a portion thereof that binds to GITR, CD40-Ig or a portion thereof that binds to CD40, or CD70-Ig or a portion thereof that binds to CD27, among others. The Ig tag in the T cell costimulatory fusion protein can include the Fc region of human IgG1, IgG2, IgG3, IgG4, IgM, IgA, or IgE. The expression vector can contain DNA or RNA.

In another aspect, this document features a composition containing an expression vector that comprises a first nucleotide sequence encoding a secretable vaccine protein, such as a secretable gp96-Ig fusion protein, and a second nucleotide sequence encoding a T cell costimulatory fusion protein, wherein the T cell costimulatory fusion protein enhances activation of antigen-specific T cells when administered to a subject. The vector can be a DNA-based mammalian expression vector. In an embodiment, the secretable gp96-Ig fusion protein can lack the gp96 KDEL (SEQ ID NO:3) sequence. The Ig tag in the gp96-Ig fusion protein can contain the Fc region of human IgG1, IgG2, IgG3, IgG4, IgM, IgA, or IgE. The T cell costimulatory fusion protein can be OX40L-Ig or a portion thereof that binds to OX40, ICOSL-Ig or a portion thereof that binds to ICOS, 4-1BBL-Ig or a portion thereof that binds to 4-1BBR, TL1A-Ig or a portion thereof that binds to TNFRSF25, GITRL-Ig or a portion thereof that binds to GITR, CD40L-Ig or a portion thereof that binds to CD40, or CD70-Ig or a portion thereof that binds to CD27. The Ig tag in the T cell costimulatory fusion protein can include the Fc region of human IgG1, IgG2, IgG3, IgG4, IgM, IgA, or IgE. The expression vector can be incorporated into a virus or virus-like particle, or can be incorporated into a human tumor cell (e.g., a human tumor cell from an established cell line, e.g. a NSCLC, bladder cancer, melanoma, ovarian cancer, renal cell carcinoma, prostate carcinoma, sarcoma, breast carcinoma, squamous cell carcinoma, head and neck carcinoma, hepatocellular carcinoma, pancreatic carcinoma, or colon carcinoma cell line).

In another aspect, this document features a cell comprising a composition containing an expression vector that comprises a first nucleotide sequence encoding a secretable vaccine protein, and a second nucleotide sequence encoding a T cell costimulatory fusion protein, wherein the T cell costimulatory fusion protein enhances activation of antigen-specific T cells when administered to a subject. In some embodiments, this document features a cell comprising a composition containing an expression vector that comprises a first nucleotide sequence encoding a secretable gp96-Ig fusion protein, and a second nucleotide sequence encoding a T cell costimulatory fusion protein, wherein the T cell costimulatory fusion protein enhances activation of antigen-specific T cells when administered to a subject. Such a cell, in various embodiments, can be suitable for use as an off-the-shelf therapy. Such a cell, in various embodiments, is irradiated. Such a cell, in various embodiments, is live and attenuated. These cells, in various embodiments, express tumor antigens which may be chaperoned by the vaccine protein (e.g., gp96) of the present compositions. Such a cell, in various embodiments, can be derived from an established cell line e.g., a human tumor cell from an established NSCLC, bladder cancer, melanoma, ovarian cancer, renal cell carcinoma, prostate carcinoma, sarcoma, breast carcinoma, squamous cell carcinoma, head and neck carcinoma, hepatocellular carcinoma, pancreatic carcinoma, or colon carcinoma cell line. Such a cell, in various embodiments, can be derived from an established prostate cancer cell line. Such a cell, in various embodiments, can be derived from an established lung cancer cell line. Such a cell, in various embodiments, can be derived from an established bladder cancer cell line. Such a cell, in various embodiments, can be derived from an established sarcoma cell line. Such a cell, in various embodiments, can be derived from an established choriocarcinoma cancer cell line.

In another aspect, this document features a method for treating a subject. The method can include administering to a subject an effective amount of a composition described herein, for instance, containing an expression vector that includes a first nucleotide sequence encoding a secretable vaccine protein such as a secretable gp96-Ig fusion protein, and a second nucleotide sequence encoding a T cell costimulatory fusion protein, wherein the T cell costimulatory fusion protein enhances activation of antigen-specific T cells when administered to the subject. The vector can be incorporated into a virus or virus-like particle, or incorporated into a human tumor cell. The subject can be a human cancer patient. Administration of the composition to the human patient can increase the activation or proliferation of tumor antigen specific T cells in the patient. For example, the activation or proliferation of tumor antigen specific T cells in the patient can be increased by at least 25 percent (e.g., at least 30 percent, at least 40 percent, at least 50 percent, at least 60 percent, at least 70 percent, or at least 75 percent) as compared to the level of activation or proliferation of tumor antigen specific T cells in the patient prior to the administration. The method can include administering the composition to a human cancer patient in combination with an agent that inhibits immunosuppressive molecules produced by tumor cells. The agent can be an antibody against PD-1. The subject can be a human with an acute or chronic infection (e.g., an infection by hepatitis C virus, hepatitis B virus, human immunodeficiency virus, or malaria). Administration of the composition to the human patient can stimulate the activation or proliferation of pathogenic antigen specific T cells. The T cell costimulatory molecule can enhance the activation of antigen-specific T cells in the subject to a greater level than gp96-Ig vaccination alone.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4A-4G show that an OX40 agonist antibody in combination with 96-Ig cellular vaccine promotes antigen specific CD8 proliferation, while FOXP3+ Tregs remain unaffected. FIGS. 4A-4D depict the 96-Ig cellular vaccine mechanism of action. In FIG. 4A, vaccine cells secrete gp96-Ig along with cell-derived antigens, or in the case of FIGS. 5, 6, and 8, the single antigen chicken ovalbumin which is stably expressed in this vaccine cell line. In FIG. 4B, gp96-Ig/antigen complexes are taken up by APCs and the antigens are transferred to MHC class I molecules. In FIG. 4C, antigen cross-presentation leads to CD8+ specific T cell activation. In FIG. 4D, in the context of a tumor, the activated CD8+ T cells can recognize shared tumor antigens on distant tumors and destroy them. FIG. 4E is a graph plotting antigen specific (OT-1) cell expansion following vaccination with ImPACT (as used herein, this refers to a modified (e.g. KDEL deletion) gp96-Ig fusion protein or, in some cases, an engineered cell line designed to express the gp96-Ig fusion protein) alone or in combination with agonistic T cell co-stimulatory antibodies for ICOS, 4-1BB, or OX40. Data are shown for days 5 and 40 following the initial vaccination (prime and memory, respectively). The latter also corresponds to 5 days after the second, boost vaccination. Only the ImPACT/OX40(ab) combination generated OT-1 expansion that was significantly greater than ImPACT on its own (*, p<0.05). Experimental replicates are listed. Plotted values are the mean and error is SEM. For each data set in FIG. 4E, the order of histograms from left to right is: No Vaccine, ImPACT alone, ImPACT plus ICOS antibody, ImPact plus OX40 antibody, and ImPact plus 4-1BB antibody. FIG. 4F is a graph plotting FOXP3+ Tregs as a percentage of total CD4+ cells. With the exception of ImPACT/4-1BB treated mice, which fluctuated from increased to decreased FOXP3+ cells, there was no significant change in Tregs following ImPACT treatment, emphasizing its specificity towards CD8+ expansion. Experimental replicates are listed. Plotted values are the mean and error is SEM. For each data set in FIG. 4F, the order of histograms from left to right is: No Vaccine, ImPACT alone, ImPact plus ICOS antibody, ImPact plus OX40 antibody, and ImPact plus 4-1BB antibody. FIG. 4G is a pair of graphs plotting OT-1/CD8 and FOXP3+ cell expansion in a second model system in response to the adjuvant Alum. Again, the combination of ImPACT and OX40(ab) resulted in significant OT-1 proliferation, in addition to a moderate increase in FOXP3+ cells. Experimental replicates are listed. Plotted values are the mean and error is SEM. For each data set in FIG. 4G, the order of histograms from left to right is: No Vaccine, IgG control, and ImPact plus OX40 antibody.

FIGS. 5A-5D show that T cell co-stimulator OX40 functions synergistically with the ImPACT (gp96-Ig) cellular vaccine to activate T cells and produce antigen specific CD8+ expansion. FIG. 5A is a schematic representation of receptor (OX40, ICOS, and 4-1BB) and ligand (OX40L, ICOSL, and 4-1BBL) interactions between T cells and antigen presenting cells (APC) promoting T cell activation. FIG. 5B is a diagram depicting a vaccine cell line established through selection of a clonal population of cells expressing gp96-Ig/HLA-A1 (ImPACT) along with the single antigen chicken ovalbumin, in order to track antigen specific T cell expansion (OT-I cells) following the administration of vaccine. FIG. 5C is a list of murine T cell co-stimulator agonist antibodies tested in combination with ImPACT for synergism in promoting T cell expansion—all of these antibodies are useful in various embodiments as combination therapy agents. FIG. 5D is a graph plotting OT-1 levels in FOXP3-RFP reporter mice that were seeded with antigen specific OT-1 (CD8) cells labeled with GFP via tail vein injection on day −1, as detected by flow cytometry for 43 days after vaccination with either ImPACT alone, or ImPACT in combination with 100 µg of agonist T cell co-stimulatory antibodies for OX40, ICOS, or 4-1BB on day 0. Unvaccinated (No Vaccine) mice were assessed in parallel as a control. Mice were boosted with vaccine or vaccine/ antibody combinations again on day 35. Vaccination days are indicated by syringes. The initial (prime) response peaked on day 5, and only vaccine/OX40(ab) treated mice showed a modest memory response following boost (arrows). Plotted values represent the mean percentage of OT-1 cells from all CD8+ cells and error is SEM. See also FIGS. 4A-G for the number of experimental replicates and statistical significance between sample groups.

FIG. 6A depicts the experimental design to compare (a) antigen specific T cell expansion using the original vaccine ImPACT (Gp96-Ig) in combination with OX40 agonist antibody to (b) the new vaccine ComPACT (in this figure, Gp96-Ig/OX40L-Fc). FIG. 6B depicts the peak of antigen-specific CD8+ T cell proliferation following primary immunization with a control vaccine, a vaccine expressing ovalbumin, a vaccine expressing ovalbumin and gp96-Ig (ImPACT), ImPACT in combination with OX40 agonist antibodies, or ComPACT. For each data set in FIG. 6B, the order of peaks from left to right is: No Vaccine, Ova only control, ImPACT, ImPACT plus OX40 antibody, and ComPACT. FIG. 6C is a graph plotting the OT-1 expansion time-course (similar to FIG. 5D), using FOXP3-RFP mice seeded with OT-1 (CD8) cells on day −1. OT-1/GFP cells were analyzed by flow cytometry in mice treated with No Vaccine, Ova only control cells, ImPACT, ImPACT+100 µg OX40(ab), and ComPACT, over 46 days, with initial vaccination on day 0 and a boost on day 35 (indicated by syringes). Both prime and memory responses (arrows) were greatest in mice treated with ComPACT, even when compared with ImPACT+OX40(ab). ComPACT mice also surprisingly retained elevated OT-1 levels throughout the time-course (~days 7-20). Plotted values represent the mean and error is SEM. See also FIGS. 7A-7F for the number of experimental replicates and statistical significance between sample groups.

FIGS. 7A-7D show the characterization of the 3T3-version of ComPACT as used in FIG. 6C. 3T3 cells were transfected with a plasmid expressing chicken ovalbumin (Ova), and a single high-expressing clone was established and used to re-transfect with Vaccine vectors (either gp96-Ig alone, gp96-Ig/OX40L-Fc, gp96-Ig/ICOSL, or gp96-Ig/4-1BBL). Vaccines were therefore established in the same Ova parental clone. Unvaccinated mice (No vaccine) were compared with mice treated with Ova only expressing cells (as an additional control), ImPACT (Ova-gp96-Ig), ImPACT+ OX40 agonist antibody (OX40(ab)), ComPACT (Ova-gp96-Ig/ICOSL), ComPACT (Ova-gp96-Ig/OX40L-Fc), or ComPACT (Ova-gp96-Ig/1BBL). FIG. 7A is a graph plotting Ova secretion as confirmed by ELISA, showing that secretion was essentially identical between Ova only control, ImPACT, and the various ComPACT cells. Values are the mean from a minimum of 6 replicates and error is SEM. For each data set in FIG. 7A, the order of histograms from left to right is: Ova only control, ImPACT (3T3-ova-gp96-Ig), ComPACT (Ova-gp96-Ig/ICOSL), ComPACT (Ova-gp96-Ig/OX40L-Fc), and ComPACT (Ova-gp96-Ig/1BBL). FIG. 7B is a graph plotting gp96-Ig secretion (detected as IgG) as determined by ELISA, showing that individual ImPACT and ComPACT clones were established that secreted comparable levels. Values are the mean from a minimum of 6 replicates and error is SEM. For each data set in FIG. 7B, the order of histograms from left to right is: Ova only control, ImPACT (3T3-ova-gp96-Ig), ComPACT (Ova-gp96-Ig/ICOSL), ComPACT (Ova-gp96-Ig/OX40L-Fc), and ComPACT (Ova-gp96-Ig/1BBL). FIG. 7C is a graph plotting mRNA expression of ICOSL, OX40L, or 4-1BBL as confirmed by qRT-PCR, showing expression only in ComPACT cells. Graphical values are the mean from a minimum of 3 distinct replicates and error is SEM. For each data set in FIG. 7C, the order of histograms from left to right is: Ova only control, ImPACT (3T3-ova-gp96-Ig), ComPACT (Ova-gp96-Ig/ ICOSL), ComPACT (Ova-gp96-Ig/OX40L-Fc), and ComPACT (Ova-gp96-Ig/1BBL). FIG. 7D provides Western blots showing confirmation of OX40L, ICOSL, and 4-1BBL expression in ComPACT cells. ImPACT and ComPACT cells were treated with Brefeldin A (BFA) for 16 hours to prevent protein transport and secretion. Cells were then harvested, lysed and subjected to SDS PAGE/Western blot analysis. Blots were probed with an antibody to OX40L (also known as CD252), ICOSL, or 4-1BBL, and histone H3 or actin B (ACTB) as a loading control. OX40L, ICOSL, and 4-1BBL were only detected in ComPACT cells. FIG. 7E is a graph plotting the frequency of CD4+FoxP3+ regulatory T cells on day 5 following the indicated primary immunization. For each data set in FIG. 7E, the order of peaks from left to right is: No vaccine, Ova only control, ImPACT, ImPACT plus OX40 antibody, and ComPACT (in this figure, Ova-gp96-Ig/OX40L-Fc). FIG. 7F is a pair of graphs plotting the frequency of antigen-specific CD8+ T cells (OT-I) in the peripheral blood on day 42 (7 days following the boost immunization), shown on the left, and the peak of CD4+ FoxP3+ T regulatory cells on the same day in the peripheral blood. As in FIG. 6C, antigen specific (OT-1) cell expansion following vaccination with an Ova only expressing cell line, ImPACT, ImPACT in combination with OX40(ab) and ComPACT (in this case, Ova-gp96-Ig/OX40L-Fc), are shown at 5 and 40 days following the initial vaccination (prime and memory, respectively). The latter also corresponds to 5 days after the second, boost vaccination. OT-1 levels in ImPACT, ImPACT+OX40(ab) and ComPACT treated mice are significantly elevated compared to Ova only control treated mice. ComPACT treated mice exhibit the greatest proliferation of OT-1 cells, which are significantly higher than ImPACT+OX40(ab) at both prime and memory response points. Experimental replicates are listed and error is SEM. For each data set in FIG. 7F, the order of peaks from left to right is: No vaccine, Ova only control, ImPACT, ImPACT plus OX40 antibody, and ComPACT (in this figure, Ova-gp96-Ig/OX40L-Fc).

FIG. 8A is a series of graphs plotting total numbers of mononuclear (MNC), CD4, CD8, OT-I, and OT-II cells in mice that were either untreated or vaccinated with ImPACT, ImPACT+OX40(ab), or ComPACT (in this figure, Gp96-Ig/OX40L-Fc). As for FIGS. 5D and 6C, FOXP3-RFP reporter mice were seeded with OT-1 cells via tail vein injection on day −1, vaccinated on day 0, and sacrificed on day 8 for analysis, including flow cytometry of cells obtained from peritoneal wash. ComPACT treatment produced a robust OT-I (CD8) specific response, whereas OX40(ab) treatment resulted in an increase in all T cell sub-types, including FOXP3+ CD4 cells. Plotted values represent the mean from a minimum of 3 mice and error is SEM. For each data set in FIG. 8A, the order of peaks from left to right is: Untreated, ImPACT, ImPACT plus OX40 antibody, and ComPACT (in this figure, Gp96-Ig/OX40L-Fc). FIG. 8B is a series of graphs plotting numbers of $CD127^+KLRG1^-$, $CD127^-KLRG1^+$, and $CD127^+KLRG1^+$ cells, which correspond to memory precursor cells, short-lived effector cells, and memory cells, respectively, on day 8 following the primary immunization. The cells were derived from the spleen (top panels) and peritoneal cavity (bottom panels). For each data set in FIG. 8B, the order of peaks from left to right is: Untreated, Ova only, ImPACT, ComPACT (Ova-gp96-Ig/ICOSL), ComPACT (Ova-gp96-Ig/OX40L-Fc), and ComPACT (Ova-gp96-Ig/1BBL). FIG. 8C is a series of graphs plotting levels of INFγ, TNFα, IL2, IL6, and IL5. Whole blood serum was harvested from the same mice presented in FIG. 8A above on day 8, and subjected to cytokine analysis using the LEGENDPLEX™ kit from BioLegend and flow cytometer. Consistent with the data of FIG. 8A, OX40(ab) treatment produced a non-specific, systemic immune response, with elevated levels of not only INFγ, TNFα and IL2, but also IL6 and IL5. Plotted values represent the mean from a minimum of 3 mice and error is SEM. For each data set in FIG. 8C, the order of peaks from left to right is: Untreated, ImPACT, ImPACT plus OX40 antibody, and ComPACT (in this figure, Gp96-Ig/ OX40L-Fc). FIG. 8D is a series of graphs plotting gene expression levels for FNγTNFα, and Granzyme-B (GZMB). Analysis of T cell activation genes by qRT-PCR demonstrated ComPACT's specificity in only activating antigen specific CD8 (OT-I+) cells, compared to OX40(ab), which non-specifically activated both endogenous (OT-I−) and antigen specific CD8 (OT-I+) cells. Cells obtained from peritoneal washes in FIG. 8A above were sorted into populations of OT-1− and OT-1+ CD8 cells. Total RNA was harvested, reverse transcribed and analyzed by qPCR. Gene expression levels of IFNγ, TNFα, and GZMB are shown, normalized to 18S mRNA with the first ImPACT only treated replicate set at 1. Plotted values represent the mean from a minimum of 3 mice, and error is SEM. For each data set in FIG. 8D, the order of histograms from left to right is: ImPACT, ImPACT plus OX40 antibody, and ComPACT (in this figure, Gp96-Ig/OX40L-Fc). FIG. 8E shows the number of FOXP3 regulatory T cells (Treg) in splenocytes and tumor draining lymph node (TDLN) in the mice. For each data set in FIG. 8E, the order of peaks from left to right is: Untreated, ImPACT, ImPACT plus OX40 antibody, and ComPACT (in this figure, Gp96-Ig/OX40L-Fc).

FIG. 9A is a series of graphs plotting total numbers of MNC, CD4, CD8, OT-I, and OT-II cells for mice either untreated or vaccinated with ImPACT, ImPACT+OX40(ab), or ComPACT. As in FIGS. 5D and 6C, FIR reporter mice were seeded with OT-1 cells via tail vein injection on day −1, vaccinated on day 0, and sacrificed on day 8 for analysis, including flow cytometry of cells obtained from the spleen. OX40(ab) treated mice demonstrated an increase in all T cell sub-types, including CD4/FOXP3+ cells. ComPACT treated mice produced a robust OT-1 (CD8) specific response that was significantly higher than the OX40(ab) response. Plotted values represent the mean from a minimum of 3 mice and error is SEM. For each data set in FIG. 9A, the order of peaks from left to right is: Untreated, ImPACT, ImPACT plus OX40 antibody, and ComPACT. FIG. 9B is a series of graphs plotting total numbers of MNC, CD4, CD8, OT-I, and OT-II cells for mice either untreated or vaccinated with ImPACT, ImPACT+OX40(ab), or ComPACT as in FIG. 9A, except in peripheral lymph nodes. For each data set in FIG. 9B, the order of peaks from left to right is: Untreated, ImPACT, ImPACT plus OX40 antibody, and ComPACT. FIG. 9C is a series of graphs plotting mRNA expression for T cell activation genes (ACTB, IL2, and Perforin 1 (PRF1)). qRT-PCR revealed antigen specific OT-1 (CD8) activation in mice treated with ComPACT, compared to non-specific activation of both endogenous and antigen specific OT-1 CD8 cells in mice treated with OX40(ab). Cells obtained from peritoneal washes in FIG. 8A above were sorted into populations of OT-1+ and OT-1− CD8 cells. Total RNA was harvested, reverse transcribed, and analyzed by qPCR. ACTB levels were consistent between cell populations and treatments, serving as a control. IL2 levels were significantly elevated in OT-1+ cells of mice treated with ImPACT, ImPACT+OX40(ab), and ComPACT, indicating significant T cell activation with all vaccines/combinations. Consistent with FIG. 8C, levels of PRF1 were elevated non-specifically in both OT-1− and OT-1+ CD8 fractions of mice treated with OX40(ab), while only increasing in OT-1+ cells of ComPACT treated mice. Plotted values represent the mean from a minimum of 3 mice and error is SEM. For each data set in FIG. 9C, the order of histograms from left to right is: ImPACT, ImPACT plus OX40 antibody, and ComPACT.

FIG. 10A is a schematic of the experimental setup. BALB/C mice were inoculated with $2\times10^5$ CT26 cells sub-dermally, indicating day 0. On days 6 and 11, mice were either unvaccinated or vaccinated with ImPACT, ImPACT+OX86(ab), ComPACT, or OX86(ab) alone. Vaccine treatments consisted of $1\times10^6$ cells and 100 μg of antibody. FIG. 10B is a graph plotting tumor area on the indicated days following tumor inoculation on day 0 and is plotted as the mean from a minimum of 5 experimental mice per sample group, with error as SEM. FIG. 10C is a graph plotting tumor area on day 21 of the study. For each data set in FIG. 10C, the order of peaks from left to right is: No vaccine, CT26 only control, OX40 antibody only, ImPACT, ImPACT plus OX40 antibody, and ComPACT.

FIGS. 11A-11E show that ComPACT (in this figure, Gp96-Ig/OX40L-Fc) treatment resulted in CD8+ specific tumor infiltration, hindered tumor growth, increased overall survival and significant tumor rejection in the CT26 colorectal carcinoma model. In FIG. 11A, mice were inoculated on day 0 with $5\times10^5$ CT26 tumor cells injected subcutaneously in the rear flank. Mice were either untreated or vaccinated on days 4, 7 and 10 with CT26 parental cells, OX40(ab) alone, ImPACT alone, ImPACT+OX40(ab) or ComPACT. A cohort of mice were sacrificed on day 12 for tumor genetic analysis. Remaining mice were monitored for 30 days to measure tumor area and overall survival. FIG. 11B depicts analysis of day 12 tumor gene expression. Total RNA was isolated from dissociated tumors, reverse transcribed and analyzed by qPCR. Values were normalized to 18S mRNA and the first 'Untreated' only replicate was set at 1. For each data set in FIG. 11B, the order of histograms from left to right is: Untreated, CT26 only control, OX40 antibody only, ImPACT, ImPACT plus OX40 antibody, and ComPACT. In FIG. 11C, AH1-tetramer/antigen specific CD8+ cells were analyzed in treated mice. For each data set in FIG. 11C, the order of peaks from left to right is: Untreated, CT26 only control, OX40 antibody only, ImPACT, ImPACT plus OX40 antibody, and ComPACT. FIG. 11D shows tumor area as measured daily for 21 days following initial tumor inoculation. In FIG. 11E, overall survival was determined over a 30 day time course. 80% of ComPACT treated mice survived according to experimental criteria and 47% of mice (7 out of 15) completely rejected established tumors. One OX40(ab) only treated mouse rejected the tumor by day 24 and one ImPACT+OX40(ab) treated mouse rejected by day 25.

FIGS. 12A-12D show that ComPACT (in this figure, Gp96-Ig/OX40L-Fc) generates antigen-specific CD8+ expansion, delayed tumor growth, increased overall survival and tumor rejection in an aggressive B16.F10-ova melanoma model. In FIG. 12A, mice were adoptively transferred with $5\times10^5$ OT-I cells on day −1, and then inoculated on day 0 with $5\times10^5$ B16.F10-ova tumor cells injected subcutaneously in the rear flank. Mice were either untreated or vaccinated on days 4, 7 and 10 with B16.F10-ova parental cells, OX40(ab) alone, ImPACT alone, ImPACT+OX40(ab) or ComPACT. FIG. 12B shows antigen-specific CD8+ (OT-I) expansion following treatment over a time-course of 25 days. In FIG. 12C, tumor area was measured throughout a 25 day time course following initial tumor inoculation. In FIG. 12D, overall survival was determined over a 30 day time course. Approximately 78% of ComPACT treated mice survived and 11% of the ComPACT treated mice completely rejected established tumors. Only the ComPACT treated group had complete tumor rejecters: 1 out of 9 mice or approximately 11%.

FIG. 15 is a graph showing the effect of ComPACT on tumor growth kinetics in the CT26 colorectal carcinoma model. Mice were inoculated on day 0 with $5 \times 10^5$ CT26 tumor cells injected subcutaneously in the rear flank. Mice were either untreated or vaccinated on days 4, 7 and 10 with CT26 parental cells, ImPACT alone, ImPACT+the TNFRSF25 agonist (4C12 ab), 4C12 (ab) alone, PD-1 (ab) alone, 4C12 (ab) and PD-1 (ab), ComPACT (gp96-Ig/OX40L or gp96-Ig/TL1A), ComPACT (gp96-Ig/OX40L)+PD-1 (ab), or ComPACT² (gp96-Ig/OX40L+TL1A). The mice were monitored for 30 days to measure tumor area. ComPACT² (gp96-Ig/OX40L+TL1A) represents a combination injection including ComPACT-OX40L and ComPACT-TL1A (i.e., two different cell lines in the same syringe).

FIG. 16 is a graph showing the effect of ComPACT on overall mice survival in the CT26 colorectal carcinoma model. Mice were treated with CT26 tumor cells and vaccinated as described in FIG. 15.

FIG. 17 is a graph showing the amount of human OX40L produced by a human prostate specific vaccine (HS-1020, PC-3 cell line).

FIG. 18 is a graph showing the amount of human OX40L produced by a human lung specific vaccine (HS-120, AD100 cell line)

DETAILED DESCRIPTION

Figure 1:
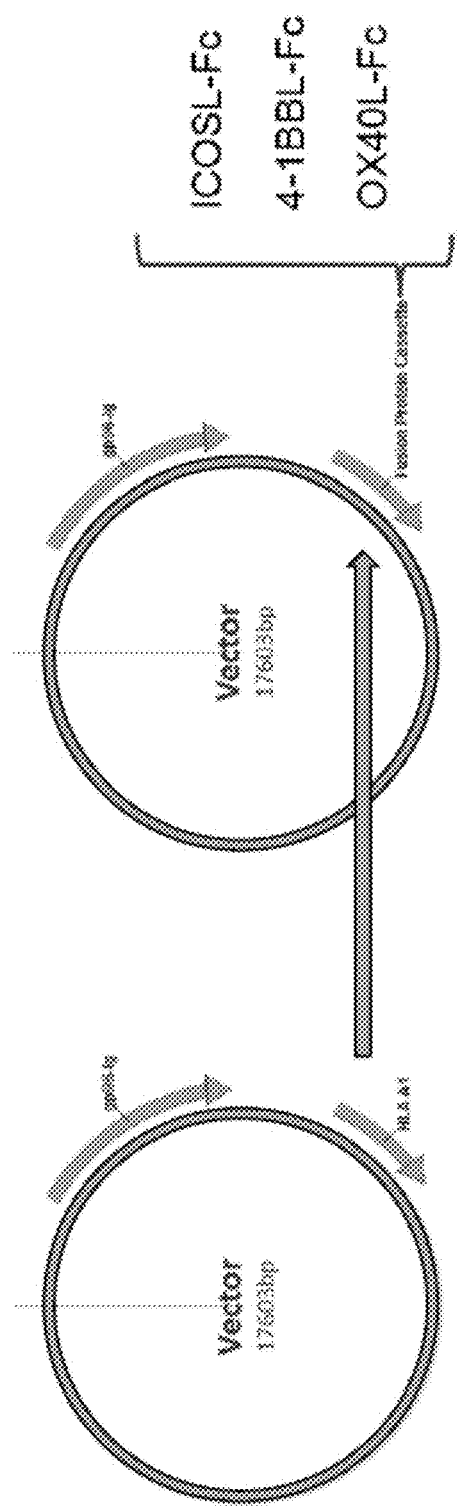
FIG. 1 is a schematic representation of the re-engineering of an original gp96-Ig vector to generate a cell-based combination product that encodes the gp96-Ig fusion protein in a first cassette, and a T cell costimulatory fusion protein in a second cassette. ICOS-Fc, 4-1BBL-Fc, and OX40L-Fc are shown for illustration.

Various secretable proteins, i.e. vaccine proteins as described herein, can be used to stimulate an immune response in vivo. For example, secretable heat-shock protein gp96-Ig based allogeneic cellular vaccines can achieve high-frequency polyclonal CD8+ T cell responses to femtomolar concentrations of tumor antigens through antigen cross-priming in vivo (Oizumi et al., *J Immunol* 2007, 179(4):2310-2317) Multiple immunosuppressive mechanisms elaborated by established tumors can dampen the activity of this vaccine approach, however. To evaluate the potential utility of combination immunotherapy for patients with advanced disease, a systematic comparison of PD-1, PD-L1, CTLA-4, and LAG-3 blocking antibodies in mouse models of long-established B16-F10 melanoma was carried out (see, the Examples herein), demonstrating superior combination between gp96-Ig vaccination and PD-1 blockade as compared to other checkpoints. Synergistic anti-tumor benefits may result from triple combinations of gp96-Ig vaccination, PD-1 blockade, and T cell costimulation using one or of an agonist of OX40 (e.g., an OX40 ligand-Ig (OX40L-Ig) fusion, or a fragment thereof that binds OX40), an agonist of inducible T-cell costimulator (ICOS) (e.g., an ICOS ligand-Ig (ICOSL-Ig) fusion, or a fragment thereof that binds ICOS), an agonist of CD40 (e.g., a CD40L-Ig fusion protein, or fragment thereof), an agonist of CD27 (e.g. a CD70-Ig fusion protein or fragment thereof), an agonist of 4-1BB (e.g., a 4-1BB ligand-Ig (4-1BBL-Ig) fusion, or a fragment thereof that binds 4-1BB), an agonist of TNFRSF25 (e.g., a TL1A-Ig fusion, or a fragment thereof that binds TNFRSF25), or an agonist of glucocorticoid-induced tumor necrosis factor receptor (GITR) (e.g., a GITR ligand-Ig (GITRL-Ig) fusion, or a fragment thereof that binds GITF). The enthusiasm for development of such triple combinations is tempered by the anticipated cost of such therapies, however. To circumvent this issue, vaccine protein expressing vectors (e.g., gp96-Ig expressing vectors) were re-engineered to simultaneously express T cell costimulatory protein (e.g., ICOSL-Ig, 4-1BBL-Ig, or OX40L-Ig), to provide a costimulatory benefit without the need for an additional antibody therapy. The re-engineered vectors are provided herein, as are methods for their use. When gp96-Ig and these costimulatory fusion proteins were secreted by allogeneic cell lines, enhanced activation of antigen-specific CD8+ T cells was observed (see, the Examples herein). Thus, combination immunotherapy can be achieved by vector re-engineering to obviate the need for completely separate vaccine/antibody/fusion protein regimens.

Vaccine Proteins

Vaccine proteins can induce immune responses that find use in the present invention. In various embodiments, the present invention provides expression vectors comprising a first nucleotide sequence that encode a secretable vaccine protein and a second nucleotide sequence that encode a T cell costimulatory fusion protein. Compositions comprising the expression vectors of the present invention are also provided. In various embodiments, such compositions are utilized in methods of treating subjects to stimulate immune responses in the subject including enhancing the activation of antigen-specific T cells in the subject. The present compositions find use in the treatment of various diseases including cancer.

The heat shock protein (hsp) gp96, localized in the endoplasmic reticulum (ER), serves as a chaperone for peptides on their way to MHC class I and II molecules. Gp96 obtained from tumor cells and used as a vaccine can induce specific tumor immunity, presumably through the transport of tumor-specific peptides to antigen-presenting cells (APCs) (*J Immunol* 1999, 163(10):5178-5182). For example, gp96-associated peptides are cross-presented to CD8 cells by dendritic cells (DCs).

A vaccination system was developed for antitumor therapy by transfecting a gp96-Ig G1-Fc fusion protein into tumor cells, resulting in secretion of gp96-Ig in complex with chaperoned tumor peptides (see, *J Immunother* 2008, 31(4):394-401, and references cited therein). Parenteral administration of gp96-Ig secreting tumor cells triggers robust, antigen-specific CD8 cytotoxic T lymphocyte (CTL) expansion, combined with activation of the innate immune system. Tumor-secreted gp96 causes the recruitment of DCs and natural killer (NK) cells to the site of gp96 secretion, and mediates DC activation. Further, the endocytic uptake of gp96 and its chaperoned peptides triggers peptide cross presentation via major MHC class I, as well as strong, cognate CD8 activation independent of CD4 cells.

The vectors provided herein contain a first nucleotide sequence that encodes a gp96-Ig fusion protein. The coding region of human gp96 is 2,412 bases in length (SEQ ID NO:1), and encodes an 803 amino acid protein (SEQ ID NO:2) that includes a 21 amino acid signal peptide at the amino terminus, a potential transmembrane region rich in hydrophobic residues, and an ER retention peptide sequence at the carboxyl terminus (GENBANK® Accession No.

X15187; see, Maki et al., *Proc Natl Acad Sci USA* 1990, 87:5658-5562). The DNA and protein sequences of human gp96 follow:

(SEQ ID NO: 1)
```
atgagggccctgtgggtgctgggcctctgctgcgtcctgctgaccttcgg
gtcggtcagagctgacgatgaagttgatgtggatggtacagtagaagag
atctgggtaaaagtagagaaggatcaaggacggatgatgaagtagtacag
agagaggaagaagctattcagttggatggattaaatgcatcacaaataag
agaacttagagagaagtcggaaaagtttgccttccaagccgaagttaaca
gaatgatgaacttatcatcaattcattgtataaaaataaagagattacc
tgagagaactgatttcaaatgcttctgatgctttagataagataaggcta
atatcactgactgatgaaaatgctctactggaaatgaggaactaacagtc
aaaattaagtgtgataaggagaagaacctgctgcatgtcacagacaccgg
tgtaggaatgaccagagaagagttggttaaaaaccttggtaccatagcca
aatctgggacaagcgagttttaaacaaaatgactgaagcacaggaagat
ggccagtcaacttctgaattgattggccagtaggtgtcggtactattccg
ccttccttgtagcagataaggttattgtcacttcaaaacacaacaacgat
acccagcacatctgggagtctgactccaatgaattttctgtaattgctga
cccaagaggaaacactctaggacggggaacgacaattacccttgtcttaa
aagaagaagcatctgattaccttgaattggatacaattaaaaatctcgtc
aaaaaatattcacagttcataaactacctatttatgtatggagcagcaag
actgaaactgagaggagcccatggaggaagaagaagcagccaaagaagag
aaagaagaatctgatgatgaagctgcagtagaggaagaagaagaagaaaa
gaaaccaaagactaaaaaagttgaaaaaactgtctgggactgggaactta
tgaatgatatcaaaccaatatggcagagaccatcaaaagaagtagaagaa
gatgaatacaaagctactacaaatcattttcaaaggaaagtgatgacccc
atggcttatattcactttactgctgaaggggaagttaccttcaaatcaat
tttatttgtacccacatctgctccacgtggtctgtagacgaatatggatc
taaaaagagcgattacattaagctctatgtgcgccgtgtattcatcacag
acgacttccatgatatgatgcctaaatacctcaattagtcaagggtgtgg
tggactcagatgatctcccctttgaatgtttcccgcgagactcttcagcaa
cataaactgcttaaggtgattaggaagaagcttgacgtaaaacgctggac
atgatcaagaagattgctgatgataaatacaatgatacttttttggaaga
ataggtaccaacatcaagcttggtgtgattgaagaccactcgaatcgaac
acgtcttgctaaacttcttaggttccagtcttctcatcatccaactgaca
ttactagcctagaccagtatgtggaaagaatgaaggaaaaacaagacaaa
atctacttcatggctgggtccagcagaaaagaggctgaatcttctccatt
tgttgagcgacttctgaaaaagggctatgaagttatttacctcacagaac
ctgtggatgaatactgtattcaggcccttcccgaatttgatgggaagagg
accagaatgttgccaaggaaggagtgaagttcgatgaaagtgagaaaact
aaggagagtcgtgaagcagttgagaaagaatttgagcctctgctgaattg
gatgaaagataaagcccttaaggacaagattgaaaaggctgtggtgtctc
agcgcctgacagaatctccgtgtgctttggtggccagccagtacggatgg
tctggcaacatggagagaatcatgaaagcacaagcgtaccaaacgggcaa
ggacatctctacaaattactatgcgagtcagaagaaaacatttgaaatta
atcccagacacccgctgatcagagacatgcttcgacgaattaaggaagat
gaagatgataaaacagtatggatcttgctgtggattgatgaaacagcaac
gcttcggtcagggtatcttttaccagacactaaagcatatggagatagaa
tagaaagaatgcttcgcctcagtttgaacattgaccctgatgcaaaggtg
gaagaagagcccgaagaagaacctgaagagacagcagaagacacaacaga
agacacagagcaagacgaagatgaagaaatggatgtgggaacagatgaag
aagaagaaacagcaaaggaatctacagctgaaaaagatgaattgtaa
```

(SEQ ID NO: 2)
MRALWVLGLCCVLLTFGSVRADDEVDVDGTVEEDLGKSREG

SRTDDEVVQREEEAIQLDGLNASQIRELREKSEKFAFQAEVNR

MMKLIINSLYKNKEIFLRELISNASDALDKIRLISLTDENALSG

NEELTVKIKCDKEKNLLHVTDTGVGMTREELVKNLGTIAKSG

TSEFLNKMTEAQEDGQSTSELIGQFGVGFYSAFLVADKVIVTS

KHNNDTQHIWESDSNEFSVIADPRGNTLGRGTTITLVLKEEAS

DYLELDTIKNLVKKYSQFINFPIYVWSSKTETVEEPMEEEEAA

KEEKEESDDEAAVEEEEEKKPKTKKVEKTVWDWELMNDIK

PIWQRPSKEVEEDEYKAFYKSFSKESDDPMAYIHFTAEGEVTF

KSILFVPTSAPRGLFDEYGSKKSDYIKLYVRRVFITDDFHDMM

PKYLNFVKGVVDSDDLPLNVSRETLQQHKLLKVIRKKLVRKT

LDMIKKIADDKYNDTFWKEFGTNIKLGVIEDHSNRTRLAKLL

RFQSSHHPTDITSLDQYVERMKEKQDKIYFMAGSSRKEAESSP

FVERLLKKGYEVIYLTEPVDEYCIQALPEFDGKRFQNVAKEG

VKFDESEKTKESREAVEKEFEPLLNWMKDKALKDKIEKAVV

SQRLTESPCALVASQYGWSGNMERIMKAQAYQTGKDISTNY

YASQKKTFEINPRHPLIRDMLRRIKEDEDDKTVLDLAVVLFET

ATLRSGYLLPDTKAYGDRIERMLRLSLNIDPDAKVEEEPEEEP

EETAEDTTEDTEQDEDEEMDVGTDEEEETAKESTAEKDEL.

A nucleic acid encoding a gp96-Ig fusion sequence can be produced using the methods described in U.S. Pat. No. 8,685,384, which is incorporated herein by reference in its entirety. In some embodiments, the gp96 portion of a gp96-Ig fusion protein can contain all or a portion of a wild type gp96 sequence (e.g., the human sequence set forth in SEQ ID NO:2). For example, a secretable gp96-Ig fusion protein can include the first 799 amino acids of SEQ ID NO:2, such that it lacks the C-terminal KDEL (SEQ ID NO:3) sequence. Alternatively, the gp96 portion of the fusion protein can have an amino acid sequence that contains one or more substitutions, deletions, or additions as compared to the first 799 amino acids of the wild type gp96 sequence, such that it has at least 90% (e.g., at least 90%, at least 91%, at least 92%, at least 93%, at least 94%, at least 95%, at least 96%, at least 97%, at least 98%, or at least 99%) sequence identity to the wild type polypeptide.

As used throughout this disclosure, the percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: −i is set to a file containing the first nucleic acid sequence to be compared (e.g., C:\seq1.txt); −j is set to a file containing the second nucleic acid sequence to be compared (e.g., C:\seq2.txt); −p is set to blastn; −o is set to any desired file name (e.g., C:\output.txt); −q is set to −1; −r is set to 2; and all other options are left at their default setting. For example, the following command can be used to generate an output file containing a comparison between two sequences: C:\Bl2seq c:\seq1.txt −j c:\seq2.txt −p blastn −o c:\output.txt −q −1 −r 2. To compare two amino acid sequences, the options of Bl2seq are set as follows: −i is set to a file containing the first amino acid sequence to be compared (e.g., C:\seq1.txt); −j is set to a file containing the second amino acid sequence to be compared (e.g., C:\seq2.txt); −p is set to blastp; −o is set to any desired file name (e.g., C:\output.txt); and all other options are left at their default setting. For example, the following command can be used to generate an output file containing a comparison between two amino acid sequences: C:\Bl2seq c:\seq1.txt −j c:\seg2.txt −p blastp −o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:1), or by an articulated length (e.g., 100 consecutive nucleotides or amino acid residues from a sequence set forth in an identified sequence), followed by multiplying the resulting value by 100. For example, a nucleic acid sequence that has 2,200 matches when aligned with the sequence set forth in SEQ ID NO:1 is 91.2 percent identical to the sequence set forth in SEQ ID NO:1 (i.e., 2,000÷2,412×100=91.2). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It also is noted that the length value will always be an integer.

Thus, in some embodiments, the gp96 portion of nucleic acid encoding a gp96-Ig fusion polypeptide can encode an amino acid sequence that differs from the wild type gp96 polypeptide at one or more amino acid positions, such that it contains one or more conservative substitutions, non-conservative substitutions, splice variants, isoforms, homologues from other species, and polymorphisms.

As defined herein, a "conservative substitution" denotes the replacement of an amino acid residue by another, biologically similar, residue. Typically, biological similarity, as referred to above, reflects substitutions on the wild type sequence with conserved amino acids. For example, conservative amino acid substitutions would be expected to have little or no effect on biological activity, particularly if they represent less than 10% of the total number of residues in the polypeptide or protein. Conservative substitutions may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe. Accordingly, conservative substitutions may be effected by exchanging an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. Additional examples of conserved amino acid substitutions, include, without limitation, the substitution of one hydrophobic residue for another, such as isoleucine, valine, leucine, or methionine, or the substitution of one polar residue for another, such as the substitution of arginine for lysine, glutamic for aspartic acid, or glutamine for asparagine, and the like. The term "conservative substitution" also includes the use of a substituted amino acid residue in place of an un-substituted parent amino acid residue, provided that antibodies raised to the substituted polypeptide also immunoreact with the un-substituted polypeptide.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g. selenocysteine, pyrrolysine, N-formylmethionine (β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

Mutations may also be made to the nucleotide sequences of the present fusion proteins by reference to the genetic code, including taking into account codon degeneracy.

The Ig portion ("tag") of a gp96-Ig fusion protein can contain, for example, a non-variable portion of an immunoglobulin molecule (e.g., an IgG1, IgG2, IgG3, IgG4, IgM, IgA, or IgE molecule). Typically, such portions contain at least functional CH2 and CH3 domains of the constant region of an immunoglobulin heavy chain Fusions also can be made using the carboxyl terminus of the Fc portion of a constant domain, or a region immediately amino-terminal to the CH1 of the heavy or light chain. The Ig tag can be from a mammalian (e.g., human, mouse, monkey, or rat) immunoglobulin, but human immunoglobulin can be particularly useful when the 96-Ig fusion is intended for in vivo use for humans.

DNAs encoding immunoglobulin light or heavy chain constant regions are known or readily available from cDNA libraries. See, for example, Adams et al., *Biochemistry* 1980, 19:2711-2719; Gough et al., *Biochemistry* 1980 19:2702-2710; Dolby et al., *Proc Natl Acad Sci USA* 1980, 77:6027-6031; Rice et al., *Proc Natl Acad Sci USA* 1982, 79:7862-7865; Falkner et al., *Nature* 1982, 298:286-288; and Morrison et al., *Ann Rev Immunol* 1984, 2:239-256. Since many immunological reagents and labeling systems are available for the detection of immunoglobulins, gp96-Ig fusion proteins can readily be detected and quantified by a variety of immunological techniques known in the art, such as enzyme-linked immunosorbent assay (ELISA), immunoprecipitation, and fluorescence activated cell sorting (FACS). Similarly, if the peptide tag is an epitope with readily available antibodies, such reagents can be used with the techniques mentioned above to detect, quantitate, and isolate gp96-Ig fusions.

In various embodiments, the 96-Ig fusion protein and/or the costimulatory molecule fusions, comprises a linker In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et. al., (2000), Protein Eng. 13(5):309-312, the entire contents of which are hereby incorporated by reference.

In some embodiments, the linker is a synthetic linker such as PEG.

In other embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid. In various embodiments, the linker is substantially comprised of glycine and serine residues (e.g. about 30%, or about 40%, or about 50%, or about 60%, or about 70%, or about 80%, or about 90%, or about 95%, or about 97% glycines and serines).

In various embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2.

Additional illustrative linkers include, but are not limited to, linkers having the sequence LE, GGGGS (SEQ ID NO:26), (GGGGS)$_n$ (n=1-4) (SEQ ID NO: 27), (Gly)$_8$ (SEQ ID NO:28), (Gly)$_6$ (SEQ ID NO:29), (EAAAK)$_n$ (n=1-3) (SEQ ID NO: 30), A(EAAAK)$_n$A (n=2-5) (SEQ ID NO: 31), AEAAAKEAAAKA (SEQ ID NO: 32), A(EAAAK)$_4$ALEA (EAAAK)$_4$A (SEQ ID NO: 33), PAPAP (SEQ ID NO: 34), KESGSVSSEQLAQFRSLD (SEQ ID NO: 35), EGKSSGSGSESKST (SEQ ID NO: 36), GSAGSAAGS-GEF (SEQ ID NO: 37), and (XP)$_n$, with X designating any amino acid, e.g., Ala, Lys, or Glu.

In various embodiments, the linker may be functional. For example, without limitation, the linker may function to improve the folding and/or stability, improve the expression, improve the pharmacokinetics, and/or improve the bioactivity of the present compositions. In another example, the linker may function to target the compositions to a particular cell type or location.

In some embodiments, a gp96 peptide can be fused to the hinge, CH2 and CH3 domains of murine IgG1 (Bowen et al., *J Immunol* 1996, 156:442-449). This region of the IgG1 molecule contains three cysteine residues that normally are involved in disulfide bonding with other cysteines in the Ig molecule. Since none of the cysteines are required for the peptide to function as a tag, one or more of these cysteine residues can be substituted by another amino acid residue, such as, for example, serine.

Various leader sequences known in the art also can be used for efficient secretion of gp96-Ig fusion proteins from bacterial and mammalian cells (see, von Heijne, *J Mol Biol* 1985, 184:99-105). Leader peptides can be selected based on the intended host cell, and may include bacterial, yeast, viral, animal, and mammalian sequences. For example, the herpes virus glycoprotein D leader peptide is suitable for use in a variety of mammalian cells. Another leader peptide for use in mammalian cells can be obtained from the V-J2-C region of the mouse immunoglobulin kappa chain (Bernard et al., *Proc Natl Acad Sci USA* 1981, 78:5812-5816). DNA sequences encoding peptide tags or leader peptides are known or readily available from libraries or commercial suppliers, and are suitable in the fusion proteins described herein.

Furthermore, in various embodiments, one may substitute the gp96 of the present disclosure with one or more vaccine proteins. For instance, various heat shock proteins are among the vaccine proteins. In various embodiments, the heat shock protein is one or more of a small hsp, hsp40, hsp60, hsp70, hsp90, and hsp110 family member, inclusive of fragments, variants, mutants, derivatives or combinations thereof (Hickey et al., 1989, *Mol. Cell. Biol.* 9:2615-2626; Jindal, 1989, *Mol. Cell. Biol.* 9:2279-2283).

T-Cell Co-Stimulation

In addition to a gp96-Ig fusion protein, the expression vectors provided herein can encode one or more biological response modifiers. In various embodiments, the present expression vectors can encode one or more T cell costimulatory molecules.

In various embodiments, the present expression vectors allow for a robust, antigen-specific CD8 cytotoxic T lymphocyte (CTL) expansion. In various embodiments, the present expression vectors selectively enhance CD8 cytotoxic T lymphocyte (CTL) and do not substantially enhance T cell types that can be pro-tumor, and which include, but are not limited to, Tregs, CD4+ and/or CD8+ T cells expressing one or more checkpoint inhibitory receptors, Th2 cells and Th17 cells. Checkpoint inhibitory receptors refers to receptors (e.g. CTLA-4, B7-H3, B7-H4, TIM-3) expressed on immune cells that prevent or inhibit uncontrolled immune responses. For instance, the present expression vectors do not substantially enhance FOXP3+ regulatory T cells. In some embodiments, this selective CD8 T cell enhancement is in contrast to the non-specific T cell enhancement observed with a combination therapy of a gp-96 fusion and an antibody against a T cell costimultory molecule.

For example, a vector can encode an agonist of OX40 (e.g., an OX40 ligand-Ig (OX40L-Ig) fusion, or a fragment thereof that binds OX40), an agonist of inducible T-cell costimulator (ICOS) (e.g., an ICOS ligand-Ig (ICOSL-Ig) fusion, or a fragment thereof that binds ICOS), an agonist of CD40 (e.g., a CD40L-Ig fusion protein, or fragment thereof), an agonist of CD27 (e.g. a CD70-Ig fusion protein or fragment thereof), or an agonist of 4-1BB (e.g., a 4-1BB ligand-Ig (4-1BBL-Ig) fusion, or a fragment thereof that binds 4-1BB). In some embodiments, a vector can encode an agonist of TNFRSF25 (e.g., a TL1A-Ig fusion, or a fragment thereof that binds TNFRSF25), or an agonist of glucocorticoid-induced tumor necrosis factor receptor (GITR) (e.g., a GITR ligand-Ig (GITRL-Ig) fusion, or a fragment thereof that binds GITR), or an agonist of CD40 (e.g., a CD40 ligand-Ig (CD40L-Ig) fusion, or a fragment thereof that binds CD40); or an agonist of CD27 (e.g., a CD27 ligand-Ig (e.g. CD70L-Ig) fusion, or a fragment thereof that binds CD40).

ICOS is an inducible T cell costimulatory receptor molecule that displays some homology to CD28 and CTLA-4, and interacts with B7-H2 expressed on the surface of antigen-presenting cells. ICOS has been implicated in the regulation of cell-mediated and humoral immune responses.

4-1BB is a type 2 transmembrane glycoprotein belonging to the TNF superfamily, and is expressed on activated T Lymphocytes.

OX40 (also referred to as CD134 or TNFRSF4) is a T cell costimulatory molecule that is engaged by OX40L, and frequently is induced in antigen presenting cells and other cell types. OX40 is known to enhance cytokine expression and survival of effector T cells.

GITR (TNFRSF18) is a T cell costimulatory molecule that is engaged by GITRL and is preferentially expressed in FoxP3+ regulatory T cells. GITR plays a significant role in the maintenance and function of Treg within the tumor microenvironment.

TNFRSF25 is a T cell costimulatory molecule that is preferentially expressed in CD4+ and CD8+ T cells following antigen stimulation. Signaling through TNFRSF25 is provided by TL1A, and functions to enhance T cell sensitivity to IL-2 receptor mediated proliferation in a cognate antigen dependent manner.

CD40 is a costimulatory protein found on various antigen presenting cells which plays a role in their activation. The binding of CD40L (CD154) on $T_H$ cells to CD40 activates antigen presenting cells and induces a variety of downstream effects.

CD27 a T cell costimulatory molecule belonging to the TNF superfamily which plays a role in the generation and long-term maintenance of T cell immunity. It binds to a ligand CD70 in various immunological processes.

Additional costimulatory molecules that may be utilized in the present invention include, but are not limited to, HVEM, CD28, CD30, CD30L, CD40, CD70, LIGHT (CD258), B7-1, and B7-2.

As for the gp96-Ig fusions, the Ig portion ("tag") of the T cell costimulatory fusion protein can contain, a non-variable portion of an immunoglobulin molecule (e.g., an IgG1, IgG2, IgG3, IgG4, IgM, IgA, or IgE molecule). As described above, such portions typically contain at least functional CH2 and CH3 domains of the constant region of an immunoglobulin heavy chain. In some embodiments, a T cell costimulatory peptide can be fused to the hinge, CH2 and CH3 domains of murine IgG1 (Bowen et al., *J Immunol* 1996, 156:442-449). The Ig tag can be from a mammalian (e.g., human, mouse, monkey, or rat) immunoglobulin, but human immunoglobulin can be particularly useful when the fusion protein is intended for in vivo use for humans. Again, DNAs encoding immunoglobulin light or heavy chain constant regions are known or readily available from cDNA libraries. Various leader sequences as described above also can be used for secretion of T cell costimulatory fusion proteins from bacterial and mammalian cells.

A representative nucleotide optimized sequence (SEQ ID NO:4) encoding the extracellular domain of human ICOSL fused to Ig, and the amino acid sequence of the encoded fusion (SEQ ID NO:5) are provided:

```
                                        (SEQ ID NO: 4)
ATGAGACTGGGAAGCCCTGGCCTGCTGTTTCTGCTGTTCAG

CAGCCTGAGAGCCGACACCCAGGAAAAAGAAGTGCGGGC

CATGGTGGGAAGCGACGTGGAACTGAGCTGCGCCTGTCCT

GAGGGCAGCAGATTCGACCTGAACGACGTGTACGTGTACT

GGCAGACCAGCGAGAGCAAGACCGTCGTGACCTACCACAT

CCCCCAGAACAGCTCCCTGGAAAACGTGGACAGCCGGTAC

AGAAACCGGGCCCTGATGTCTCCTGCCGGCATGCTGAGAG

GCGACTTCAGCCTGCGGCTGTTCAACGTGACCCCCCAGGA

CGAGCAGAAATTCCACTGCCTGGTGCTGAGCCAGAGCCTG

GGCTTCCAGGAAGTGCTGAGCGTGGAAGTGACCCTGCACG

TGGCCGCCAATTTCAGCGTGCCAGTGGTGTCTGCCCCCCAC

AGCCCTTCTCAGGATGAGCTGACCTTCACCTGTACCAGCAT

CAACGGCTACCCCAGACCCAATGTGTACTGGATCAACAAG

ACCGACAACAGCCTGCTGGACCAGGCCCTGCAGAACGATA

CCGTGTTCCTGAACATGCGGGGCCTGTACGACGTGGTGTCC

GTGCTGAGAATCGCCAGAACCCCCAGCGTGAACATCGGCT

GCTGCATCGAGAACGTGCTGCTGCAGCAGAACCTGACCGT

GGGCAGCCAGACCGGCAACGACATCGGCGAGAGAGACAA
```

```
GATCACCGAGAACCCCGTGTCCACCGGCGAGAAGAATGCC
GCCACCTCTAAGTACGGCCCTCCCTGCCCTTCTTGCCCAGC
CCCTGAATTTCTGGGCGGACCCTCCGTGTTTCTGTTCCCCC
CAAAGCCCAAGGACACCCTGATGATCAGCCGGACCCCCGA
AGTGACCTGCGTGGTGGTGGATGTGTCCCAGGAAGATCCC
GAGGTGCAGTTCAATTGGTACGTGGACGGGGTGGAAGTGC
ACAACGCCAAGACCAAGCCCAGAGAGGAACAGTTCAACA
GCACCTACCGGGTGGTGTCTGTGCTGACCGTGCTGCACCAG
GATTGGCTGAGCGGCAAAGAGTACAAGTGCAAGGTGTCCA
GCAAGGGCCTGCCCAGCAGCATCGAAAAGACCATCAGCAA
CGCCACCGGCCAGCCCAGGGAACCCCAGGTGTACACACTG
CCCCCTAGCCAGGAAGAGATGACCAAGAACCAGGTGTCCC
TGACCTGTCTCGTGAAGGGCTTCTACCCCTCCGATATCGCC
GTGGAATGGGAGAGCAACGGCCAGCCAGAGAACAACTAC
AAGACCACCCCCCCAGTGCTGGACAGCGACGGCTCATTCT
TCCTGTACTCCCGGCTGACAGTGGACAAGAGCAGCTGGCA
GGAAGGCAACGTGTTCAGCTGCAGCGTGATGCACGAAGCC
CTGCACAACCACTACACCCAGAAGTCCCTGTCTCTGTCCCT
GGGCAAATGA
```

(SEQ ID NO: 5)
MRLGSPGLLFLLFSSLRADTQEKEVRAMVGSDVELSCACPEG
SRFDLNDVYVYWQTSESKTVVTYHIPQNSSLENVDSRYRNRA
LMSPAGMLRGDFSLRLFNVTPQDEQKFHCLVLSQSLGFQEVL
SVEVTLHVAANFSVPVVSAPHSPSQDELTFTCTSINGYPRPNV
YWINKTDNSLLDQALQNDTVFLNMRGLYDVVSVLRIARTPS
VNIGCCIENVLLQQNLTVGSQTGNDIGERDKITENPVSTGEKN
AATSKYGPPCPSCPAPEFLGGPSVFLFPPKPKDTLMISRTPEVT
CVVVDVSQEDPEVQFNWYVDGVEVHNAKTKPREEQFNSTYR
VVSVLTVLHQDWLSGKEYKCKVSSKGLPSSIEKTISNATGQPR
EPQVYTLPPSQEEMTKNQVSLTCLVKGFYPSDIAVEWESNGQ
PENNYKTTPPVLDSDGSFFLYSRLTVDKSSWQEGNVFSCSVM
HEALHNHYTQKSLSLSLGK.

A representative nucleotide optimized sequence (SEQ ID NO:6) encoding the extracellular domain of human 4-1BBL fused to Ig, and the encoded amino acid sequence (SEQ ID NO:7) are provided:

```
                                    (SEQ ID NO: 6)
ATGTCTAAGTACGGCCCTCCCTGCCCTAGCTGCCCTGCCCC
TGAATTTCTGGGCGGACCCAGCGTGTTCCTGTTCCCCCCAA
AGCCCAAGGACACCCTGATGATCAGCCGGACCCCCGAAGT
GACCTGCGTGGTGGTGGATGTGTCCCAGGAAGATCCCGAG
GTGCAGTTCAATTGGTACGTGGACGGCGTGGAAGTGCACA
ACGCCAAGACCAAGCCCAGAGAGGAACAGTTCAACAGCA
CCTACCGGGTGGTGTCCGTGCTGACCGTGCTGCACCAGGAT
TGGCTGAGCGGCAAAGAGTACAAGTGCAAGGTGTCCAGCA
AGGGCCTGCCCAGCAGCATCGAGAAAACCATCAGCAACGC
CACCGGCCAGCCCAGGGAACCCCAGGTGTACACACTGCCC
CCTAGCCAGGAAGAGATGACCAAGAACCAGGTGTCCCTGA
CCTGTCTCGTGAAGGGCTTCTACCCCTCCGATATCGCCGTG
GAATGGGAGAGCAACGGCCAGCCTGAGAACAACTACAAG
ACCACCCCCCCAGTGCTGGACAGCGACGGCTCATTCTTCCT
GTACAGCAGACTGACCGTGGACAAGAGCAGCTGGCAGGA
AGGCAACGTGTTCAGCTGCAGCGTGATGCACGAGGCCCTG
CACAACCACTACACCCAGAAGTCCCTGTCTCTGAGCCTGG
GCAAGGCCTGTCCATGGGCTGTGTCTGGCGCTAGAGCCTCT
CCTGGATCTGCCGCCAGCCCCAGACTGAGAGAGGGACCTG
AGCTGAGCCCCGATGATCCTGCCGGACTGCTGGATCTGAG
ACAGGGCATGTTCGCCCAGCTGGTGGCCCAGAACGTGCTG
CTGATCGATGGCCCCCTGAGCTGGTACAGCGATCCTGGACT
GGCTGGCGTGTCACTGACAGGCGGCCTGAGCTACAAAGAG
GACACCAAAGAACTGGTGGTGGCCAAGGCCGGCGTGTACT
ACGTGTTCTTTCAGCTGGAACTGCGGAGAGTGGTGGCCGG
CGAAGGATCCGGCTCTGTGTCTCTGGCTCTGCATCTGCAGC
CCCTGAGATCTGCTGCTGGCGCTGCTGCTCTGGCCCTGACA
GTGGACCTGCCTCCTGCCTCTAGCGAGGCCAGAAACAGCG
CATTCGGGTTTCAAGGCAGACTGCTGCACCTGTCTGCCGGC
CAGAGACTGGGAGTGCATCTGCACACAGAGGCCAGAGCCA
GGCACGCCTGGCAGCTGACTCAGGGCGCTACAGTGCTGGG
CCTGTTCAGAGTGACCCCCGAGATTCCAGCCGGCCTGCCTA
GCCCCAGATCCGAATGA
```

(SEQ ID NO: 7)
MSKYGPPCPSCPAPEFLGGPSVFLFPPKPKDTLMISRTPEVTCV
VVDVSQEDPEVQFNWYVDGVEVHNAKTKPREEQFNSTYRV
VSVLTVLHQDWLSGKEYKCKVSSKGLPSSIEKTISNATGQPRE
PQVYTLPPSQEEMTKNQVSLTCLVKGFYPSDIAVEWESNGQP
ENNYKTTPPVLDSDGSFFLYSRLTVDKSSWQEGNVFSCSVMH
EALHNHYTQKSLSLSLGKACPWAVSGARASPGSAASPRLREG
PELSPDDPAGLLDLRQGMFAQLVAQNVLLIDGPLSWYSDPGL
AGVSLTGGLSYKEDTKELVVAKAGVYYVFFQLELRRVVAGE
GSGSVSLALHLQPLRSAAGAAALALTVDLPPASSEARNSAFG
FQGRLLHLSAGQRLGVHLHTEARARHAWQLTQGATVLGLFR
VTPEIPAGLPSPRSE.

A representative nucleotide optimized sequence (SEQ ID NO:8) encoding the extracellular domain of human TL1A fused to Ig, and the encoded amino acid sequence (SEQ ID NO:9) are provided:

```
                                          (SEQ ID NO: 8)
ATGTCTAAGTACGGCCCTCCCTGCCCTAGCTGCCCTGCCCC
TGAATTTCTGGGCGGACCCAGCGTGTTCCTGTTCCCCCCAA
AGCCCAAGGACACCCTGATGATCAGCCGGACCCCCGAAGT
GACCTGCGTGGTGGTGGATGTGTCCCAGGAAGATCCCGAG
GTGCAGTTCAATTGGTACGTGGACGGCGTGGAAGTGCACA
ACGCCAAGACCAAGCCCAGAGAGGAACAGTTCAACAGCA
CCTACCGGGTGGTGTCCGTGCTGACCGTGCTGCACCAGGAT
TGGCTGAGCGGCAAAGAGTACAAGTGCAAGGTGTCCAGCA
AGGGCCTGCCCAGCAGCATCGAGAAAACCATCAGCAACGC
CACCGGCCAGCCCAGGGAACCCCAGGTGTACACACTGCCC
CCTAGCCAGGAAGAGATGACCAAGAACCAGGTGTCCCTGA
CCTGTCTCGTGAAGGGCTTCTACCCCTCCGATATCGCCGTG
GAATGGGAGAGCAACGGCCAGCCTGAGAACAACTACAAG
ACCACCCCCCAGTGCTGGACAGCGACGGCTCATTCTTCCT
GTACAGCAGACTGACCGTGGACAAGAGCAGCTGGCAGGA
AGGCAACGTGTTCAGCTGCAGCGTGATGCACGAGGCCCTG
CACAACCACTACACCCAGAAGTCCCTGTCTCTGAGCCTGG
GCAAGATCGAGGGCCGGATGGATAGAGCCCAGGGCGAAG
CCTGCGTGCAGTTCCAGGCTCTGAAGGGCCAGGAATTCGC
CCCCAGCCACCAGCAGGTGTACGCCCCTCTGAGAGCCGAC
GGCGATAAGCCTAGAGCCCACCTGACAGTCGTGCGGCAGA
CCCCTACCCAGCACTTCAAGAATCAGTTCCCCGCCCTGCAC
TGGGAGCACGAACTGGGCCTGGCCTTCACCAAGAACAGAA
TGAACTACACCAACAAGTTTCTGCTGATCCCCGAGAGCGG
CGACTACTTCATCTACAGCCAAGTGACCTTCCGGGGCATGA
CCAGCGAGTGCAGCGAGATCAGACAGGCCGGCAGACCTAA
CAAGCCCGACAGCATCACCGTCGTGATCACCAAAGTGACC
GACAGCTACCCCGAGCCCACCCAGCTGCTGATGGGCACCA
AGAGCGTGTGCGAAGTGGGCAGCAACTGGTTCCAGCCCAT
CTACCTGGGCGCCATGTTTAGTCTGCAAGAGGGCGACAAG
CTGATGGTCAACGTGTCCGACATCAGCCTGGTGGATTACAC
CAAAGAGGACAAGACCTTCTTCGGCGCCTTTCTGCTCTGA
                                          (SEQ ID NO: 9)
MSKYGPPCPSCPAPEFLGGPSVFLFPPKPKDTLMISRTPEVTCV
VVDVSQEDPEVQFNWYVDGVEVHNAKTKPREEQFNSTYRV
VSVLTVLHQDWLSGKEYKCKVSSKGLPSSIEKTISNATGQPRE
PQVYTLPPSQEEMTKNQVSLTCLVKGFYPSDIAVEWESNGQP
ENNYKTTPPVLDSDGSFFLYSRLTVDKSSWQEGNVFSCSVMH
EALHNHYTQKSLSLSLGKIEGRMDRAQGEACVQFQALKGQE
FAPSHQQVYAPLRADGDKPRAHLTVVRQTPTQHFKNQFPAL
HWEHELGLAFTKNRMNYTNKFLLIPESGDYFIYSQVTFRGMT
SECSEIRQAGRPNKPDSITVVITKVTDSYPEPTQLLMGTKSVCE
VGSNWFQPIYLGAMFSLQEGDKLMVNVSDISLVDYTKEDKTF
FGAFLL.
```

A representative nucleotide optimized sequence (SEQ ID NO:10) encoding human OX40L-Ig, and the encoded amino acid sequence (SEQ ID NO:11) are provided:

```
                                          (SEQ ID NO: 10)
ATGTCTAAGTACGGCCCTCCCTGCCCTAGCTGCCCTGCCCC
TGAATTTCTGGGCGGACCCAGCGTGTTCCTGTTCCCCCCAA
AGCCCAAGGACACCCTGATGATCAGCCGGACCCCCGAAGT
GACCTGCGTGGTGGTGGATGTGTCCCAGGAAGATCCCGAG
GTGCAGTTCAATTGGTACGTGGACGGCGTGGAAGTGCACA
ACGCCAAGACCAAGCCCAGAGAGGAACAGTTCAACAGCA
CCTACCGGGTGGTGTCCGTGCTGACCGTGCTGCACCAGGAT
TGGCTGAGCGGCAAAGAGTACAAGTGCAAGGTGTCCAGCA
AGGGCCTGCCCAGCAGCATCGAGAAAACCATCAGCAACGC
CACCGGCCAGCCCAGGGAACCCCAGGTGTACACACTGCCC
CCTAGCCAGGAAGAGATGACCAAGAACCAGGTGTCCCTGA
CCTGTCTCGTGAAGGGCTTCTACCCCTCCGATATCGCCGTG
GAATGGGAGAGCAACGGCCAGCCTGAGAACAACTACAAG
ACCACCCCCCAGTGCTGGACAGCGACGGCTCATTCTTCCT
GTACAGCAGACTGACCGTGGACAAGAGCAGCTGGCAGGA
AGGCAACGTGTTCAGCTGCAGCGTGATGCACGAGGCCCTG
CACAACCACTACACCCAGAAGTCCCTGTCTCTGAGCCTGG
GCAAGATCGAGGGCCGGATGGATCAGGTGTCACACAGATA
CCCCCGGATCCAGAGCATCAAAGTGCAGTTTACCGAGTAC
AAGAAAGAGAAGGGCTTTATCCTGACCAGCCAGAAAGAG
GACGAGATCATGAAGGTGCAGAACAACAGCGTGATCATCA
ACTGCGACGGGTTCTACCTGATCAGCCTGAAGGGCTACTTC
AGTCAGGAAGTGAACATCAGCCTGCACTACCAGAAGGACG
AGGAACCCCTGTTCCAGCTGAAGAAAGTGCGGAGCGTGAA
CAGCCTGATGGTGGCCTCTCTGACCTACAAGGACAAGGTG
TACCTGAACGTGACCACCGACAACACCAGCCTGGACGACT
TCCACGTGAACGGCGGCGAGCTGATCCTGATTCACCAGAA
CCCCGGCGAGTTCTGCGTGCTCTGA
                                          (SEQ ID NO: 11)
MSKYGPPCPSCPAPEFLGGPSVFLFPPKPKDTLMISRTPEVTCV
VVDVSQEDPEVQFNWYVDGVEVHNAKTKPREEQFNSTYRV
```

-continued
VSVLTVLHQDWLSGKEYKCKVSSKGLPSSIEKTISNATGQPRE

PQVYTLPPSQEEMTKNQVSLTCLVKGFYPSDIAVEWESNGQP

ENNYKTTPPVLDSDGSFFLYSRLTVDKSSWQEGNVFSCSVMH

EALHNHYTQKSLSLSLGKIEGRMDQVSHRYPRIQSIKVQFTEY

KKEKGFILTSQKEDEIMKVQNNSVIINCDGFYLISLKGYFSQEV

NISLHYQKDEEPLFQLKKVRSVNSLMVASLTYKDKVYLNVTT

DNTSLDDFHVNGGELILIHQNPGEFCVL.

Representative nucleotide and amino acid sequences for human TL1A are set forth in SEQ ID NO:12 and SEQ ID NO:13, respectively:

(SEQ ID NO: 12)
TCCCAAGTAGCTGGGACTACAGGAGCCCACCACCACCCC

GGCTAATTTTTTGTATTTTTAGTAGAGACGGGGTTTCACCG

TGTTAGCCAAGATGGTCTTGATCACCTGACCTCGTGATCCA

CCCGCCTTGGCCTCCCAAAGTGCTGGGATTACAGGCATGA

GCCACCGCGCCCGGCCTCCATTCAAGTCTTTATTGAATATC

TGCTATGTTCTACACACTGTTCTAGGTGCTGGGGATGCAAC

AGGGGACAAAATAGGCAAAATCCCTGTCCTTTTGGGGTTG

ACATTCTAGTGACTCTTCATGTAGTCTAGAAGAAGCTCAGT

GAATAGTGTCTGTGGTTGTTACCAGGGACACAATGACAGG

AACATTCTTGGGTAGAGTGAGAGGCCTGGGGAGGGAAGGG

TCTCTAGGATGGAGCAGATGCTGGGCAGTCTTAGGGAGCC

CCTCCTGGCATGCACCCCCTCATCCCTCAGGCCACCCCGT

CCCTTGCAGGAGCACCCTGGGGAGCTGTCCAGAGCGCTGT

GCCGCTGTCTGTGGCTGGAGGCAGAGTAGGTGGTGTGCTG

GGAATGCGAGTGGGAGAACTGGGATGGACCGAGGGGAGG

CGGGTGAGGAGGGGGGCAACCACCCAACACCCACCAGCTG

CTTTCAGTGTTCTGGGTCCAGGTGCTCCTGGCTGGCCTTGT

GGTCCCCCTCCTGCTTGGGGCCACCCTGACCTACACATACC

GCCACTGCTGGCCTCACAAGCCCCTGGTTACTGCAGATGA

AGCTGGGATGGAGGCTCTGACCCCACCACCGGCCACCCAT

CTGTCACCCTTGGACAGCGCCCACACCCTTCTAGCACCTCC

TGACAGCAGTGAGAAGATCTGCACCGTCCAGTTGGTGGGT

AACAGCTGGACCCCTGGCTACCCCGAGACCCAGGAGGCGC

TCTGCCCGCAGGTGACATGGTCCTGGGACCAGTTGCCCAG

CAGAGCTCTTGGCCCCGCTGCTGCGCCCACACTCTCGCCAG

AGTCCCCAGCCGGCTCGCCAGCCATGATGCTGCAGCCGGG

CCCGCAGCTCTACGACGTGATGGACGCGGTCCCAGCGCGG

CGCTGGAAGGAGTTCGTGCGCACGCTGGGGCTGCGCGAGG

CAGAGATCGAAGCCGTGGAGGTGGAGATCGGCCGCTTCCG

AGACCAGCAGTACGAGATGCTCAAGCGCTGGCGCCAGCAG

-continued
CAGCCCGCGGGCCTCGGAGCCGTTTACGCGGCCCTGGAGC

GCATGGGGCTGGACGGCTGCGTGGAAGACTTGCGCAGCCG

CCTGCAGCGCGGCCCGTGACACGGCGCCCACTTGCCACCT

AGGCGCTCTGGTGGCCCTTGCAGAAGCCCTAAGTACGGTT

ACTTATGCGTGTAGACATTTTATGTCACTTATTAAGCCGCT

GGCACGGCCCTGCGTAGCAGCACCAGCCGGCCCCACCCCT

GCTCGCCCCTATCGCTCCAGCCAAGGCGAAGAAGCACGAA

CGAATGTCGAGAGGGGGTGAAGACATTTCTCAACTTCTCG

GCCGGAGTTTGGCTGAGATCGCGGTATTAAATCTGTGAAA

GAAAACAAAACAAAACAA (SEQ ID NO: 13)
MEQRPRGCAAVAAALLLVLLGARAQGGTRSPRCDCAGDFHK

KIGLFCCRGCPAGHYLKAPCTEPCGNSTCLVCPQDTFLAWEN

HHNSECARCQACDEQASQVALENCSAVADTRCGCKPGWFVE

CQVSQCVSSSPFYCQPCLDCGALHRHTRLLCSRRDTDCGTCL

PGFYEHGDGCVSCPTPPPSLAGAPWGAVQSAVPLSVAGGRV

GVFWVQVLLAGLVVPLLLGATLTYTYRHCWPHKPLVTADEA

GMEALTPPPATHLSPLDSAHTLLAPPDSSEKICTVQLVGNSWT

PGYPETQEALCPQVTWSWDQLPSRALGPAAAPTLSPESPAGS

PAMMLQPGPQLYDVMDAVPARRWKEFVRTLGLREAEIEAVE

VEIGRFRDQQYEMLKRWRQQQPAGLGAVYAALERMGLDGC

VEDLRSRLQRGP.

Representative nucleotide and amino acid sequences for human HVEM are set forth in SEQ ID NO:38 (accession no. CR456909) and SEQ ID NO:39, respectively (accession no. CR456909):

(SEQ ID NO: 38)
ATGGAGCCTCCTGGAGACTGGGGGCCTCCTCCCTGGAGAT

CCACCCCCAAAACCGACGTCTTGAGGCTGGTGCTGTATCTC

ACCTTCCTGGGAGCCCCCTGCTACGCCCCAGCTCTGCCGTC

CTGCAAGGAGGACGAGTACCCAGTGGGCTCCGAGTGCTGC

CCCAAGTGCAGTCCAGGTTATCGTGTGAAGGAGGCCTGCG

GGGAGCTGACGGGCACAGTGTGAACCCTGCCCTCCAGG

CACCTACATTGCCCACCTCAATGGCCTAAGCAAGTGTCTGC

AGTGCCAAATGTGTGACCCAGCCATGGGCCTGCGCGCGAG

CCGGAACTGCTCCAGGACAGAGAACGCCGTGTGTGGCTGC

AGCCCAGGCCACTTCTGCATCGTCCAGGACGGGGACCACT

GCGCCGCGTGCCGCGCTTACGCCACCTCCAGCCCGGGCCA

GAGGGTGCAGAAGGGAGGCACCGAGAGTCAGGACACCCT

GTGTCAGAACTGCCCCCCGGGGACCTTCTCTCCCAATGGGA

CCCTGGAGGAATGTCAGCACCAGACCAAGTGCAGCTGGCT

GGTGACGAAGGCCGGAGCTGGGACCAGCAGCTCCCACTGG

GTATGGTGGTTTCTCTCAGGGAGCCTCGTCATCGTCATTGT

TTGCTCCACAGTTGGCCTAATCATATGTGTGAAAAGAAGA

AAGCCAAGGGGTGATGTAGTCAAGGTGATCGTCTCCGTCC

AGCGGAAAAGACAGGAGGCAGAAGGTGAGGCCACAGTCA

TTGAGGCCCTGCAGGCCCCTCCGGACGTCACCACGGTGGC

CGTGGAGGAGACAATACCCTCATTCACGGGGAGGAGCCCA

AACCATTAA (SEQ ID NO: 39)
MEPPGDWGPPPWRSTPKTDVLRLVLYLTFLGAPCYAPALPSC

KEDEYPVGSECCPKCSPGYRVKEACGELTGTVCEPCPPGTYIA

HLNGLSKCLQCQMCDPAMGLRASRNCSRTENAVCGCSPGHF

CIVQDGDHCAACRAYATSSPGQRVQKGGTESQDTLCQNCPP

GTFSPNGTLEECQHQTKCSWLVTKAGAGTSSSHWVWWFLSG

SLVIVIVCSTVGLIICVKRRKPRGDVVKVIVSVQRKRQEAEGE

ATVIEALQAPPDVTTVAVEETIPSFTGRSPNH.

Representative nucleotide and amino acid sequences for human CD28 are set forth in SEQ ID NO:40 (accession no. NM_006139) and SEQ ID NO:41, respectively:

(SEQ ID NO: 40)
TAAAGTCATCAAAACAACGTTATATCCTGTGTGAAATGCTG

CAGTCAGGATGCCTTGTGGTTTGAGTGCCTTGATCATGTGC

CCTAAGGGGATGGTGGCGGTGGTGGTGGCCGTGGATGACG

GAGACTCTCAGGCCTTGGCAGGTGCGTCTTTCAGTTCCCCT

CACACTTCGGGTTCCTCGGGGAGGAGGGGCTGGAACCCTA

GCCCATCGTCAGGACAAAGATGCTCAGGCTGCTCTTGGCTC

TCAACTTATTCCCTTCAATTCAAGTAACAGGAAACAAGATT

TTGGTGAAGCAGTCGCCCATGCTTGTAGCGTACGACAATG

CGGTCAACCTTAGCTGCAAGTATTCCTACAATCTCTTCTCA

AGGGAGTTCCGGGCATCCCTTCACAAAGGACTGGATAGTG

CTGTGGAAGTCTGTGTTGTATATGGGAATTACTCCCAGCAG

CTTCAGGTTTACTCAAAAACGGGGTTCAACTGTGATGGGA

AATTGGGCAATGAATCAGTGACATTCTACCTCCAGAATTTG

TATGTTAACCAAACAGATATTTACTTCTGCAAAATTGAAGT

TATGTATCCTCCTCCTTACCTAGACAATGAGAAGAGCAATG

GAACCATTATCCATGTGAAAGGGAAACACCTTTGTCCAAG

TCCCCTATTTCCCGGACCTTCTAAGCCCTTTTGGGTGCTGGT

GGTGGTTGGTGGAGTCCTGGCTTGCTATAGCTTGCTAGTAA

CAGTGGCCTTTATTATTTTCTGGGTGAGGAGTAAGAGGAGC

AGGCTCCTGCACAGTGACTACATGAACATGACTCCCCGCC

GCCCCGGGCCCACCCGCAAGCATTACCAGCCCTATGCCCC

ACCACGCGACTTCGCAGCCTATCGCTCCTGACACGGACGC

CTATCCAGAAGCCAGCCGGCTGGCAGCCCCCATCTGCTCA

ATATCACTGCTCTGGATAGGAAATGACCGCCATCTCCAGCC

GGCCACCTCAGGCCCCTGTTGGGCCACCAATGCCAATTTTT

CTCGAGTGACTAGACCAAATATCAAGATCATTTTGAGACTC

TGAAATGAAGTAAAAGAGATTTCCTGTGACAGGCCAAGTC

TTACAGTGCCATGGCCCACATTCCAACTTACCATGTACTTA

GTGACTTGACTGAGAAGTTAGGGTAGAAAACAAAAAGGG

AGTGGATTCTGGGAGCCTCTTCCCTTTCTCACTCACCTGCA

CATCTCAGTCAAGCAAAGTGTGGTATCCACAGACATTTTAG

TTGCAGAAGAAAGGCTAGGAAATCATTCCTTTTGGTTAAAT

GGGTGTTTAATCTTTTGGTTAGTGGGTTAAACGGGGTAAGT

TAGAGTAGGGGAGGGATAGGAAGACATATTTAAAAACC

ATTAAAACACTGTCTCCCACTCATGAAATGAGCCACGTAGT

TCCTATTTAATGCTGTTTTCCTTTAGTTTAGAAATACATAGA

CATTGTCTTTTATGAATTCTGATCATATTTAGTCATTTTGAC

CAAATGAGGGATTTGGTCAAATGAGGGATTCCCTCAAAGC

AATATCAGGTAAACCAAGTTGCTTTCCTCACTCCCTGTCAT

GAGACTTCAGTGTTAATGTTCACAATATACTTTCGAAAGAA

TAAAATAGTTCTCCTACATGAAGAAAGAATATGTCAGGAA

ATAAGGTCACTTTATGTCAAAATTATTTGAGTACTATGGGA

CCTGGCGCAGTGGCTCATGCTTGTAATCCCAGCACTTTGGG

AGGCCGAGGTGGGCAGATCACTTGAGATCAGGACCAGCCT

GGTCAAGATGGTGAAACTCCGTCTGTACTAAAAATACAAA

ATTTAGCTTGGCCTGGTGGCAGGCACCTGTAATCCCAGCTG

CCCAAGAGGCTGAGGCATGAGAATCGCTTGAACCTGGCAG

GCGGAGGTTGCAGTGAGCCGAGATAGTGCCACAGCTCTCC

AGCCTGGGCGACAGAGTGAGACTCCATCTCAAACAACAAC

AACAACAACAACAACAACAACAAACCACAAATTATTTGA

GTACTGTGAAGGATTATTTGTCTAACAGTTCATTCCAATCA

GACCAGGTAGGAGCTTTCCTGTTTCATATGTTTCAGGGTTG

CACAGTTGGTCTCTTTAATGTCGGTGTGGAGATCCAAAGTG

GGTTGTGGAAAGAGCGTCCATAGGAGAAGTGAGAATACTG

TGAAAAAGGGATGTTAGCATTCATTAGAGTATGAGGATGA

GTCCCAAGAAGGTCTTTGGAAGGAGGACGAATAGAATGG

AGTAATGAAATTCTTGCCATGTGCTGAGGAGATAGCCAGC

ATTAGGTGACAATCTTCCAGAAGTGGTCAGGCAGAAGGTG

CCCTGGTGAGAGCTCCTTTACAGGGACTTTATGTGGTTTAG

GGCTCAGAGCTCCAAAACTCTGGGCTCAGCTGCTCCTGTAC

CTTGGAGGTCCATTCACATGGGAAAGTATTTTGGAATGTGT

CTTTTGAAGAGAGCATCAGAGTTCTTAAGGGACTGGGTAA

GGCCTGACCCTGAAATGACCATGGATATTTTTCTACCTACA

-continued
GTTTGAGTCAACTAGAATATGCCTGGGGACCTTGAAGAAT
GGCCCTTCAGTGGCCCTCACCATTTGTTCATGCTTCAGTTA
ATTCAGGTGTTGAAGGAGCTTAGGTTTTAGAGGCACGTAG
ACTTGGTTCAAGTCTCGTTAGTAGTTGAATAGCCTCAGGCA
AGTCACTGCCCACCTAAGATGATGGTTCTTCAACTATAAAA
TGGAGATAATGGTTACAAATGTCTCTTCCTATAGTATAATC
TCCATAAGGGCATGGCCCAAGTCTGTCTTTGACTCTGCCTA
TCCCTGACATTTAGTAGCATGCCCGACATACAATGTTAGCT
ATTGGTATTATTGCCATATAGATAAATTATGTATAAAAATT
AAACTGGGCAATAGCCTAAGAAGGGGGGAATATTGTAACA
CAAATTTAAACCCACTACGCAGGGATGAGGTGCTATAATA
TGAGGACCTTTTAACTTCCATCATTTTCCTGTTTCTTGAAAT
AGTTTATCTTGTAATGAAATATAAGGCACCTCCCACTTTTA
TGTATAGAAAGAGGTCTTTTAATTTTTTTTAATGTGAGAA
GGAAGGGAGGAGTAGGAATCTTGAGATTCCAGATCGAAAA
TACTGTACTTTGGTTGATTTTTAAGTGGGCTTCCATTCCATG
GATTTAATCAGTCCCAAGAAGATCAAACTCAGCAGTACTT
GGGTGCTGAAGAACTGTTGGATTTACCCTGGCACGTGTGCC
ACTTGCCAGCTTCTTGGGCACACAGAGTTCTTCAATCCAAG
TTATCAGATTGTATTTGAAAATGACAGAGCTGGAGAGTTTT
TTGAAATGGCAGTGGCAAATAAATAAATACTTTTTTTTAAA
TGGAAAGACTTGATCTATGGTAATAAATGATTTTGTTTTCT
GACTGGAAAAATAGGCCTACTAAAGATGAATCACACTTGA
GATGTTTCTTACTCACTCTGCACAGAAACAAAGAAGAAAT
GTTATACAGGGAAGTCCGTTTTCACTATTAGTATGAACCAA
GAAATGGTTCAAAAACAGTGGTAGGAGCAATGCTTTCATA
GTTTCAGATATGGTAGTTATGAAGAAAACAATGTCATTTGC
TGCTATTATTGTAAGAGTCTTATAATTAATGGTACTCCTAT
AATTTTTGATTGTGAGCTCACCTATTTGGGTTAAGCATGCC
AATTTAAAGAGACCAAGTGTATGTACATTATGTTCTACATA
TTCAGTGATAAAATTACTAAACTACTATATGTCTGCTTTAA
ATTTGTACTTTAATATTGTCTTTTGGTATTAAGAAAGATAT
GCTTTCAGAATAGATATGCTTCGCTTTGGCAAGGAATTTGG
ATAGAACTTGCTATTTAAAAGAGGTGTGGGGTAAATCCTTG
TATAAATCTCCAGTTTAGCCTTTTTTGAAAAAGCTAGACTT
TCAAATACTAATTTCACTTCAAGCAGGGTACGTTTCTGGTT
TGTTTGCTTGACTTCAGTCACAATTTCTTATCAGACCAATG
GCTGACCTCTTTGAGATGTCAGGCTAGGCTTACCTATGTGT
TCTGTGTCATGTGAATGCTGAGAAGTTTGACAGAGATCCA
ACTTCAGCCTTGACCCCATCAGTCCCTCGGGTTAACTAACT
GAGCCACCGGTCCTCATGGCTATTTTAATGAGGGTATTGAT -continued
GGTTAAATGCATGTCTGATCCCTTATCCCAGCCATTTGCAC
TGCCAGCTGGGAACTATACCAGACCTGGATACTGATCCCA
AAGTGTTAAATTCAACTACATGCTGGAGATTAGAGATGGT
GCCAATAAAGGACCCAGAACCAGGATCTTGATTGCTATAG
ACTTATTAATAATCCAGGTCAAAGAGAGTGACACACACTC
TCTCAAGACCTGGGGTGAGGGAGTCTGTGTTATCTGCAAG
GCCATTTGAGGCTCAGAAAGTCTCTCTTTCCTATAGATATA
TGCATACTTTCTGACATATAGGAATGTATCAGGAATACTCA
ACCATCACAGGCATGTTCCTACCTCAGGGCCTTTACATGTC
CTGTTTACTCTGTCTAGAATGTCCTTCTGTAGATGACCTGG
CTTGCCTCGTCACCCTTCAGGTCCTTGCTCAAGTGTCATCTT
CTCCCCTAGTTAAACTACCCCACACCCTGTCTGCTTTCCTTG
CTTATTTTTCTCCATAGCATTTTACCATCTCTTACATTAGAC
ATTTTTCTTATTTATTTGTAGTTTATAAGCTTCATGAGGCAA
GTAACTTTGCTTTGTTTCTTGCTGTATCTCCAGTGCCCAGAG
CAGTGCCTGGTATATAATAAATATTTATTGACTGAGTGAAA
AAAAAAAAAAAAAA (SEQ ID NO: 41)
MLRLLLALNLFPSIQVTGNKILVKQSPMLVAYDNAVNLSCKY
SYNLFSREFRASLHKGLDSAVEVCVVYGNYSQQLQVYSKTGF
NCDGKLGNESVTFYLQNLYVNQTDIYFCKIEVMYPPPYLDNE
KSNGTIIHVKGKHLCPSPLFPGPSKPFWVLVVVGGVLACYSLL
VTVAFIIFWVRSKRSRLLHSDYMNMTPRRPGPTRKHYQPYAP
PRDFAAYRS.

Representative nucleotide and amino acid sequences for human CD30L are set forth in SEQ ID NO:42 (accession no. L09753) and SEQ ID NO:43, respectively:

(SEQ ID NO: 42)
CCAAGTCACATGATTCAGGATTCAGGGGGAGAATCCTTCTT
GGAACAGAGATGGGCCCAGAACTGAATCAGATGAAGAGA
GATAAGGTGTGATGTGGGGAAGACTATATAAAGAATGGAC
CCAGGGCTGCAGCAAGCACTCAACGGAATGGCCCCTCCTG
GAGACACAGCCATGCATGTGCCGGCGGGCTCCGTGGCCAG
CCACCTGGGGACCACGAGCCGCAGCTATTTCTATTTGACCA
CAGCCACTCTGGCTCTGTGCCTTGTCTTCACGGTGGCCACT
ATTATGGTGTTGGTCGTTCAGAGGACGGACTCCATTCCCAA
CTCACCTGACAACGTCCCCCTCAAAGGAGGAAATTGCTCA
GAAGACCTCTTATGTATCCTGAAAAGAGCTCCATTCAAGA
AGTCATGGGCCTACCTCCAAGTGGCAAAGCATCTAAACAA
AACCAAGTTGTCTTGGAACAAAGATGGCATTCTCCATGGA
GTCAGATATCAGGATGGGAATCTGGTGATCCAATTCCCTG

-continued
```
GTTTGTACTTCATCATTTGCCAACTGCAGTTTCTTGTACAAT
GCCCAAATAATTCTGTCGATCTGAAGTTGGAGCTTCTCATC
AACAAGCATATCAAAAACAGGCCCTGGTGACAGTGTGTG
AGTCTGGAATGCAAACGAAACACGTATACCAGAATCTCTC
TCAATTCTTGCTGGATTACCTGCAGGTCAACACCACCATAT
CAGTCAATGTGGATACATTCCAGTACATAGATACAAGCAC
CTTTCCTCTTGAGAATGTGTTGTCCATCTTCTTATACAGTAA
TTCAGACTGAACAGTTTCTCTTGGCCTTCAGGAAGAAAGCG
CCTCTCTACCATACAGTATTTCATCCCTCCAAACACTTGGG
CAAAAAGAAAACTTTAGACCAAGACAAACTACACAGGGTA
TTAAATAGTATACTTCTCCTTCTGTCTCTTGGAAAGATACA
GCTCCAGGGTTAAAAAGAGAGTTTTTAGTGAAGTATCTTTC
AGATAGCAGGCAGGGAAGCAATGTAGTGTGGTGGGCAGA
GCCCCACACAGAATCAGAAGGGATGAATGGATGTCCCAGC
CCAACCACTAATTCACTGTATGGTCTTGATCTATTTCTTCTG
TTTTGAGAGCCTCCAGTTAAAATGGGGCTTCAGTACCAGA
GCAGCTAGCAACTCTGCCCTAATGGGAAATGAAGGGGAGC
TGGGTGTGAGTGTTTACACTGTGCCCTTCACGGGATACTTC
TTTTATCTGCAGATGGCCTAATGCTTAGTTGTCCAAGTCGC
GATCAAGGACTCTCTCACACAGGAAACTTCCCTATACTGGC
AGATACACTTGTGACTGAACCATGCCCAGTTTATGCCTGTC
TGACTGTCACTCTGGCACTAGGAGGCTGATCTTGTACTCCA
TATGACCCCACCCCTAGGAACCCCCAGGGAAAACCAGGCT
CGGACAGCCCCCTGTTCCTGAGATGGAAAGCACAAATTTA
ATACACCACCACAATGGAAAACAAGTTCAAAGACTTTTAC
TTACAGATCCTGGACAGAAAGGGCATAATGAGTCTGAAGG
GCAGTCCTCCTTCTCCAGGTTACATGAGGCAGGAATAAGA
AGTCAGACAGAGACAGCAAGACAGTTAACAACGTAGGTA
AAGAAATAGGGTGTGGTCACTCTCAATTCACTGGCAAATG
CCTGAATGGTCTGTCTGAAGGAAGCAACAGAGAAGTGGGG
AATCCAGTCTGCTAGGCAGGAAAGATGCCTCTAAGTTCTTG
TCTCTGGCCAGAGGTGTGGTATAGAACCAGAAACCCATAT
CAAGGGTGACTAAGCCCGGCTTCCGGTATGAGAAATTAAA
CTTGTATACAAAATGGTTGCCAAGGCAACATAAAATTATA
AGAATTC
```
(SEQ ID NO: 43)
```
MDPGLQQALNGMAPPGDTAMHVPAGSVASHLGTTSRSYFYL
TTATLALCLVFTVATIMVLVVQRTDSIPNSPDNVPLKGGNCSE
DLLCILKRAPFKKSWAYLQVAKHLNKTKLSWNKDGILHGVR
YQDGNLVIQFPGLYFIICQLQFLVQCPNNSVDLKLELLINKHIK
KQALVTVCESGMQTKHVYQNLSQFLLDYLQVNTTISVNVDT
FQYIDTSTFPLENVLSIFLYSNSD.
```

Representative nucleotide and amino acid sequences for human CD40 are set forth in SEQ ID NO:44 (accession no. NM_001250) and SEQ ID NO:45, respectively:

(SEQ ID NO: 44)
```
TTTCCTGGGCGGGGCCAAGGCTGGGGCAGGGGAGTCAGCA
GAGGCCTCGCTCGGGCGCCCAGTGGTCCTGCCGCCTGGTCT
CACCTCGCTATGGTTCGTCTGCCTCTGCAGTGCGTCCTCTG
GGGCTGCTTGCTGACCGCTGTCCATCCAGAACCACCCACTG
CATGCAGAGAAAACAGTACCTAATAAACAGTCAGTGCTG
TTCTTTGTGCCAGCCAGGACAGAAACTGGTGAGTGACTGC
ACAGAGTTCACTGAAACGGAATGCCTTCCTTGCGGTGAAA
GCGAATTCCTAGACACCTGGAACAGAGAGACACACTGCCA
CCAGCACAAATACTGCGACCCCAACCTAGGGCTTCGGGTC
CAGCAGAAGGGCACCTCAGAAACAGACACCATCTGCACCT
GTGAAGAAGGCTGGCACTGTACGAGTGAGGCCTGTGAGAG
CTGTGTCCTGCACCGCTCATGCTCGCCCGGCTTTGGGGTCA
AGCAGATTGCTACAGGGGTTTCTGATACCATCTGCGAGCCC
TGCCCAGTCGGCTTCTTCTCCAATGTGTCATCTGCTTTCGA
AAAATGTCACCCTTGGACAAGCTGTGAGACCAAAGACCTG
GTTGTGCAACAGGCAGGCACAAACAAGACTGATGTTGTCT
GTGGTCCCCAGGATCGGCTGAGAGCCCTGGTGGTGATCCC
CATCATCTTCGGGATCCTGTTTGCCATCCTCTTGGTGCTGGT
CTTTATCAAAAAGGTGGCCAAGAAGCCAACCAATAAGGCC
CCCCACCCCAAGCAGGAACCCCAGGAGATCAATTTTCCCG
ACGATCTTCCTGGCTCCAACACTGCTGCTCCAGTGCAGGAG
ACTTTACATGGATGCAACCGGTCACCCAGGAGGATGGCA
AAGAGAGTCGCATCTCAGTGCAGGAGAGACAGTGAGGCTG
CACCCACCCAGGAGTGTGGCCACGTGGGCAAACAGGCAGT
TGGCCAGAGAGCCTGGTGCTGCTGCTGCTGTGGCGTGAGG
GTGAGGGGCTGGCACTGACTGGGCATAGCTCCCCGCTTCT
GCCTGCACCCCTGCAGTTTGAGACAGGAGACCTGGCACTG
GATGCAGAAACAGTTCACCTTGAAGAACCTCTCACTTCACC
CTGGAGCCCATCCAGTCTCCCAACTTGTATTAAAGACAGA
GGCAGAAGTTTGGTGGTGGTGGTGTTGGGGTATGGTTTAGT
AATATCCACCAGACCTTCCGATCCAGCAGTTTGGTGCCCAG
AGAGGCATCATGGTGGCTTCCCTGCGCCCAGGAAGCCATA
TACACAGATGCCCATTGCAGCATTGTTTGTGATAGTGAACA
ACTGGAAGCTGCTTAACTGTCCATCAGCAGGAGACTGGCT
AAATAAAATTAGAATATATTTATACAACAGAATCTCAAAA
```

```
ACACTGTTGAGTAAGGAAAAAAAGGCATGCTGCTGAATGA
TGGGTATGGAACTTTTTAAAAAAGTACATGCTTTTATGTAT
GTATATTGCCTATGGATATATGTATAAATACAATATGCATC
ATATATTGATATAACAAGGGTTCTGGAAGGGTACACAGAA
AACCCACAGCTCGAAGAGTGGTGACGTCTGGGGTGGGGAA
GAAGGGTCTGGGGG
```

(SEQ ID NO: 45)
MVRLPLQCVLWGCLLTAVHPEPPTACREKQYLINSQCCSLCQ
PGQKLVSDCTEFTETECLPCGESEFLDTWNRETHCHQHKYCD
PNLGLRVQQKGTSETDTICTCEEGWHCTSEACESCVLHRSCSP
GFGVKQIATGVSDTICEPCPVGFFSNVSSAFEKCHPWTSCETK
DLVVQQAGTNKTDVVCGPQDRLRALVVIPIIFGILFAILLVLVF
IKKVAKKPTNKAPHPKQEPQEINFPDDLPGSNTAAPVQETLHG
CQPVTQEDGKESRISVQERQ.

Representative nucleotide and amino acid sequences for human CD70 are set forth in SEQ ID NO:46 (accession no. NM_001252) and SEQ ID NO:47, respectively:

```
                                    (SEQ ID NO: 46)
CCAGAGAGGGGCAGGCTGGTCCCCTGACAGGTTGAAGCAA
GTAGACGCCCAGGAGCCCCGGGAGGGGGCTGCAGTTTCCT
TCCTTCCTTCTCGGCAGCGCTCCGCGCCCCCATCGCCCCTC
CTGCGCTAGCGGAGGTGATCGCCGCGGCGATGCCGGAGGA
GGGTTCGGGCTGCTCGGTGCGGCGCAGGCCCTATGGGTGC
GTCCTGCGGGCTGCTTTGGTCCCATTGGTCGCGGGCTTGGT
GATCTGCCTCGTGGTGTGCATCCAGCGCTTCGCACAGGCTC
AGCAGCAGCTGCCGCTCGAGTCACTTGGGTGGGACGTAGC
TGAGCTGCAGCTGAATCACACAGGACCTCAGCAGGACCCC
AGGCTATACTGGCAGGGGGGCCCAGCACTGGGCCGCTCCT
TCCTGCATGGACCAGAGCTGGACAAGGGGCAGCTACGTAT
CCATCGTGATGGCATCTACATGGTACACATCCAGGTGACG
CTGGCCATCTGCTCCTCCACGACGGCCTCCAGGCACCACCC
CACCACCCTGGCCGTGGGAATCTGCTCTCCCGCCTCCCGTA
GCATCAGCCTGCTGCGTCTCAGCTTCCACCAAGGTTGTACC
ATTGCCTCCCAGCGCCTGACGCCCCTGGCCCGAGGGGACA
CACTCTGCACCAACCTCACTGGGACACTTTTGCCTTCCCGA
AACACTGATGAGACCTTCTTTGGAGTGCAGTGGGTGCGCC
CCTGACCACTGCTGCTGATTAGGGTTTTTTAAATTTTATTTT
ATTTTATTTAAGTTCAAGAGAAAAAGTGTACACACAGGGG
CCACCCGGGGTTGGGGTGGGAGTGTGGTGGGGGGTAGTGG
TGGCAGGACAAGAGAAGGCATTGAGCTTTTTCTTTCATTTT
CCTATTAAAAAATACAAAAATCA
```

```
                                    (SEQ ID NO: 47)
MPEEGSGCSVRRRPYGCVLRAALVPLVAGLVICLVVCIQRFA
QAQQQLPLESLGWDVAELQLNHTGPQQDPRLYWQGGPALG
RSFLHGPELDKGQLRIHRDGIYMVHIQVTLAICSSTTASRHHP
TTLAVGICSPASRSISLLRLSFHQGCTIASQRLTPLARGDTLCT
NLTGTLLPSRNTDETFFGVQWVRP.
```

Representative nucleotide and amino acid sequences for human LIGHT are set forth in SEQ ID NO:48 (accession no. CR541854) and SEQ ID NO:49, respectively:

```
                                    (SEQ ID NO: 48)
ATGGAGGAGAGTGTCGTACGGCCCTCAGTGTTTGTGGTGG
ATGGACAGACCGACATCCCATTCACGAGGCTGGGACGAAG
CCACCGGAGACAGTCGTGCAGTGTGGCCCGGGTGGGTCTG
GGTCTCTTGCTGTTGCTGATGGGGCCGGGCTGGCCGTCCA
AGGCTGGTTCCTCCTGCAGCTGCACTGGCGTCTAGGAGAG
ATGGTCACCCGCCTGCCTGACGGACCTGCAGGCTCCTGGG
AGCAGCTGATACAAGAGCGAAGGTCTCACGAGGTCAACCC
AGCAGCGCATCTCACAGGGGCCAACTCCAGCTTGACCGGC
AGCGGGGGCCGCTGTTATGGGAGACTCAGCTGGGCCTGG
CCTTCCTGAGGGGCCTCAGCTACCACGATGGGGCCCTTGTG
GTCACCAAAGCTGGCTACTACTACATCTACTCCAAGGTGCA
GCTGGGCGGTGTGGGCTGCCCGCTGGGCCTGGCCAGCACC
ATCACCCACGGCCTCTACAAGCGCACACCCCGCTACCCCG
AGGAGCTGGAGCTGTTGGTCAGCCAGCAGTCACCCTGCGG
ACGGGCCACCAGCAGCTCCCGGGTCTGGTGGGACAGCAGC
TTCCTGGGTGGTGTGGTACACCTGGAGGCTGGGGAGGAGG
TGGTCGTCCGTGTGCTGGATGAACGCCTGGTTCGACTGCGT
GATGGTACCCGGTCTTACTTCGGGGCTTTCATGGTGTGA
```

```
                                    (SEQ ID NO: 49)
MEESVVRPSVFVVDGQTDIPFTRLGRSHRRQSCSVARVGLGL
LLLLMGAGLAVQGWFLLQLHWRLGEMVTRLPDGPAGSWEQ
LIQERRSHEVNPAAHLTGANSSLTGSGGPLLWETQLGLAFLR
GLSYHDGALVVTKAGYYYIYSKVQLGGVGCPLGLASTITHGL
YKRTPRYPEELELLVSQQSPCGRATSSSRVWWDSSFLGGVVH
LEAGEEVVRVLDERLVRLRDGTRSYFGAFMV.
```

In various embodiments, the present invention provides for variants comprising any of the sequences described herein, for instance, a sequence having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with any of the sequences disclosed herein (for example, SEQ ID NOS: 1-13 and 38-49).

In various embodiments, the present invention provides for an amino acid sequence having one or more amino acid mutations relative any of the protein sequences described herein. In some embodiments, the one or more amino acid mutations may be independently selected from conservative or non-conservative substitutions, insertions, deletions, and truncations as described herein.

Checkpoint Blockade/Blockage of Tumor Immunosuppression

Some human tumors can be eliminated by a patient's immune system. For example, administration of a monoclonal antibody targeted to an immune "checkpoint" molecule can lead to complete response and tumor remission. A mode of action of such antibodies is through inhibition of an immune regulatory molecule that the tumors have co-opted as protection from an anti-tumor immune response. By inhibiting these "checkpoint" molecules (e.g., with an antagonistic antibody), a patient's CD8+ T cells may be allowed to proliferate and destroy tumor cells.

For example, administration of a monoclonal antibody targeted to by way of example, without limitation, CTLA-4 or PD-1 can lead to complete response and tumor remission. The mode of action of such antibodies is through inhibition of CTLA-4 or PD-1 that the tumors have co-opted as protection from an anti-tumor immune response. By inhibiting these "checkpoint" molecules (e.g., with an antagonistic antibody), a patient's CD8+ T cells may be allowed to proliferate and destroy tumor cells.

Thus, the vectors provided herein can be used in combination with one or more blocking antibodies targeted to an immune "checkpoint" molecule. For instance, in some embodiments, the vectors provided herein can be used in combination with one or more blocking antibodies targeted to a molecule such as CTLA-4 or PD-1. For example, the vectors provided herein may be used in combination with an agent that blocks, reduces and/or inhibits PD-1 and PD-L1 or PD-L2 and/or the binding of PD-1 with PD-L1 or PD-L2 (by way of non-limiting example, one or more of nivolumab (ONO-4538/BMS-936558, MDX1106, OPDIVO, BRISTOL MYERS SQUIBB), pembrolizumab (KEYTRUDA, Merck), pidilizumab (CT-011, CURE TECH), MK-3475 (MERCK), BMS 936559 (BRISTOL MYERS SQUIBB), MPDL328OA (ROCHE)). In an embodiment, the vectors provided herein may be used in combination with an agent that blocks, reduces and/or inhibits the activity of CTLA-4 and/or the binding of CTLA-4 with one or more receptors (e.g. CD80, CD86, AP2M1, SHP-2, and PPP2R5A). For instance, in some embodiments, the immune-modulating agent is an antibody such as, by way of non-limitation, ipilimumab (MDX-010, MDX-101, Yervoy, BMS) and/or tremelimumab (Pfizer). Blocking antibodies against these molecules can be obtained from, for example, Bristol Myers Squibb (New York, N.Y.), Merck (Kenilworth, N.J.), Medlmmune (Gaithersburg, Md.), and Pfizer (New York, N.Y.).

Further, the vectors provided herein can be used in combination with one or more blocking antibodies targeted to an immune "checkpoint" molecule such as for example, BTLA, HVEM, TIM3, GALS, LAG3, VISTA, KIR, 2B4, CD160 (also referred to as BY55), CGEN-15049, CHK 1 and CHK2 kinases, A2aR, CEACAM (e.g., CEACAM-1, CEACAM-3 and/or CEACAM-5), GITR, GITRL, galectin-9, CD244, CD160, TIGIT, SIRPα, ICOS, CD172a, and TMIGD2 and various B-7 family ligands (including, but are not limited to, B7-1, B7-2, B7-DC, B7-H1, B7-H2, B7-H3, B7-H4, B7-H5, B7-H6 and B7-H7).

Vectors and Host Cells

This document provides nucleic acid constructs that encode a vaccine protein fusion protein (e.g., a gp96-Ig fusion protein) and a T cell costimulatory fusion protein that can be expressed in prokaryotic and eukaryotic cells. For example, this document provides expression vectors (e.g., DNA- or RNA-based vectors) containing nucleotide sequences that encode a vaccine protein fusion (e.g., a gp96-Ig fusion) and a T cell costimulatory fusion protein (e.g., OX40L-Ig or a portion thereof that binds specifically to OX40, ICOSL-Ig or a portion thereof that binds specifically to ICOS, 4-1BBL-Ig, or a portion thereof that binds specifically to 4-1BBR, CD40L-Ig, or a portion thereof that binds specifically to CD40, CD70-Ig, or a portion thereof that binds specifically to CD27, TL1A-Ig or a portion thereof that binds specifically to TNFRSF25, or GITRL-Ig or a portion thereof that binds specifically to GITR). In addition, this document provides methods for making the vectors described herein, as well as methods for introducing the vectors into appropriate host cells for expression of the encoded polypeptides. In general, the methods provided herein include constructing nucleic acid sequences encoding a vaccine protein fusion protein (e.g., a gp96-Ig fusion protein) and a T cell costimulatory fusion protein, cloning the sequences encoding the fusion proteins into an expression vector. The expression vector can be introduced into host cells or incorporated into virus particles, either of which can be administered to a subject to, for example, treat cancer or infection. For example, gp96-Ig based vaccines can be generated to stimulate antigen specific immune responses against individual antigens expressed by simian immunodeficiency virus, human immunodeficiency virus, hepatitis C virus and malaria Immune responses to these vaccines may be enhanced through co-expression of a T cell costimulatory fusion protein by the 96-Ig vector.

cDNA or DNA sequences encoding a vaccine protein fusion (e.g., a gp96-Ig fusion) and a T cell costimulatory fusion protein can be obtained (and, if desired, modified) using conventional DNA cloning and mutagenesis methods, DNA amplification methods, and/or synthetic methods. In general, a sequence encoding a vaccine protein fusion protein (e.g., a gp96-Ig fusion protein) and/or a T cell costimulatory fusion protein can be inserted into a cloning vector for genetic modification and replication purposes prior to expression. Each coding sequence can be operably linked to a regulatory element, such as a promoter, for purposes of expressing the encoded protein in suitable host cells in vitro and in vivo.

Expression vectors can be introduced into host cells for producing secreted vaccine proteins (e.g., gp96-Ig) and T cell costimulatory fusion proteins. There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; natural polymer-based delivery vehicles, such as chitosan and gelatin; viral vectors are also suitable for in vivo transduction. In some situations it is desirable to provide a targeting agent, such as an antibody or ligand specific for a cell surface membrane protein. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990).

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), Flp (Broach, et al., Cell, 29:227-234, 1982), R (Matsuzaki, et al., J. Bacteriology, 172:610-618, 1990), cpC31 (see, e.g., Groth et al., J. Mol. Biol. 335:667-678, 2004), sleeping beauty, transposases of the mariner family (Plasterk et al., supra), and components for integrating viruses such as AAV, retroviruses, and antiviruses having components that provide for virus integration such as the LTR sequences of retroviruses or lentivirus and the ITR sequences of AAV (Kootstra et al., Ann. Rev. Pharm. Toxicol., 43:413-439, 2003).

Cells may be cultured in vitro or genetically engineered, for example. Host cells can be obtained from normal or affected subjects, including healthy humans, cancer patients, and patients with an infectious disease, private laboratory deposits, public culture collections such as the American Type Culture Collection, or from commercial suppliers.

Cells that can be used for production and secretion of gp96-Ig fusion proteins and T cell costimulatory fusion proteins in vivo include, without limitation, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, or granulocytes, various stem or progenitor cells, such as hematopoietic stem or progenitor cells (e.g., as obtained from bone marrow), umbilical cord blood, peripheral blood, fetal liver, etc., and tumor cells (e.g., human tumor cells). The choice of cell type depends on the type of tumor or infectious disease being treated or prevented, and can be determined by one of skill in the art.

Different host cells have characteristic and specific mechanisms for post-translational processing and modification of proteins. A host cell may be chosen which modifies and processes the expressed gene products in a specific fashion similar to the way the recipient processes its heat shock proteins (hsps). For the purpose of producing large amounts of gp96-Ig, it can be preferable that the type of host cell has been used for expression of heterologous genes, and is reasonably well characterized and developed for large-scale production processes. In some embodiments, the host cells are autologous to the patient to whom the present fusion or recombinant cells secreting the present fusion proteins are subsequently administered.

In some embodiments, an expression construct as provided herein can be introduced into an antigenic cell. As used herein, antigenic cells can include preneoplastic cells that are infected with a cancer-causing infectious agent, such as a virus, but that are not yet neoplastic, or antigenic cells that have been exposed to a mutagen or cancer-causing agent, such as a DNA-damaging agent or radiation, for example. Other cells that can be used are preneoplastic cells that are in transition from a normal to a neoplastic form as characterized by morphology or physiological or biochemical function.

Typically, the cancer cells and preneoplastic cells used in the methods provided herein are of mammalian origin Mammals contemplated include humans, companion animals (e.g., dogs and cats), livestock animals (e.g., sheep, cattle, goats, pigs and horses), laboratory animals (e.g., mice, rats and rabbits), and captive or free wild animals.

In some embodiments, cancer cells (e.g., human tumor cells) can be used in the methods described herein. The cancer cells provide antigenic peptides that become associated non-covalently with the expressed gp96-Ig fusion proteins. Cell lines derived from a preneoplastic lesion, cancer tissue, or cancer cells also can be used, provided that the cells of the cell line have at least one or more antigenic determinant in common with the antigens on the target cancer cells. Cancer tissues, cancer cells, cells infected with a cancer-causing agent, other preneoplastic cells, and cell lines of human origin can be used. Cancer cells excised from the patient to whom ultimately the fusion proteins ultimately are to be administered can be particularly useful, although allogeneic cells also can be used. In some embodiments, a cancer cell can be from an established tumor cell line such as, without limitation, an established non-small cell lung carcinoma (NSCLC), bladder cancer, melanoma, ovarian cancer, renal cell carcinoma, prostate carcinoma, sarcoma, breast carcinoma, squamous cell carcinoma, head and neck carcinoma, hepatocellular carcinoma, pancreatic carcinoma, or colon carcinoma cell line.

In various embodiments, the present fusion proteins allow for both the costimulation T cell and the presentation of various tumor cell antigens. For instance, in some embodiments, the present vaccine protein fusions (e.g., gp96 fusions) chaperone these various tumor antigens. In various embodiments, the tumor cells secrete a variety of antigens. Illustrative, but non-limiting, antigens that can be secreted are: MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, lmp-1, NA, EBV-encoded nuclear antigen (EBNA)-1, brain glycogen phosphorylase, SSX-1, SSX-2 (HOM-MEL-40), SSX-1, SSX-4, SSX-5, SCP-1 CT-7, c-erbB-2, CD19, CD20, CD22, CD30, CD33, CD37, CD56, CD70, CD74, CD138, AGS16, MUC1, GPNMB, Ep-CAM, PD-L1, PD-L2, PMSA, bladder cancer antigens such as ACTL8, ADAM22, ADAM23, ATAD2, ATAD2B, BIRC5, CASC5, CEP290, CEP55, CTAGE5, DCAF12, DDX5, FAM133A, IL13RA2, IMP3, KIAA0100, MAGEA11, MAGEA3, MAGEA6, MPHOSPH10, ODF2, ODF2L, OIP5, PBK, RQCD1, SPAG1, SPAG4, SPAG9, TMEFF1, TTK, and prostate cancer antigens such as PRAME, BIRC5, CEP55, ATAD2, ODF2, KIAA0100, SPAG9, GPATCH2, ATAD2B, CEP290, SPAG1, ODF2L, CTAGE5, DDX5, DCAF12, IMP3. In some embodiments, the antigens are human endogenous retroviral antigens. Illustrative antigens can also include antigens from human endogenous retroviruses which include, but are not limited to, epitopes derived from at least a portion of Gag, at least a portion of Tat, at least a portion of Rev, a least a portion of Nef, and at least a portion of gp160.

Further, in some embodiments, the present vaccine protein fusions (e.g., gp96 fusions) provide for an adjuvant effect that further allows the immune system of a patient, when used in the various methods described herein, to be activated against a disease of interest.

Both prokaryotic and eukaryotic vectors can be used for expression of the vaccine protein (e.g., gp96-Ig) and T cell costimulatory fusion proteins in the methods provided herein. Prokaryotic vectors include constructs based on $E.$ $coli$ sequences (see, e.g., Makrides, $Microbiol\ Rev$ 1996, 60:512-538). Non-limiting examples of regulatory regions that can be used for expression in $E.\ coli$ include lac, trp, lpp, phoA, recA, tac, T3, T7 and $\lambda P_L$. Non-limiting examples of prokaryotic expression vectors may include the λgt vector series such as λgt11 (Huynh et al., in "DNA Cloning Techniques, Vol. I: A Practical Approach," 1984, (D. Glover, ed.), pp. 49-78, IRL Press, Oxford), and the pET vector series (Studier et al., $Methods\ Enzymol$ 1990, 185:60-89). Prokaryotic host-vector systems cannot perform much of the post-translational processing of mammalian cells, however. Thus, eukaryotic host-vector systems may be particularly useful.

A variety of regulatory regions can be used for expression of the vaccine protein (e.g., gp96-Ig) and T cell costimulatory fusions in mammalian host cells. For example, the SV40 early and late promoters, the cytomegalovirus (CMV) immediate early promoter, and the Rous sarcoma virus long terminal repeat (RSV-LTR) promoter can be used. Inducible promoters that may be useful in mammalian cells include, without limitation, promoters associated with the metallothionein II gene, mouse mammary tumor virus glucocorticoid responsive long terminal repeats (MMTV-LTR), the n-interferon gene, and the hsp70 gene (see, Williams et al., $Cancer\ Res$ 1989, 49:2735-42; and Taylor et al., $Mol\ Cell$ $Biol$ 1990, 10:165-75). Heat shock promoters or stress promoters also may be advantageous for driving expression of the fusion proteins in recombinant host cells.

In an embodiment, the present invention contemplates the use of inducible promoters capable of effecting high level of expression transiently in response to a cue. Illustrative inducible expression control regions include those comprising an inducible promoter that is stimulated with a cue such as a small molecule chemical compound. Particular examples can be found, for example, in U.S. Pat. Nos. 5,989,910, 5,935,934, 6,015,709, and 6,004,941, each of which is incorporated herein by reference in its entirety.

Animal regulatory regions that exhibit tissue specificity and have been utilized in transgenic animals also can be used in tumor cells of a particular tissue type: the elastase I gene control region that is active in pancreatic acinar cells (Swift et al., $Cell$ 1984, 38:639-646; Ornitz et al., $Cold\ Spring$ $Harbor\ Symp\ Quant\ Biol$ 1986, 50:399-409; and MacDonald, $Hepatology$ 1987, 7:425-515); the insulin gene control region that is active in pancreatic beta cells (Hanahan, $Nature$ 1985, 315:115-122), the immunoglobulin gene control region that is active in lymphoid cells (Grosschedl et al., $Cell$ 1984, 38:647-658; Adames et al., $Nature$ 1985, 318: 533-538; and Alexander et al., $Mol\ Cell\ Biol$ 1987, 7:1436-1444), the mouse mammary tumor virus control region that is active in testicular, breast, lymphoid and mast cells (Leder et al., $Cell$ 1986, 45:485-495), the albumin gene control region that is active in liver (Pinkert et al., $Genes\ Devel,$ 1987, 1:268-276), the alpha-fetoprotein gene control region that is active in liver (Krumlauf et al., $Mol\ Cell\ Biol$ 1985, 5:1639-1648; and Hammer et al., $Science$ 1987, 235:53-58); the alpha 1-antitrypsin gene control region that is active in liver (Kelsey et al., $Genes\ Devel$ 1987, 1:161-171), the beta-globin gene control region that is active in myeloid cells (Mogram et al., $Nature$ 1985, 315:338-340; and Kollias et al., $Cell$ 1986, 46:89-94); the myelin basic protein gene control region that is active in oligodendrocyte cells in the brain (Readhead et al., $Cell$ 1987, 48:703-712); the myosin light chain-2 gene control region that is active in skeletal muscle (Sani, $Nature$ 1985, 314:283-286), and the gonadotropic releasing hormone gene control region that is active in the hypothalamus (Mason et al., $Science$ 1986, 234:1372-1378).

An expression vector also can include transcription enhancer elements, such as those found in SV40 virus, Hepatitis B virus, cytomegalovirus, immunoglobulin genes, metallothionein, and β-actin (see, Bittner et al., $Meth\ Enzymol$ 1987, 153:516-544; and Gorman, $Curr\ Op\ Biotechnol$ 1990, 1:36-47). In addition, an expression vector can contain sequences that permit maintenance and replication of the vector in more than one type of host cell, or integration of the vector into the host chromosome. Such sequences include, without limitation, to replication origins, autonomously replicating sequences (ARS), centromere DNA, and telomere DNA.

In addition, an expression vector can contain one or more selectable or screenable marker genes for initially isolating, identifying, or tracking host cells that contain DNA encoding fusion proteins as described herein. For long term, high yield production of gp96-Ig and T cell costimulatory fusion proteins, stable expression in mammalian cells can be useful. A number of selection systems can be used for mammalian cells. For example, the Herpes simplex virus thymidine kinase (Wigler et al., $Cell$ 1977, 11:223), hypoxanthine-guanine phosphoribosyltransferase (Szybalski and Szybalski, $Proc\ Natl\ Acad\ Sci\ USA$ 1962, 48:2026), and adenine phosphoribosyltransferase (Lowy et al., $Cell$ 1980, 22:817) genes can be employed in tk⁻, hgprf⁻, or aprf⁻ cells, respectively. In addition, antimetabolite resistance can be used as the basis of selection for dihydrofolate reductase (dhfr), which confers resistance to methotrexate (Wigler et al., $Proc\ Natl\ Acad\ Sci\ USA$ 1980, 77:3567; O'Hare et al., $Proc\ Natl\ Acad\ Sci\ USA$ 1981, 78:1527); gpt, which confers resistance to mycophenolic acid (Mulligan and Berg, $Proc$ $Natl\ Acad\ Sci\ USA$ 1981, 78:2072); neomycin phosphotransferase (neo), which confers resistance to the aminoglycoside G-418 (Colberre-Garapin et al., $J\ Mol\ Biol$ 1981, 150:1); and hygromycin phosphotransferase (hyg), which confers resistance to hygromycin (Santerre et al., *Gene* 1984, 30:147). Other selectable markers such as histidinol and Zeocin™ also can be used.

Useful mammalian host cells include, without limitation, cells derived from humans, monkeys, and rodents (see, for example, Kriegler in "Gene Transfer and Expression: A Laboratory Manual," 1990, New York, Freeman & Co.). These include monkey kidney cell lines transformed by SV40 (e.g., COS-7, ATCC CRL 1651); human embryonic kidney lines (e.g., 293, 293-EBNA, or 293 cells subcloned for growth in suspension culture, Graham et al., *J Gen Virol* 1977, 36:59); baby hamster kidney cells (e.g., BHK, ATCC CCL 10); Chinese hamster ovary-cells-DHFR (e.g., CHO, Urlaub and Chasin, *Proc Natl Acad Sci USA* 1980, 77:4216); mouse sertoli cells (Mather, *Biol Reprod* 1980, 23:243-251); mouse fibroblast cells (e.g., NIH-3T3), monkey kidney cells (e.g., CV1 ATCC CCL 70); African green monkey kidney cells. (e.g., VERO-76, ATCC CRL-1587); human cervical carcinoma cells (e.g., HELA, ATCC CCL 2); canine kidney cells (e.g., MDCK, ATCC CCL 34); buffalo rat liver cells (e.g., BRL 3A, ATCC CRL 1442); human lung cells (e.g., W138, ATCC CCL 75); human liver cells (e.g., Hep G2, HB 8065); and mouse mammary tumor cells (e.g., MMT 060562, ATCC CCL51). Illustrative cancer cell types for expressing the fusion proteins described herein include mouse fibroblast cell line, NIH3T3, mouse Lewis lung carcinoma cell line, LLC, mouse mastocytoma cell line, P815, mouse lymphoma cell line, EL4 and its ovalbumin transfectant, E.G7, mouse melanoma cell line, B16F10, mouse fibrosarcoma cell line, MC57, human small cell lung carcinoma cell lines, SCLC#2 and SCLC#7, human lung adenocarcinoma cell line, e.g., AD100, and human prostate cancer cell line, e.g., PC-3.

A number of viral-based expression systems also can be used with mammalian cells to produce gp96-Ig and T cell costimulatory fusion proteins. Vectors using DNA virus backbones have been derived from simian virus 40 (SV40) (Hamer et al., *Cell* 1979, 17:725), adenovirus (Van Doren et al., *Mol Cell Biol* 1984, 4:1653), adeno-associated virus (McLaughlin et al., *J Virol* 1988, 62:1963), and bovine papillomas virus (Zinn et al., *Proc Natl Acad Sci USA* 1982, 79:4897). When an adenovirus is used as an expression vector, the donor DNA sequence may be ligated to an adenovirus transcription/translation control complex, e.g., the late promoter and tripartite leader sequence. This fusion gene may then be inserted in the adenovirus genome by in vitro or in vivo recombination. Insertion in a non-essential region of the viral genome (e.g., region E1 or E3) can result in a recombinant virus that is viable and capable of expressing heterologous products in infected hosts. (See, e.g., Logan and Shenk, *Proc Natl Acad Sci USA* 1984, 81:3655-3659).

Bovine papillomavirus (BPV) can infect many higher vertebrates, including man, and its DNA replicates as an episome. A number of shuttle vectors have been developed for recombinant gene expression which exist as stable, multicopy (20-300 copies/cell) extrachromosomal elements in mammalian cells. Typically, these vectors contain a segment of BPV DNA (the entire genome or a 69% transforming fragment), a promoter with a broad host range, a polyadenylation signal, splice signals, a selectable marker, and "poisonless" plasmid sequences that allow the vector to be propagated in *E. coli*. Following construction and amplification in bacteria, the expression gene constructs are transfected into cultured mammalian cells by, for example, calcium phosphate coprecipitation. For those host cells that do not manifest a transformed phenotype, selection of transformants is achieved by use of a dominant selectable marker, such as histidinol and G418 resistance.

Alternatively, the vaccinia 7.5K promoter can be used. (See, e.g., Mackett et al., *Proc Natl Acad Sci USA* 1982, 79:7415-7419; Mackett et al., *J Virol* 1984, 49:857-864; and Panicali et al., *Proc Natl Acad Sci USA* 1982, 79:4927-4931.) In cases where a human host cell is used, vectors based on the Epstein-Barr virus (EBV) origin (OriP) and EBV nuclear antigen 1 (EBNA-1; a trans-acting replication factor) can be used. Such vectors can be used with a broad range of human host cells, e.g., EBO-pCD (Spickofsky et al., *DNA Prot Eng Tech* 1990, 2:14-18); pDR2 and λDR2 (available from Clontech Laboratories).

Gp96-Ig and T cell costimulatory fusion proteins also can be made with retrovirus-based expression systems. Retroviruses, such as Moloney murine leukemia virus, can be used since most of the viral gene sequence can be removed and replaced with exogenous coding sequence while the missing viral functions can be supplied in trans. In contrast to transfection, retroviruses can efficiently infect and transfer genes to a wide range of cell types including, for example, primary hematopoietic cells. Moreover, the host range for infection by a retroviral vector can be manipulated by the choice of envelope used for vector packaging.

For example, a retroviral vector can comprise a 5' long terminal repeat (LTR), a 3' LTR, a packaging signal, a bacterial origin of replication, and a selectable marker. The gp96-Ig fusion protein coding sequence, for example, can be inserted into a position between the 5' LTR and 3' LTR, such that transcription from the 5' LTR promoter transcribes the cloned DNA. The 5' LTR contains a promoter (e.g., an LTR promoter), an R region, a U5 region, and a primer binding site, in that order. Nucleotide sequences of these LTR elements are well known in the art. A heterologous promoter as well as multiple drug selection markers also can be included in the expression vector to facilitate selection of infected cells. See, McLauchlin et al., *Prog Nucleic Acid Res Mol Biol* 1990, 38:91-135; Morgenstern et al., *Nucleic Acid Res* 1990, 18:3587-3596; Choulika et al., *J Virol* 1996, 70:1792-1798; Boesen et al., *Biotherapy* 1994, 6:291-302; Salmons and Gunzberg, *Human Gene Ther* 1993, 4:129-141; and Grossman and Wilson, *Curr Opin Genet Devel* 1993, 3:110-114.

Any of the cloning and expression vectors described herein may be synthesized and assembled from known DNA sequences using techniques that are known in the art. The regulatory regions and enhancer elements can be of a variety of origins, both natural and synthetic. Some vectors and host cells may be obtained commercially. Non-limiting examples of useful vectors are described in Appendix 5 of *Current Protocols in Molecular Biology,* 1988, ed. Ausubel et al., Greene Publish. Assoc. & Wiley Interscience, which is incorporated herein by reference; and the catalogs of commercial suppliers such as Clontech Laboratories, Stratagene Inc., and Invitrogen, Inc.

Methods of Treating

An expression vector as provided herein can be incorporated into a composition for administration to a subject (e.g., a research animal or a mammal, such as a human, having a clinical condition such as cancer or an infection). For example, an expression vector can be administered to a subject for the treatment of cancer or infection. Thus, this document provides methods for treating clinical conditions such as cancer or infection with the expression vectors provided herein. The infection can be, for example, an acute infection or a chronic infection. In some embodiments, the infection can be an infection by hepatitis C virus, hepatitis B virus, human immunodeficiency virus, or malaria. The methods can include administering to a subject an expression vector, a cell containing the expression vector, or a virus or virus-like particle containing the expression vector, under conditions wherein the progression or a symptom of the clinical condition in the subject is reduced in a therapeutic manner.

In various embodiments, the present invention pertains to cancers and/or tumors; for example, the treatment or prevention of cancers and/or tumors. Cancers or tumors refer to an uncontrolled growth of cells and/or abnormal increased cell survival and/or inhibition of apoptosis which interferes with the normal functioning of the bodily organs and systems. Included are benign and malignant cancers, polyps, hyperplasia, as well as dormant tumors or micrometastases. Also, included are cells having abnormal proliferation that is not impeded by the immune system (e.g. virus infected cells). The cancer may be a primary cancer or a metastatic cancer. The primary cancer may be an area of cancer cells at an originating site that becomes clinically detectable, and may be a primary tumor. In contrast, the metastatic cancer may be the spread of a disease from one organ or part to another non-adjacent organ or part. The metastatic cancer may be caused by a cancer cell that acquires the ability to penetrate and infiltrate surrounding normal tissues in a local area, forming a new tumor, which may be a local metastasis. The cancer may also be caused by a cancer cell that acquires the ability to penetrate the walls of lymphatic and/or blood vessels, after which the cancer cell is able to circulate through the bloodstream (thereby being a circulating tumor cell) to other sites and tissues in the body. The cancer may be due to a process such as lymphatic or hematogeneous spread. The cancer may also be caused by a tumor cell that comes to rest at another site, re-penetrates through the vessel or walls, continues to multiply, and eventually forms another clinically detectable tumor. The cancer may be this new tumor, which may be a metastatic (or secondary) tumor.

The cancer may be caused by tumor cells that have metastasized, which may be a secondary or metastatic tumor. The cells of the tumor may be like those in the original tumor. As an example, if a breast cancer or colon cancer metastasizes to the liver, the secondary tumor, while present in the liver, is made up of abnormal breast or colon cells, not of abnormal liver cells. The tumor in the liver may thus be a metastatic breast cancer or a metastatic colon cancer, not liver cancer.

The cancer may have an origin from any tissue. The cancer may originate from melanoma, colon, breast, or prostate, and thus may be made up of cells that were originally skin, colon, breast, or prostate, respectively. The cancer may also be a hematological malignancy, which may be lymphoma. The cancer may invade a tissue such as liver, lung, bladder, or intestinal.

Illustrative cancers that may be treated include, but are not limited to, carcinomas, e.g. various subtypes, including, for example, adenocarcinoma, basal cell carcinoma, squamous cell carcinoma, and transitional cell carcinoma), sarcomas (including, for example, bone and soft tissue), leukemias (including, for example, acute myeloid, acute lymphoblastic, chronic myeloid, chronic lymphocytic, and hairy cell), lymphomas and myelomas (including, for example, Hodgkin and non-Hodgkin lymphomas, light chain, non-secretory, MGUS, and plasmacytomas), and central nervous system cancers (including, for example, brain (e.g. gliomas (e.g. astrocytoma, oligodendroglioma, and ependymoma), meningioma, pituitary adenoma, and neuromas, and spinal cord tumors (e.g. meningiomas and neurofibroma).

Representative cancers and/or tumors of the present invention include, but are not limited to, a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In some aspects, the present fusions are used to eliminate intracellular pathogens. In some aspects, the present fusions are used to treat one or more infections. In some embodiments, the present fusion proteins are used in methods of treating viral infections (including, for example, HIV and HCV), parasitic infections (including, for example, malaria), and bacterial infections. In various embodiments, the infections induce immunosuppression. For example, HIV infections often result in immunosuppression in the infected subjects. Accordingly, as described elsewhere herein, the treatment of such infections may involve, in various embodiments, modulating the immune system with the present fusion proteins to favor immune stimulation over immune inhibition. Alternatively, the present invention provides methods for treating infections that induce immunoactivation. For example, intestinal helminth infections have been associated with chronic immune activation. In these embodiments, the treatment of such infections may involve modulating the immune system with the present fusion proteins to favor immune inhibition over immune stimulation.

In various embodiments, the present invention provides methods of treating viral infections including, without limitation, acute or chronic viral infections, for example, of the respiratory tract, of papilloma virus infections, of herpes simplex virus (HSV) infection, of human immunodeficiency virus (HIV) infection, and of viral infection of internal organs such as infection with hepatitis viruses. In some embodiments, the viral infection is caused by a virus of family Flaviviridae. In some embodiments, the virus of family Flaviviridae is selected from Yellow Fever Virus, West Nile virus, Dengue virus, Japanese Encephalitis Virus, St. Louis Encephalitis Virus, and Hepatitis C Virus. In other embodiments, the viral infection is caused by a virus of family Picornaviridae, e.g., poliovirus, rhinovirus, coxsackievirus. In other embodiments, the viral infection is caused by a member of Orthomyxoviridae, e.g., an influenza virus. In other embodiments, the viral infection is caused by a member of Retroviridae, e.g., a lentivirus. In other embodiments, the viral infection is caused by a member of Paramyxoviridae, e.g., respiratory syncytial virus, a human parainfluenza virus, rubulavirus (e.g., mumps virus), measles virus, and human metapneumovirus. In other embodiments, the viral infection is caused by a member of Bunyaviridae, e.g., hantavirus. In other embodiments, the viral infection is caused by a member of Reoviridae, e.g., a rotavirus.

In various embodiments, the present invention provides methods of treating parasitic infections such as protozoan or helminths infections. In some embodiments, the parasitic infection is by a protozoan parasite. In some embodiments, the oritiziab parasite is selected from intestinal protozoa, tissue protozoa, or blood protozoa. Illustrative protozoan parasites include, but are not limited to, *Entamoeba hystolytica, Giardia lamblia, Cryptosporidium muris, Trypanosomatida gambiense, Trypanosomatida rhodesiense, Trypanosomatida crusi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Trichomonas vaginalis*, and *Histomonas meleagridis*. In some embodiments, the parasitic infection is by a helminthic parasite such as nematodes (e.g., Adenophorea). In some embodiments, the parasite is selected from Secementea (e.g., *Trichuris trichiura, Ascaris lumbricoides, Enterobius vermicularis, Ancylostoma duodenale, Necator americanus, Strongyloides stercoralis, Wuchereria bancrofti, Dracunculus medinensis*). In some embodiments, the parasite is selected from trematodes (e.g. blood flukes, liver flukes, intestinal flukes, and lung flukes). In some embodiments, the parasite is selected from: *Schistosoma mansoni, Schistosoma haematobium, Schistosoma japonicum, Fasciola hepatica, Fasciola gigantica, Heterophyes heterophyes, Paragonimus westermani*. In some embodiments, the parasite is selected from cestodes (e.g., *Taenia solium, Taenia saginata, Hymenolepis nana, Echinococcus granulosus*).

In various embodiments, the present invention provides methods of treating bacterial infections. In various embodiments, the bacterial infection is by a gram-positive bacteria, gram-negative bacteria, aerobic and/or anaerobic bacteria. In various embodiments, the bacteria is selected from, but not limited to, *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms. In some embodiments, the bacteria is selected from, but not limited to, *Pseudomonas aeruginosa, Pseudomonas fluorescens, Pseudomonas acidovorans, Pseudomonas alcaligenes, Pseudomonas pufida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceficus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*. The expression vector(s), cells, or particles to be administered can be admixed, encapsulated, conjugated or otherwise associated with other molecules, molecular structures, or mixtures of compounds such as, for example, liposomes, receptor or cell targeted molecules, or oral, topical or other formulations for assisting in uptake, distribution and/or absorption. In some cases, an expression vector can be contained within a cell that is administered to a subject, or contained within a virus or virus-like particle. The vector, cell, or particle to be administered can be in combination with a pharmaceutically acceptable carrier.

This document therefore also provides compositions containing a vector or a tumor cell or virus particle containing a vector encoding a secreted gp96-Ig fusion polypeptide and a T cell costimulatory fusion polypeptide as described herein, in combination with a physiologically and pharmaceutically acceptable carrier. The physiologically and pharmaceutically acceptable carrier can be include any of the well-known components useful for immunization. The carrier can facilitate or enhance an immune response to an antigen administered in a vaccine. The cell formulations can contain buffers to maintain a preferred pH range, salts or other components that present an antigen to an individual in a composition that stimulates an immune response to the antigen. The physiologically acceptable carrier also can contain one or more adjuvants that enhance the immune response to an antigen. Pharmaceutically acceptable carriers include, for example, pharmaceutically acceptable solvents, suspending agents, or any other pharmacologically inert vehicles for delivering compounds to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water, saline solution, binding agents (e.g., polyvinylpyrrolidone or hydroxypropyl methylcellulose); fillers (e.g., lactose or dextrose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Compositions can be formulated for subcutaneous, intramuscular, or intradermal administration, or in any manner acceptable for immunization.

An adjuvant refers to a substance which, when added to an immunogenic agent such as a tumor cell expressing secreted vaccine protein (e.g., gp96-Ig) and T cell costimulatory fusion polypeptides, nonspecifically enhances or potentiates an immune response to the agent in the recipient host upon exposure to the mixture. Adjuvants can include, for example, oil-in-water emulsions, water-in oil emulsions, alum (aluminum salts), liposomes and microparticles, such as, polysytrene, starch, polyphosphazene and polylactide/polyglycosides.

Adjuvants can also include, for example, squalene mixtures (SAF-I), muramyl peptide, saponin derivatives, *mycobacterium* cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al., *Nature* 1990, 344:873-875. For veterinary use and for production of antibodies in animals, mitogenic components of Freund's adjuvant (both complete and incomplete) can be used. In humans, Incomplete Freund's Adjuvant (IFA) is a useful adjuvant. Various appropriate adjuvants are well known in the art (see, for example, Warren and Chedid, *CRC Critical Reviews in Immunology* 1988, 8:83; and Allison and Byars, in Vaccines: New Approaches to Immunological Problems, 1992, Ellis, ed., Butterworth-Heinemann, Boston). Additional adjuvants include, for example, bacille Calmett-Guerin (BCG), DETOX (containing cell wall skeleton of *Mycobacterium phlei* (CWS) and monophosphoryl lipid A from *Salmonella minnesota* (MPL)), and the like (see, for example, Hoover et al., *J Clin Oncol* 1993, 11:390; and Woodlock et al., *J Immunother* 1999, 22:251-259).

In some embodiments, a vector can be administered to a subject one or more times (e.g., once, twice, two to four times, three to five times, five to eight times, six to ten times, eight to 12 times, or more than 12 times). A vector as provided herein can be administered one or more times per day, one or more times per week, every other week, one or more times per month, once every two to three months, once every three to six months, or once every six to 12 months. A vector can be administered over any suitable period of time, such as a period from about 1 day to about 12 months. In some embodiments, for example, the period of administration can be from about 1 day to 90 days; from about 1 day to 60 days; from about 1 day to 30 days; from about 1 day to 20 days; from about 1 day to 10 days; from about 1 day to 7 days. In some embodiments, the period of administration can be from about 1 week to 50 weeks; from about 1 week to 50 weeks; from about 1 week to 40 weeks; from about 1 week to 30 weeks; from about 1 week to 24 weeks; from about 1 week to 20 weeks; from about 1 week to 16 weeks; from about 1 week to 12 weeks; from about 1 week to 8 weeks; from about 1 week to 4 weeks; from about 1 week to 3 weeks; from about 1 week to 2 weeks; from about 2 weeks to 3 weeks; from about 2 weeks to 4 weeks; from about 2 weeks to 6 weeks; from about 2 weeks to 8 weeks; from about 3 weeks to 8 weeks; from about 3 weeks to 12 weeks; or from about 4 weeks to 20 weeks.

In some embodiments, after an initial dose (sometimes referred to as a "priming" dose) of a vector has been administered and a maximal antigen-specific immune response has been achieved, one or more boosting doses of a vector as provided herein can be administered. For example, a boosting dose can be administered about 10 to 30 days, about 15 to 35 days, about 20 to 40 days, about 25 to 45 days, or about 30 to 50 days after a priming dose.

In some embodiments, the methods provided herein can be used for controlling solid tumor growth (e.g., breast, prostate, melanoma, renal, colon, or cervical tumor growth) and/or metastasis. The methods can include administering an effective amount of an expression vector as described herein to a subject in need thereof. In some embodiments, the subject is a mammal (e.g., a human).

The vectors and methods provided herein can be useful for stimulating an immune response against a tumor. Such immune response is useful in treating or alleviating a sign or symptom associated with the tumor. As used herein, by "treating" is meant reducing, preventing, and/or reversing the symptoms in the individual to which a vector as described herein has been administered, as compared to the symptoms of an individual not being treated. A practitioner will appreciate that the methods described herein are to be used in concomitance with continuous clinical evaluations by a skilled practitioner (physician or veterinarian) to determine subsequent therapy. Such evaluations will aid and inform in evaluating whether to increase, reduce, or continue a particular treatment dose, mode of administration, etc.

The methods provided herein can thus be used to treat a tumor, including, for example, a cancer. The methods can be used, for example, to inhibit the growth of a tumor by preventing further tumor growth, by slowing tumor growth, or by causing tumor regression. Thus, the methods can be used, for example, to treat a cancer such as a lung cancer. It will be understood that the subject to which a compound is administered need not suffer from a specific traumatic state. Indeed, the vectors described herein may be administered prophylactically, prior to development of symptoms (e.g., a patient in remission from cancer). The terms "therapeutic" and "therapeutically," and permutations of these terms, are used to encompass therapeutic, palliative, and prophylactic uses. Thus, as used herein, by "treating or alleviating the symptoms" is meant reducing, preventing, and/or reversing the symptoms of the individual to which a therapeutically effective amount of a composition has been administered, as compared to the symptoms of an individual receiving no such administration.

As used herein, the terms "effective amount" and "therapeutically effective amount" refer to an amount sufficient to provide the desired therapeutic (e.g., anti-cancer, anti-tumor, or anti-infection) effect in a subject (e.g., a human diagnosed as having cancer or an infection). Anti-tumor and anti-cancer effects include, without limitation, modulation of tumor growth (e.g., tumor growth delay), tumor size, or metastasis, the reduction of toxicity and side effects associated with a particular anti-cancer agent, the amelioration or minimization of the clinical impairment or symptoms of cancer, extending the survival of the subject beyond that which would otherwise be expected in the absence of such treatment, and the prevention of tumor growth in an animal lacking tumor formation prior to administration, i.e., prophylactic administration. In some embodiments, administration of an effective amount of a vector or a composition, cell, or virus particle containing the vector can increase the activation or proliferation of tumor antigen specific T cells in a subject. For example, the activation or proliferation of tumor antigen specific T cells in the subject can be is increased by at least 10 percent (e.g., at least 25 percent, at least 50 percent, or at least 75 percent) as compared to the level of activation or proliferation of tumor antigen specific T cells in the subject prior to the administration.

Anti-infection effects include, for example, a reduction in the number of infective agents (e.g., viruses or bacteria). When the clinical condition in the subject to be treated is an infection, administration of a vector as provided herein can stimulate the activation or proliferation of pathogenic antigen specific T cells in the subject. For example, administration of the vector can lead to activation of antigen-specific T cells in the subject to a level great than that achieved by 96-Ig vaccination alone.

One of skill will appreciate that an effective amount of a vector may be lowered or increased by fine tuning and/or by administering more than one dose (e.g., by concomitant administration of two different genetically modified tumor cells containing the vector), or by administering a vector with another agent (e.g., an antagonist of PD-1) to enhance the therapeutic effect (e.g., synergistically). This document therefore provides a method for tailoring the administration/treatment to the particular exigencies specific to a given mammal. Therapeutically effective amounts can be determined by, for example, starting at relatively low amounts and using step-wise increments with concurrent evaluation of beneficial effects. The methods provided herein thus can be used alone or in combination with other well-known tumor therapies, to treat a patient having a tumor. One skilled in the art will readily understand advantageous uses of the vectors and methods provided herein, for example, in prolonging the life expectancy of a cancer patient and/or improving the quality of life of a cancer patient (e.g., a lung cancer patient).

Combination Therapies and Conjugation

In some embodiments, the invention provides for methods that further comprise administering an additional agent to a subject. In some embodiments, the invention pertains to co-administration and/or co-formulation.

In some embodiments, administration of vaccine protein (e.g., gp96-Ig) and one or more costimulatory molecules act synergistically when co-administered with another agent and is administered at doses that are lower than the doses commonly employed when such agents are used as monotherapy.

In some embodiments, inclusive of, without limitation, cancer applications, the present invention pertains to chemotherapeutic agents as additional agents. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomy sins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, Ill.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

In some embodiments, inclusive of, without limitation, infectious disease applications, the present invention pertains to anti-infectives as additional agents. In some embodiments, the anti-infective is an anti-viral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In some embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

Other additional agents are described elsewhere herein, including the blocking antibodies targeted to an immune "checkpoint" molecules.

Subjects and/or Animals

The methods described herein are intended for use with any subject that may experience the benefits of these methods. Thus, "subjects," "patients," and "individuals" (used interchangeably) include humans as well as non-human subjects, particularly domesticated animals.

In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g. GFP). In some embodiments, the subject and/or animal is a transgenic animal comprising a fluorescent cell.

In some embodiments, the subject and/or animal is a human In some embodiments, the human is a pediatric human In other embodiments, the human is an adult human. In other embodiments, the human is a geriatric human In other embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In other embodiments, the subject is a non-human animal, and therefore the invention pertains to veterinary use. In a specific embodiment, the non-human animal is a household pet. In another specific embodiment, the non-human animal is a livestock animal In certain embodiments, the subject is a human cancer patient that cannot receive chemotherapy, e.g. the patient is unresponsive to chemotherapy or too ill to have a suitable therapeutic window for chemotherapy (e.g. experiencing too many dose- or regimen-limiting side effects). In certain embodiments, the subject is a human cancer patient having advanced and/or metastatic disease.

As used herein, an "allogeneic cell" refers to a cell that is not derived from the individual to which the cell is to be administered, that is, has a different genetic constitution than the individual. An allogeneic cell is generally obtained from the same species as the individual to which the cell is to be administered. For example, the allogeneic cell can be a human cell, as disclosed herein, for administering to a human patient such as a cancer patient. As used herein, an "allogeneic tumor cell" refers to a tumor cell that is not derived from the individual to which the allogeneic cell is to be administered. Generally, the allogeneic tumor cell expresses one or more tumor antigens that can stimulate an immune response against a tumor in an individual to which the cell is to be administered. As used herein, an "allogeneic cancer cell," for example, a lung cancer cell, refers to a cancer cell that is not derived from the individual to which the allogeneic cell is to be administered.

As used herein, a "genetically modified cell" refers to a cell that has been genetically modified to express an exogenous nucleic acid, for example, by transfection or transduction.

Technical and scientific terms used herein have the meaning commonly understood by one of skill in the art to which the present invention pertains, unless otherwise defined.

As used herein, the singular forms "a," "an" and "the" specifically also encompass the plural forms of the terms to which they refer, unless the content clearly dictates otherwise. As used herein, unless specifically indicated otherwise, the word "or" is used in the "inclusive" sense of "and/or" and not the "exclusive" sense of either/or." In the specification and the appended claims, the singular forms include plural referents unless the context clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. As used in this specification, whether in a transitional phrase or in the body of the claim, the terms "comprise (s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The invention will be further described in the following examples, which do not limit the scope of the invention described in the claims.

EXAMPLES

Example 1—Vector Engineered Immunotherapy Incorporating gp96-Ig and T Cell Costimulatory Fusion Proteins Elicits a Superior Antigen-Specific CD8+ T Cell Response Secretable heat-shock protein gp96-Ig based allogeneic cellular vaccines can achieve high frequency polyclonal CD8+ T cell responses to femtomolar concentrations of tumor antigens through antigen cross-priming in vivo. Multiple immunosuppressive mechanisms evolved by established tumors can dampen the activity of this vaccine approach. As described below, a systematic comparison of PD-1, PD-L1, CTLA-4, and LAG-3 blocking antibodies in mouse models of long-established B16-F10 melanoma demonstrated a superior combination between gp96-Ig vaccination and PD-1 blockade as compared to other checkpoints. Triple combinations of gp96-Ig vaccination, PD-1 blockade, and T cell costimulation using OX40, ICOS, or 4-1BB agonists provided a synergistic anti-tumor benefit.

A 96-Ig expression vector was re-engineered to simultaneously co-express ICOSL-Ig, 4-1BBL-Ig, or OX40L-Ig, thus providing a costimulatory benefit without the need for additional antibody therapy. As described below, co-secretion of gp96-Ig and these costimulatory fusion proteins in allogeneic cell lines resulted in enhanced activation of antigen-specific CD8+ T cells. Thus, combination immunotherapy can be achieved by vector re-engineering, obviating the need for vaccine/antibody/fusion protein regimens, and importantly may limit both cost of therapy and the risk of systemic toxicity.

Example 2—Vaccine+Costimulator Vector Re-Engineering

Figure 2:
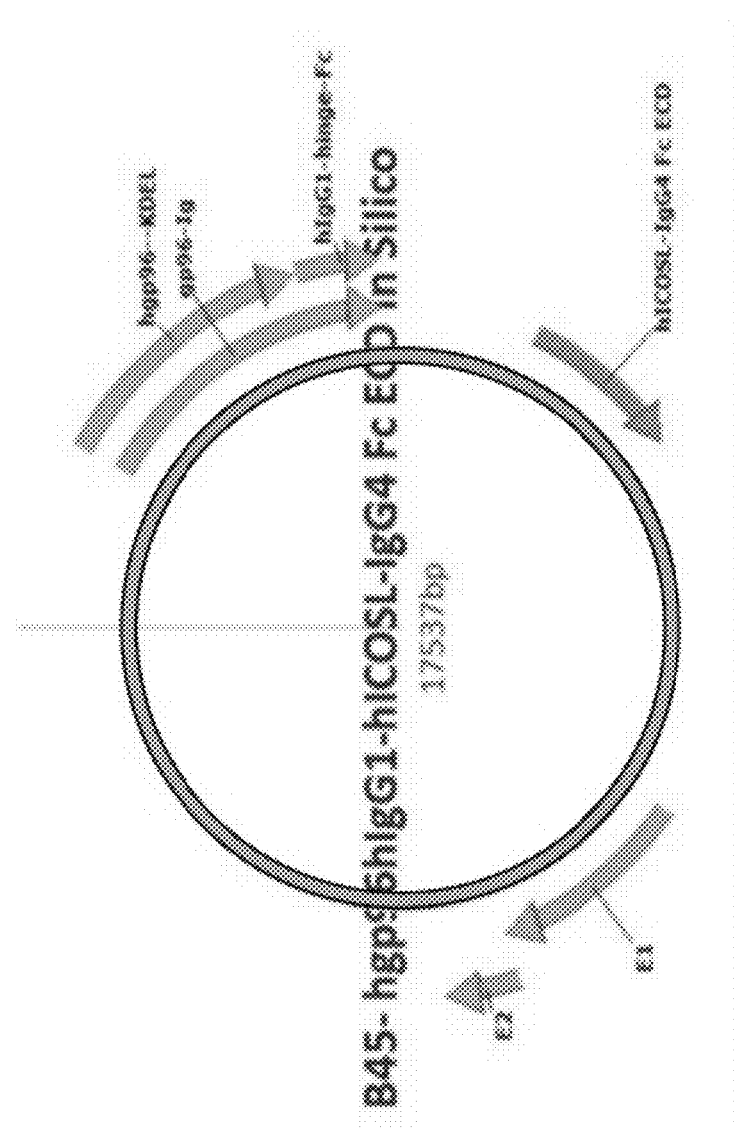
FIG. 2 is a schematic representation of a mammalian expression vector (B45) encoding a secretable gp96-Ig fusion protein in one expression cassette and a T cell costimulatory fusion protein (by way of non-limiting illustration, ICOSL-IgG4 Fc) in a second cassette.
Figure 3:
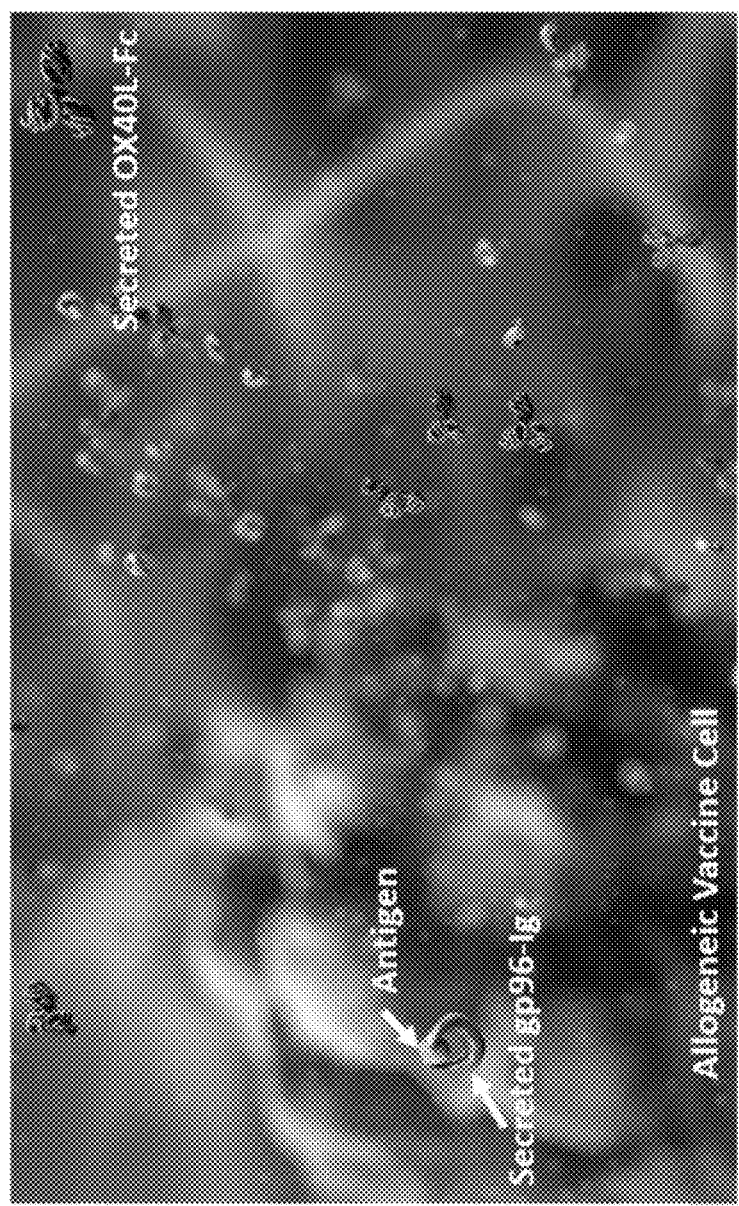
FIG. 3 is an illustration of an allogeneic tumor cell that has been transfected with a vector encoding two secretable proteins. The first protein, gp96-Ig, forms a secretable dimer (smooth) that chaperones cell-derived antigens outside the cells. The second protein is a trimeric secretable T cell costimulatory fusion protein (rough) which is secreted by the vaccine cell and may freely bind to a nearby costimulatory receptor on the surface of a T cell.

A vector re-engineering strategy was employed to incorporate vaccine and T cell costimulatory fusion proteins into a single vector. Specifically, the original gp96-Ig vector was re-engineered to generate a cell-based combination IO product that secretes both the gp96-Ig fusion protein and various T cell costimulatory fusion proteins (FIGS. 1 and 2). The combined local secretion of vaccine and costimulatory fusion protein (FIG. 3) can activate tumor antigen specific T cells, and is anticipated to enhance antigen-specific immunity with limited cost and systemic toxicity, particularly when combined with administration of an agent (e.g., an antibody against PD-1) that inhibits immunosuppressive molecules produced by tumor cells.

Example 3—In Vivo Studies of ImPACT Vs. ComPACT

Materials and Methods

Cell Culture and Vaccine Cell Line Generation:

3T3 cells were maintained in IMDM with glutamine and 10% Bovine Growth Serum (BGS) at 37° C. in 5% $CO_2$. A 3T3-Ovalbumin-Hygro parental cell line was established using hygromycin resistant plasmid backbone pcDNA3.1 encoding chicken ovalbumin (Ova) through nucleofection with the 4D-NUCLEOFECTOR™ and Cell Line NUCLEOFECTOR™ Kit SE (Lonza) according to the manufacturer's directions. Single cell clones secreting high-level Ova were screened by ELISA and used to generate 3T3-Ova-Gp96-Ig (ImPACT) and 3T3-Ova-Gp96-Ig/OX40L-Fc (ComPACT) through nucleofection of G418 resistant plasmid pB45 encoding either murine Gp96-Ig or Gp96-Ig and the extracellular domain of OX40L-Fc, respectively. Again, single cell clones of both ImPACT and ComPACT were generated through antibiotic selection and clones secreting similar levels of mouse IgG were screened further and used for subsequent analysis. OX40L mRNA expression was confirmed by qRT-PCR and protein levels were assessed by western blot.

CT26 cells were maintained in IMDM with glutamine and 10% Fetal Bovine Serum at 37° C. in 5% $CO_2$. CT26 versions of ImPACT (CT26-Gp96-Ig) and ComPACT (CT26-Gp96-Ig/OX40L-Fc) were generated using the same expression plasmids as above, however transfected into the CT26 cell line using EFFECTENE® Transfection Reagents (Qiagen) according to manufacturer's directions. Single cell clones were isolated under antibiotic selection and screened for mouse IgG secretion by ELISA. OX40L mRNA expression was confirmed by qRT-PCR.

B16.F10 cell lines were first established by generating an ova parental clone (B16.F10-ova: as described above for 3T3 cells). Then, B16.F10-ova versions of ImPACT (B16.F10-ova-gp96-Ig) and ComPACT (B16.F10-ova-gp96-Ig/Fc-OX40L) were again transfected with the identical plasmids as described above, and selected for high-level gp96-Ig secretion.

Mouse Models, OT-I/OT-II Transfer and Analysis:

Antigen specific CD8 T cells were isolated from the spleens of OT-I/EGFP mice, carrying the T cell receptor transgenes TCRα-V2 and TCRβ-V5, that recognize ovalbumin residues 257-264 during $H2K^b$ MHC class I antigen cross-presentation. Antigen specific CD4 T cells were isolated from the spleens of OT-II mice, expressing the mouse α- and β-chain T cell receptor that is complementary with the CD4 co-receptor and is specific for chicken ovalbumin residues 323-339 during $I-A^b$ MHC class II antigen cross-presentation.

Briefly, mice were sacrificed through $CO_2$ asphyxiation followed by cervical dislocation, and the spleen was dissected into sterile PBS+2 mM EDTA. Splenocytes were dissociated from the tissue and passed through a 100 μM strainer. Cells were pelleted at 1,200 RPM for 5 minutes and red blood cells were lysed by adding 5 mL 1×ACK lysis buffer (150 mM $NH_4Cl$, 10 mM $KHCO_3$ and 1 mM EDTA) for 1-2 minutes at room temperature. Following lysis, an equal volume of 1×PBS was added and the cells were again pelleted at 1,200 RPM for 5 minutes. OT-I (CD8) and OT-II (CD4) were isolated from total splenocytes using CD4 and CD8 isolation kits from StemCell Technologies, according to the manufacturer's directions. OT-I ($0.5 \times 10^6$ cells per mouse) and OT-II ($1 \times 10^6$ cells per mouse) were transferred via intravenous (IV) tail vein injections to mice transgenic for FOXP3-RFP (to track regulatory T cells: Tregs). The IV injection day corresponded to experimental day −1.

On days 0 and 35 (in the case of boosted mice), mice were either untreated, vaccinated with the 3T3-Ova parental clone as a control, vaccinated with ImPACT (alone or in combination with 100 μg of agonist antibodies to ICOS (BioLegend #313512), 4-1BB (3H3 antibody, Bio-X-Cell) or OX40 (OX86 antibody, Bio-X-Cell), or vaccinated with ComPACT. Vaccinations consisted of $1 \times 10^6$ cells and were administered by intraperitoneal injection (IP). Lymphocytes harvested from peripheral blood were analyzed by flow cytometry throughout the time-course.

CT26 Tumor Model and Analysis:

For CT26 tumor studies, BALB/C mice were inoculated with either $2 \times 10^5$ or $5 \times 10^5$ tumor cells via subcutaneous injection into the rear flank, indicating day 0. For B16.F10-ova studies, C57BL/6 mice were inoculated with $5 \times 10^5$ tumor cells into the rear flank, indicating day 0. On vaccination days, tumor bearing mice were either untreated or vaccinated with mitomycin-C (Sigma) treated ImPACT, ImPACT+100 mg anti-OX86 (referred to as OX40(ab) throughout) or ComPACT cells. Tumor area (mm$^2$) and overall survival was assessed throughout the time course. 30-day survival criteria included total tumor area less than 175 mm$^2$ with no sign of tumor ulceration. Complete responders, in which tumors established and were subsequently rejected following treatment, are listed in FIG. 12, panel D and FIG. 11, panel E. A cohort of mice inoculated with 2×10$^5$ cells was sacrificed 11 days after tumor inoculation. Tumors were excised from these mice, trypsinized at 37° C. for 10 minutes, dissociated, and passed through a 100 µM cell strainer. Cells were pelleted, red blood cells were lysed (as described above), and RNA was isolated, reverse transcribed, and analyzed by qPCR (see below). A cohort of CT26 experimental mice was euthanized on day 12 for AH1-tetramer analysis in splenocytes and genetic analysis of tumor tissue. Tumors were excised from these mice, trypsinized at 37° C. for 10-15 minutes, dissociated and homogenized through a 100 mM strainer. Cells were pelleted and processed for RNA isolation (see below).

Flow Cytometry:

Flow cytometry and cell sorting was performed on the Sony SH800. For extracellular staining, cell pellets were resuspended in 1×PBS buffer containing 1% bovine serum albumin (BSA), 0.02% sodium azide, and 2 mM EDTA, and the appropriate antibodies and incubated on ice in the dark for 30 minutes. Cells were then washed in flow cytometry buffer, resuspended and then analyzed. For intracellular staining, cells were fixed and permeabilized using the FOXP3 Fix/Perm kit from BioLegend, stained as described above, washed in flow cytometry buffer, resuspended and then analyzed. Antibodies used were PE/Cy7-CD4 (Sony, 1102640), AF700-CD8a (Sony, 1103650), APC-TCR Vβ5.1, 5.2 (Sony, 1297530), PacificBlue-TCR Vα2 (Sony, 1239080), APC-KLRG1 (BioLegend, 138412), BV421-CD44 (BioLegend, 103039), BV605-CD127 (BioLegend, 135025), APC-Ki67 (BioLegend, 652406), PE/Cy7-IFNγ (Biolegend, 505826), and BV421-IL2 (BioLegend, 503825).

ELISAs:

Standard ELISA conditions were set such that 1×10$^6$ cells were plated in 1 mL of culture media and the supernatant analyzed after 24 hours. High-binding ELISA plates were coated with 10 µg/mL mouse IgG (Jackson Laboratories #115-005-062) in sodium bicarbonate buffer. Coated plates were incubated over night at 4° C. The following morning, plates were washed 3 times with TBS-T (50 mM Tris, 150 mM NaCl and 0.05% Tween 20), blocked for 1 hour with Casein Blocking Buffer (Sigma) and again washed 3 times with TBS-T. To the plates, 50 µL of cell supernatants along with an 11-point mouse IgG standard set of samples were added to the coated ELISA plates and incubated at room temperature for 1 hour. Plates were washed 3 times with TBS-T and 50 µL of detection antibody (Jackson Laboratories #115-035-071) was added, and incubated for 1 hour at room temperature in the dark. Plates were washed 3 times with TBS-T and 100 µL of SUREBLUE™ TMB Microwell Peroxidase Substrate (KPL) was added to each well and allowed to incubate at room temperature for 20 minutes in the dark. To stop the reaction, 100 µL of sulfuric acid was added to each well and plates were read immediately on a BioTek plate reader. Samples were run at least in triplicate at multiple dilutions.

RNA Isolation and qRT-PCR:

Total RNA was prepared using RNeasy and RNeasy Micro kits (Qiagen) according to the manufacturer's recommendations, including on-column DNase treatment. A total of 1 µg (using RNeasy) or 100 ng (using RNeasy Micro) was used to synthesize cDNA with the First-strand cDNA synthesis kit from OriGene. qPCR was performed using KAPA SYBR FAST, SYBR green master mix (Kapa Biosystems) and then analyzed on a Roche Lightcycler. Values were normalized to 18S mRNA and represent the average±standard error of the mean (SEM) for a minimum of 3 biological replicates, all run in triplicate. Primer sequences used were:

```
IFN-gamma:
                                 (SEQ ID NO: 14)
F: 5'-CTGCCACGGCACAGTCATTG-3'

(SEQ ID NO: 15)
R: 5'-gccagttcctccagatatcc-3'

TNF-alpha:
                                 (SEQ ID NO: 16)
F: 5'-CCACGCTCTTCTGTCTACTG-3'

(SEQ ID NO: 17)
R: 3'-gccatagaactgatgagaggg-3' granzyme-B
                                 (SEQ ID NO: 18)
F: 5'-CTACTGCTGACCTTGTCTCTG-3'

(SEQ ID NO: 19)
R: 3'-agtaaggccatgtagggtcg-3'

IL-2
                                 (SEQ ID NO: 20)
F: 5'-CTGCGGCATGTTCTGGATTTGACT-3'

(SEQ ID NO: 21)
R: 5'-AGTCCACCACAGTTGCTGACTCAT-3' perforin-1
                                 (SEQ ID NO: 22)
F: 5'-GACACAGTAGAGTGTCGCATG-3'

(SEQ ID NO: 23)
R: 5'-aagcatgctctgtggagctg-3' beta-actin
                                 (SEQ ID NO: 24)
F: 5'-aaggccaaccgtgaaaagat-3'

(SEQ ID NO: 25)
R: 5'-gtggtacgaccagaggcatac3'
```

Western Blot Analysis:

ImPACT and ComPACT cells were treated for 16 hours with Brefeldin-A to inhibit protein transport and secretion. Cells were then lysed in RIPA buffer (25 mM Tris-HCL, 150 mM NaCl, 1% NP-40, 1% NaDeoxycholate, and 0.1% SDS), containing 1× complete protease inhibitor cocktail (Roche) for 10 minutes on ice. Protein concentration was determined using DC Protein Assay kit (Bio-Rad) and 20 µg of protein was probed. Antibodies were: CD252 (OX40L, Abcam #ab156285, 1:1000 dilution), histone H3 (Active Motif #61278, 1:10,000), histone H4 (Active Motif #61300, 1:10,000), and beta actin (Abcam #ab8226, 1:10,000).

LEGENDplex Cytokine Analysis:

Experimental mice were euthanized through $CO_2$ asphyxiation and cervical dislocation and whole blood was collected via cardiac puncture. Red blood cells were allowed to settle by gravity for 1 hour at room temperature and the remaining cells were pelleted at 1,200 RPM for 5 minutes. Serum was then transferred to a new 1.5 mL eppendorf tube.

Cytokine analysis was performed using the LEGEND-PLEX™ Cytokine Analysis kit (BioLegend) according to manufacturer recommendations and analyzed on the Sony SH800.

Statistical Analysis:

Experimental replicates (N) are shown in the figures. Unless noted otherwise, values plotted represent the mean from a minimum of 3 distinct experiments and error is SEM. Statistical significance (p-value) was determined using unpaired parametric t-tests with Welch's correction. Significant p-values are labeled with an asterisk (*), and the corresponding p-value is labeled in each figure.

Results

Many new trials will investigate whether adding a therapeutic vaccine or T cell costimulatory antibody is an effective strategy to increase the proportion of responding patients and the durability of clinical responses. The implementation of such a strategy is limited by several factors, including an incomplete understanding of which agents may provide synergistic benefit, whether to toxicities of such combinations will be tolerable and eventually how the healthcare system will manage such combinations.

Figure 4E:
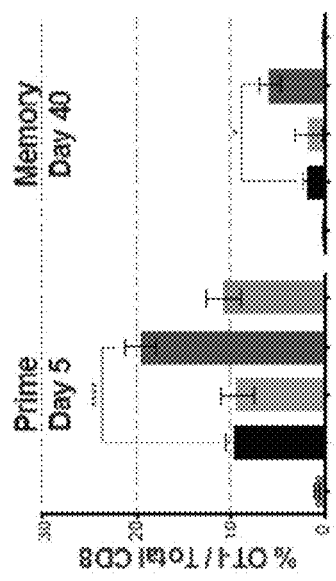
Figure 4F:
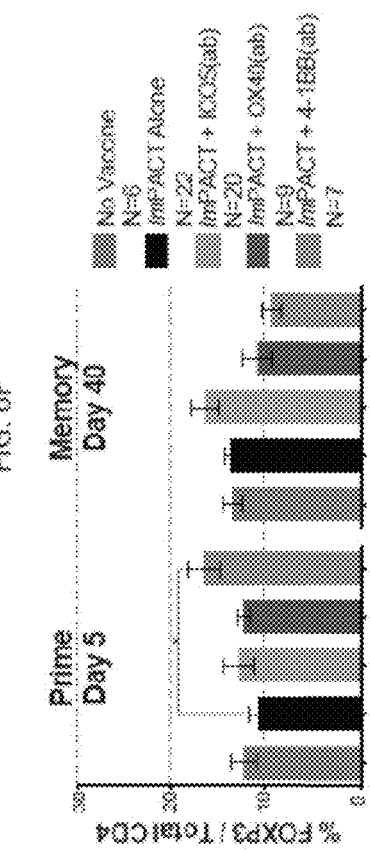
Figure 4G:
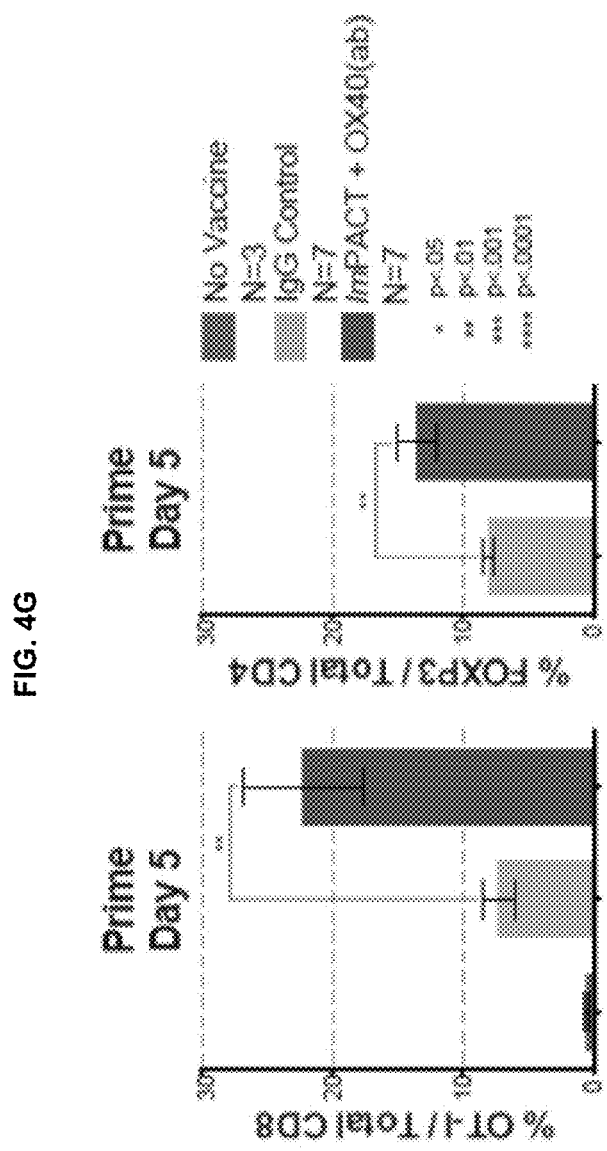
Figure 5A:
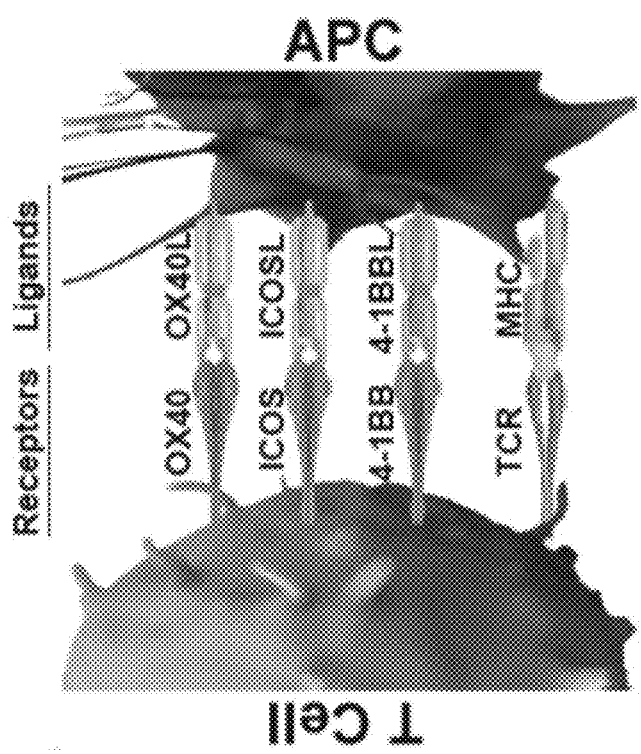
Figure 5D:
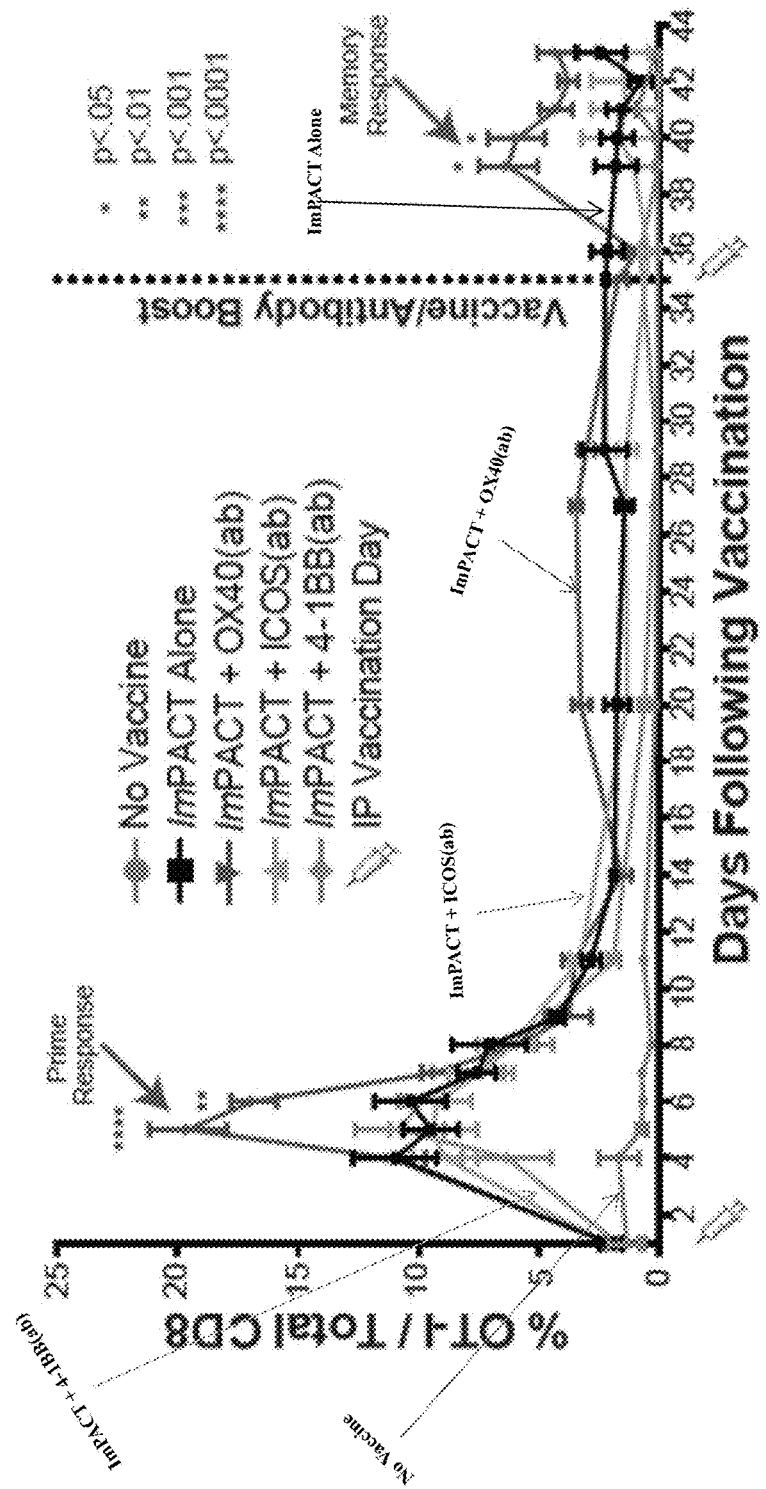

To investigate the potential synergy between a vaccine and individual T cell costimulatory molecules, a series of head-to-head studies was performed in pre-clinical mouse models. Using a cell-based vaccine expressing a modified secretable gp96-Ig fusion protein (FIG. 4A), studies were conducted to investigate whether co-administration of agonistic antibodies targeting OX40, 4-1BB, or ICOS would provide further costimulation of antigen-specific CD8+ T cells (FIGS. 5A-5C) Immunization of C57BL/6 mice that were adoptively transferred with ovalbumin-specific CD8+ T cells (OT-I) with a 3T3-ova-gp96-Ig vaccine led to proliferation of OT-I cells to 10% of peripheral blood CD8+ T cells. This response could be doubled by additional administration of OX40 agonist antibodies, but not 4-1BB or ICOS co-stimulatory antibodies (FIG. 5D).

Figure 6A:
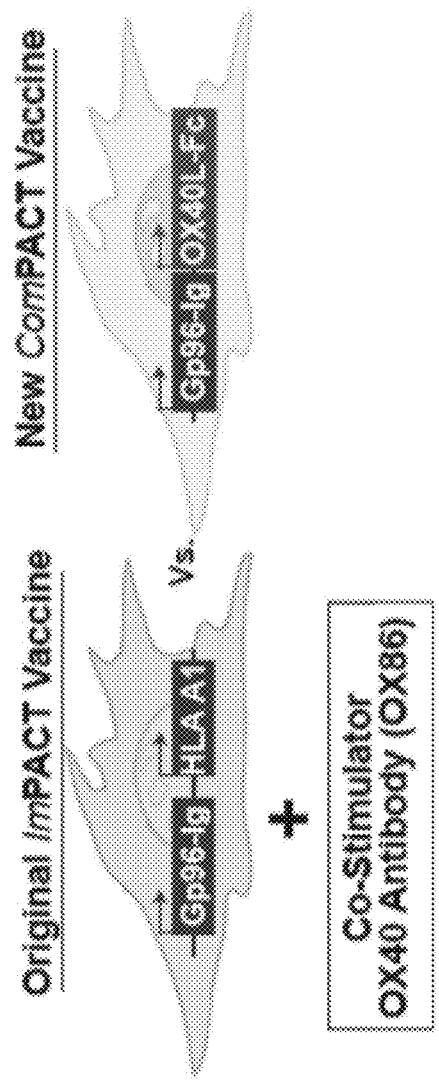
FIGS. 6A-6C show that the combination of T cell co-stimulator OX40L with ImPACT into a new vaccine vector ("ComPACT") produced surprisingly superior antigen specific CD8+ T cell expansion as compared to coadministration of OX40 agonist antibody.
Figure 7A:
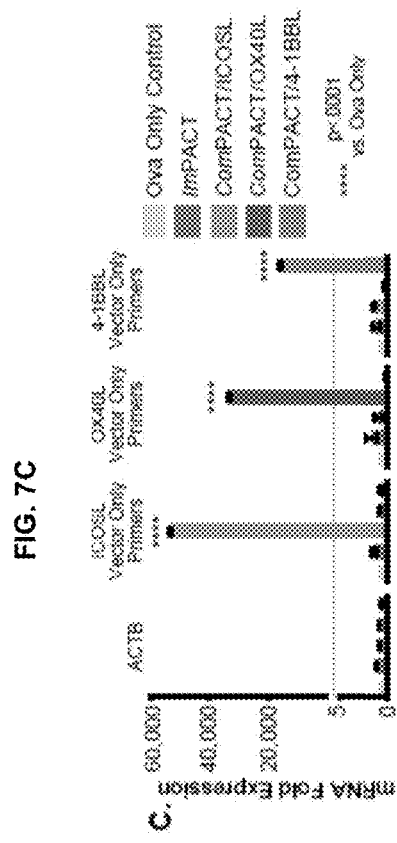
FIGS. 7A-7F show that the combination of gp96-Ig and OX40L, ICOSL, or 4-1BBL expression in ComPACT results in high-level CD8, antigen specific T cell response.
Figure 7B:
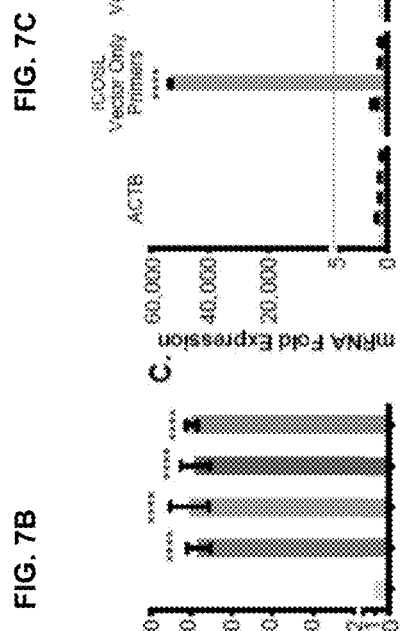
Figure 7C:
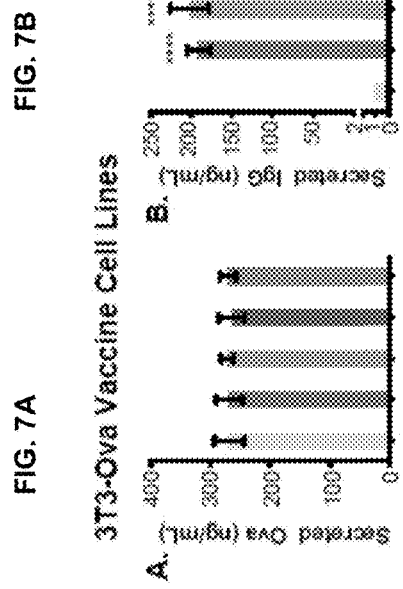
Figure 7D:
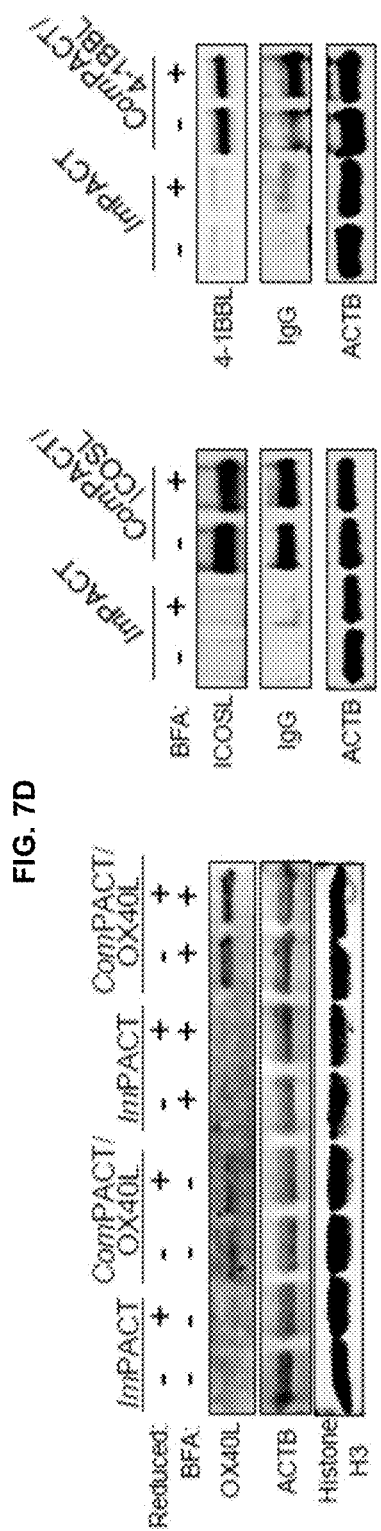
Figure 7E:
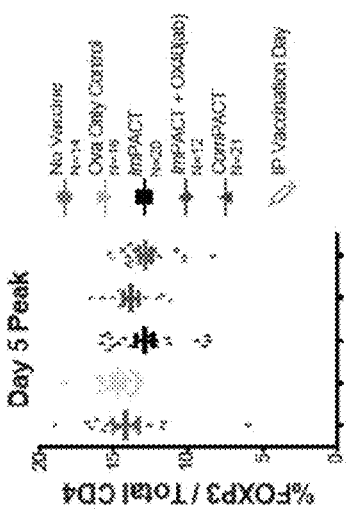
Figure 7F:
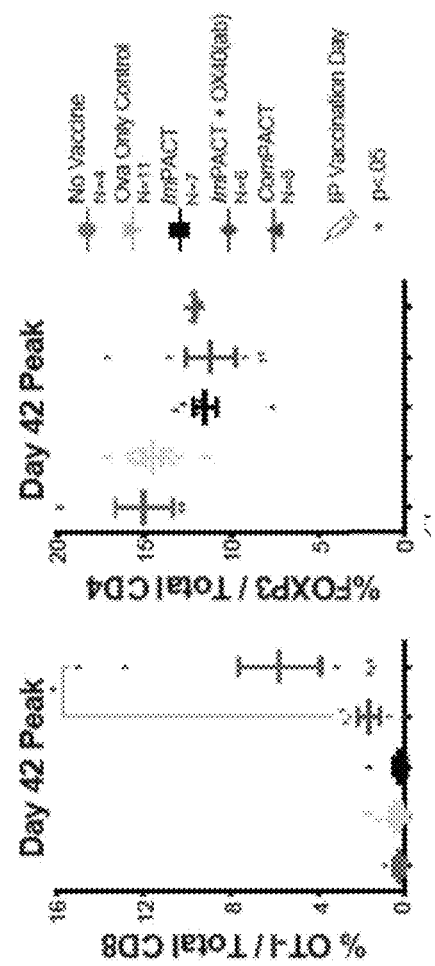

T cell costimulation by OX40L is triggered by local inflammation in a spatially restricted microenvironment by antigen presenting cells over the course of 2-5 days. Administration of OX40 receptor agonist antibodies provides systemic costimulation that can persist for several weeks. Since vaccines are typically administered locally, experiments were performed to determine whether an OX40L fusion protein (Fc-OX40L) could be co-expressed in the second cassette of the gp96-Ig containing plasmid as a strategy to both limit systemic co-stimulation and enable combination immunotherapy with a single compound (FIG. 6A). As proof of concept, a 3T3 cell co-expressing soluble ovalbumin and either gp96-Ig alone ("ImPACT") or gp96-Ig together with Fc-OX40L, ICOSL, or 4-1BBL was generated. These cell lines were stably selected to secrete similar amounts of both ova and gp96-Ig (FIGS. 7A and 7B). Expression of Fc-OX40L, ICOSL, or 4-1BBL was evaluated by RT-PCR and Western blotting (FIGS. 7C and 7D), and shown to be functionally active in cell culture supernatants by an IL-2 secretion assay from primary splenocytes.

Figure 6B:
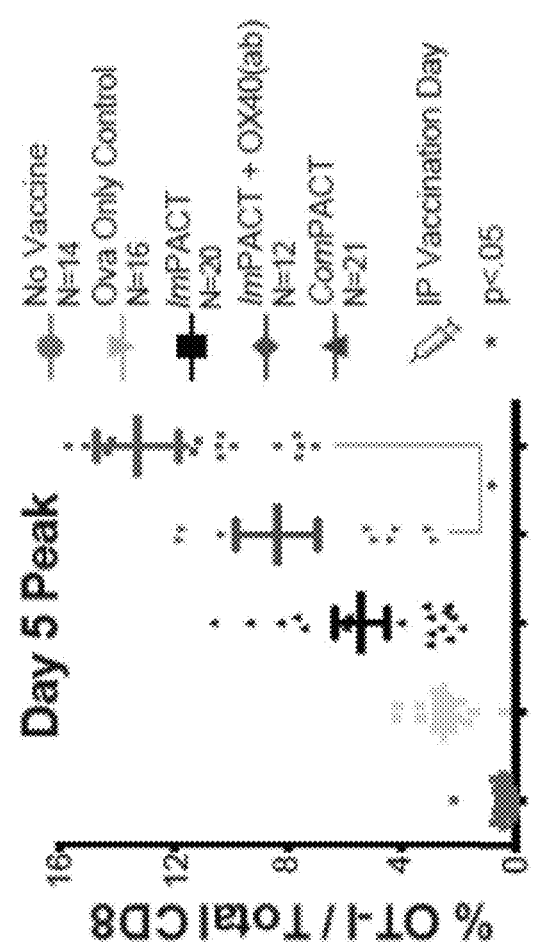
Figure 6C:
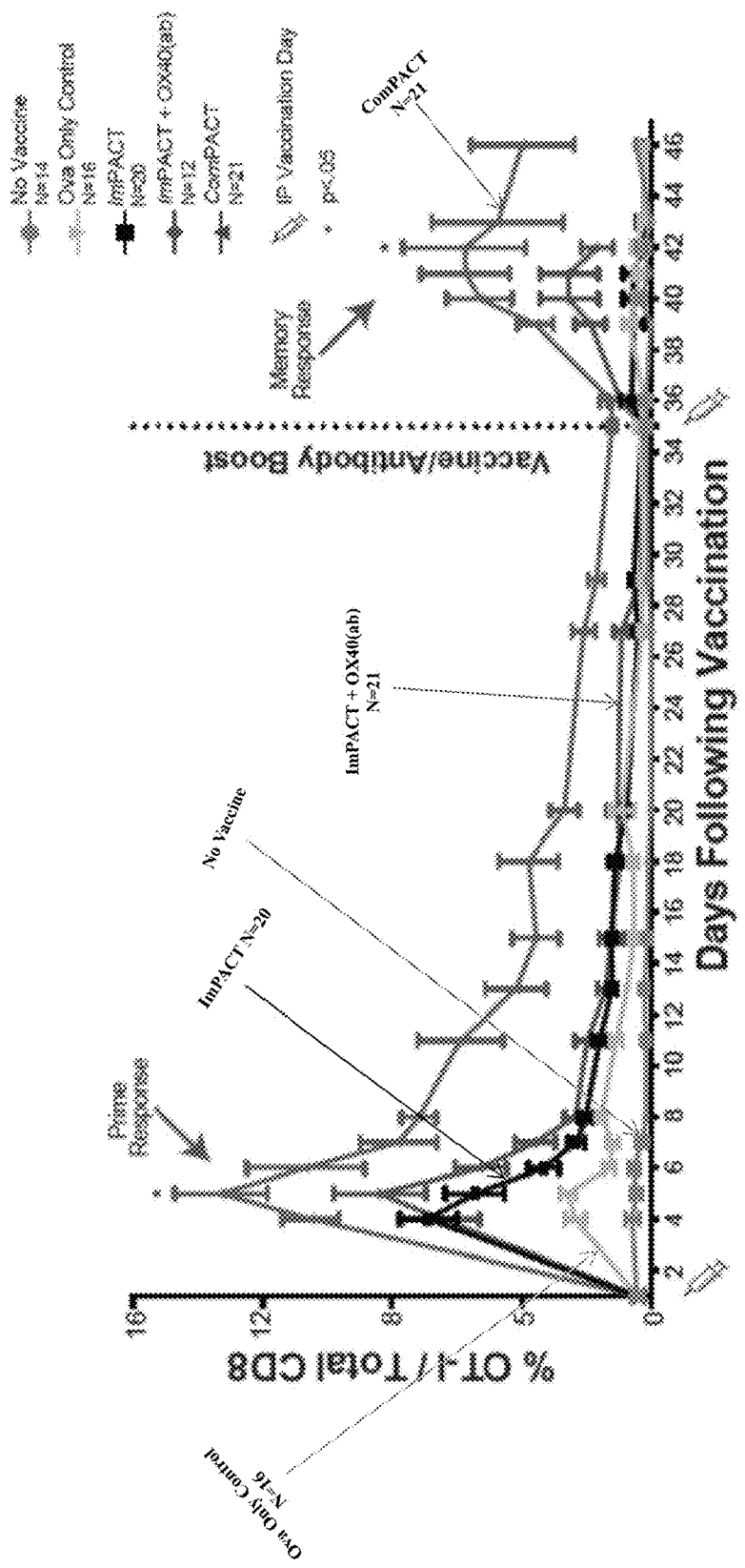

The in vivo activity of ImPACT either alone or in combination with OX40 agonist antibodies was compared to ComPACT using the OT-I model described in FIG. 5. Distinct cell lines were used in this experiment because the co-transfections described above were not possible with the neomycin resistance cassette expressing ova in FIG. 5. Since ComPACT was administered locally, one might not have expected the dramatic priming and boosting effects vs. the ImPACT combination with the OX40 agonist antibody, which was administered systemically. As shown in FIGS. 6B and 6C, however, ComPACT immunization provided surprisingly and significantly improved proliferation of OT-I cells following primary immunization either with ImPACT alone or in combination with OX40 agonist antibodies. The peak expansion in the peripheral blood was increased on day 5 with ComPACT, but more importantly, so was the duration of the response from days 6-20.

Figure 8A:
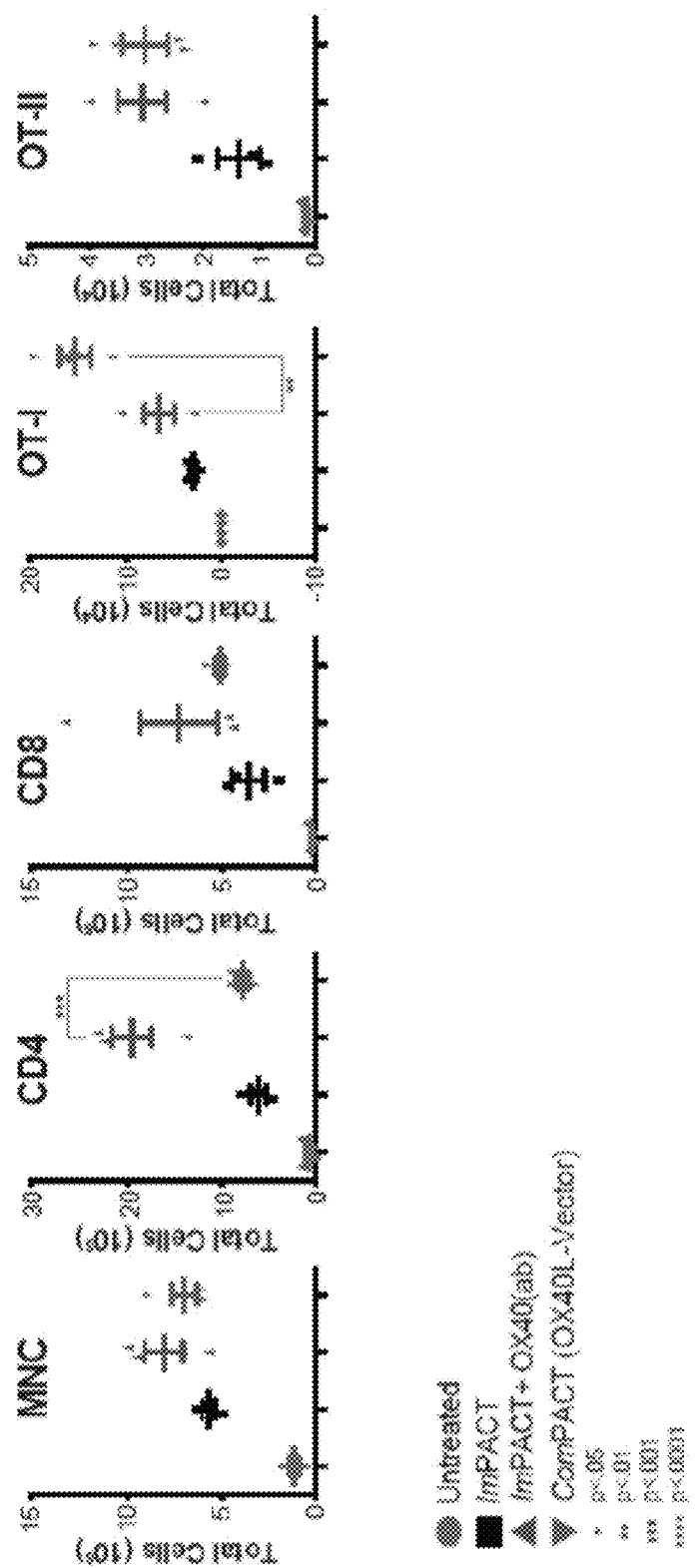
FIGS. 8A-8E show that ComPACT elicited antigen specific CD8+ expansion while OX40 antibody led to non-specific T cell activation.
Figure 8B:
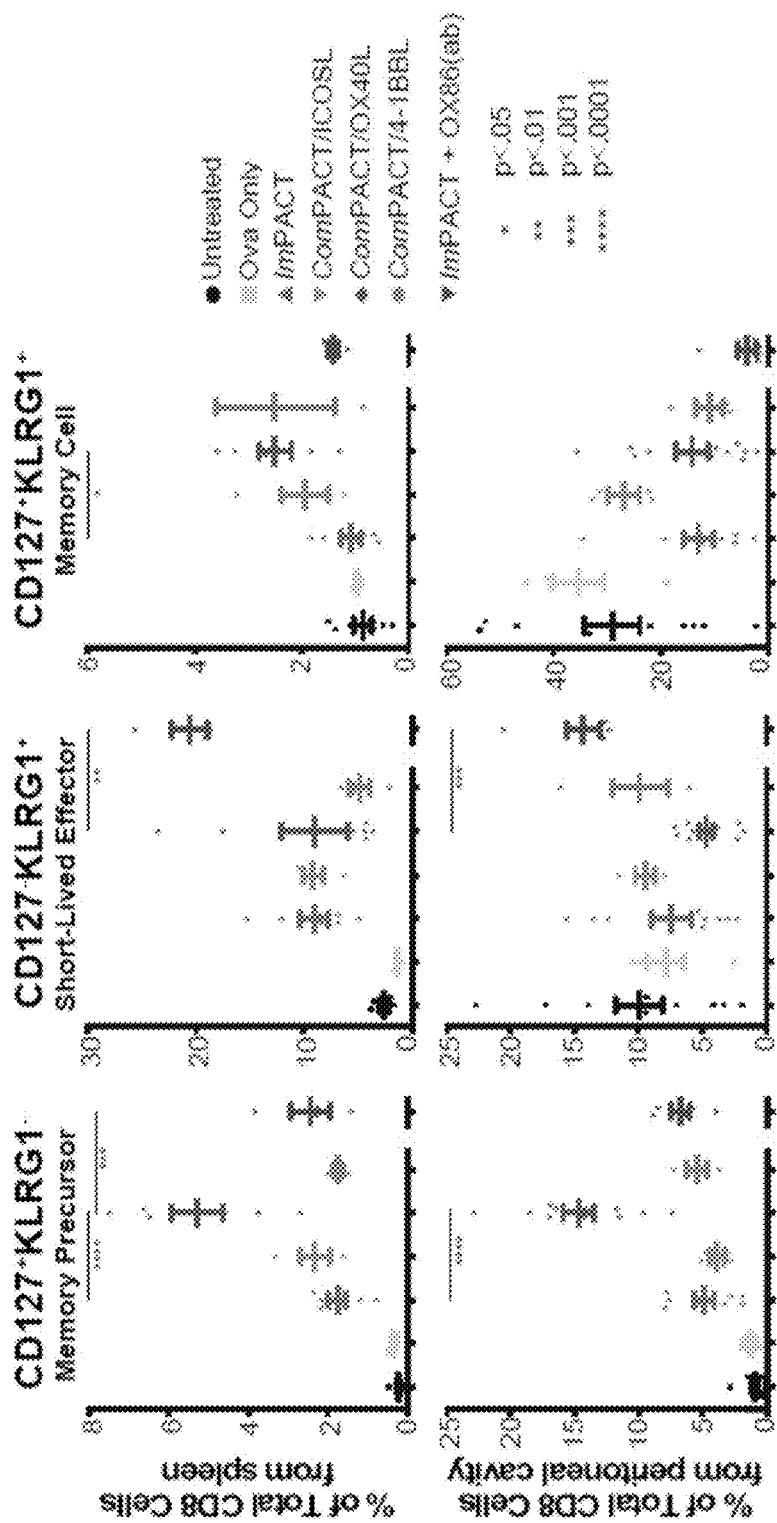

The memory response to OX40 agonistic antibodies in combination with vaccination is relatively weak within the antigen specific CD8 compartment. The boost response was evaluated by re-immunizing mice on day 35 after the primary immunization (FIG. 6C). While the combination of OX40 agonist antibodies provided a relatively weak boost of the OT-I response, ComPACT treated mice demonstrated a boost response that nearly matched the magnitude of the primary response (FIG. 6C). Flow cytometric analysis of splenocytes and peritoneal cells from mice receiving Com-PACT, revealed a marked increase in CD127$^+$KLRG1$^-$ cells compared to the other groups, indicating an increase in memory precursor cells (FIG. 8B). This effect was observed with various ComPACTS, including ComPACT (OX40L), ComPACT (ICOSL) and ComPACT (4-1BBL) but not with OX40 agonist antibody treatment. The various ComPACTs did not induce an increase in short-lived effector cells (CD127$^-$KLRG1$^+$, FIG. 8B), as did OX40 agonist antibody treatment. The ComPacts, however, did increase memory T cells (CD127$^+$KLRG1$^+$) within the spleen (FIG. 8B). These data indicate that local administration of an OX40L, ICOSL, or 4-1BBL agonist fusion proteins significantly increased both the primary and the boost response in the antigen-specific CD8 compartment, which is correlated with an increase in memory precursor cells and a prolonged contraction phase following priming In addition, these data also revealed a novel and unexpected mechanism of action for ComPACT treated mice in comparison to ImPACT+/−OX40 agonist antibody.

Figure 8C:
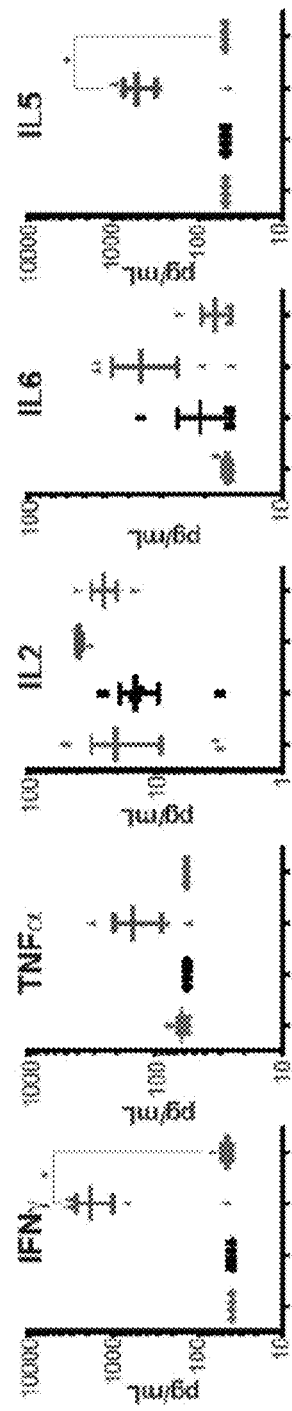
Figure 8D:
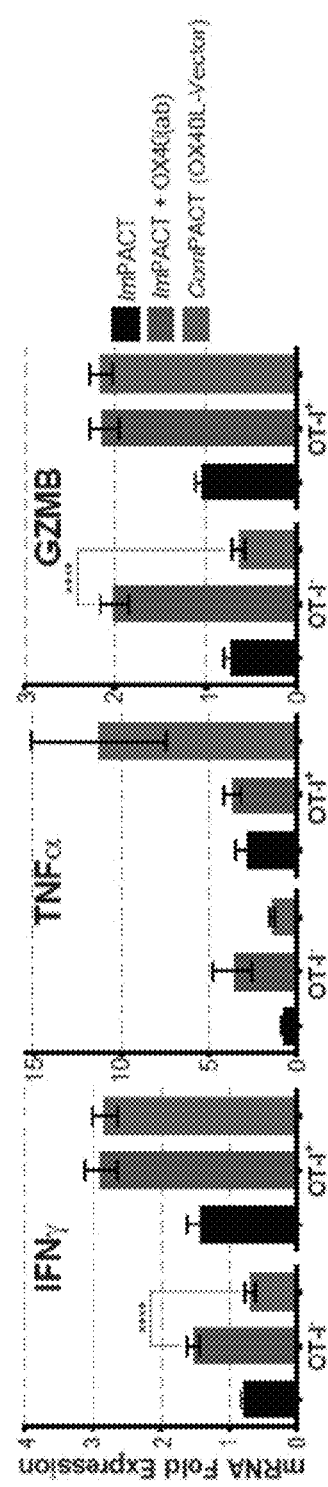
Figure 8E:
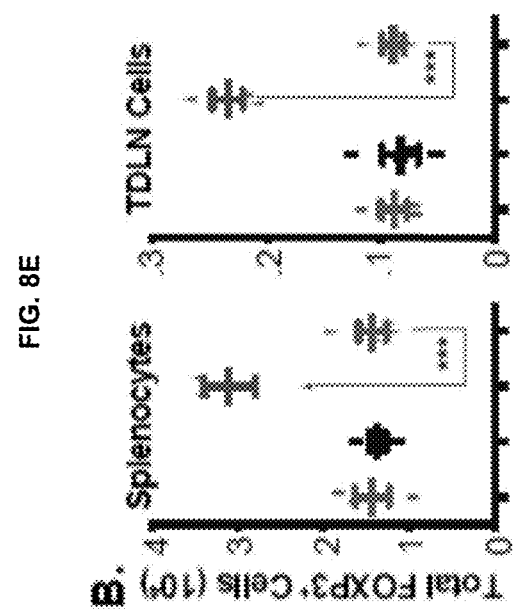
Figure 9A:
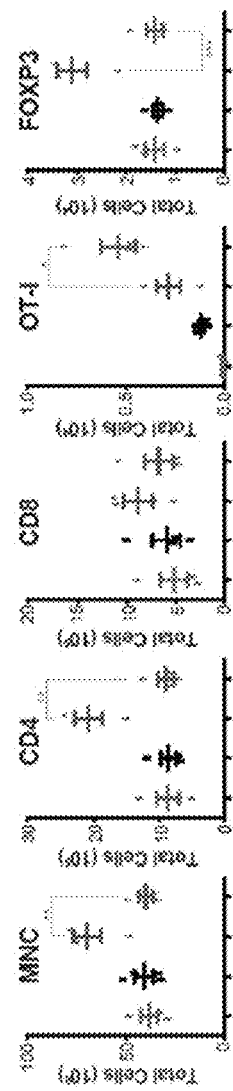
FIGS. 9A-9C show that ComPACT (in this figure, Gp96-Ig/OX40L-Fc) treatment results in antigen specific CD8 T cell activation, whereas coadministration of OX40(ab) treatment elicits non-specific immune cell activation including increases in FOXP3 Tregs in both the spleen and lymph nodes.
Figure 9B:
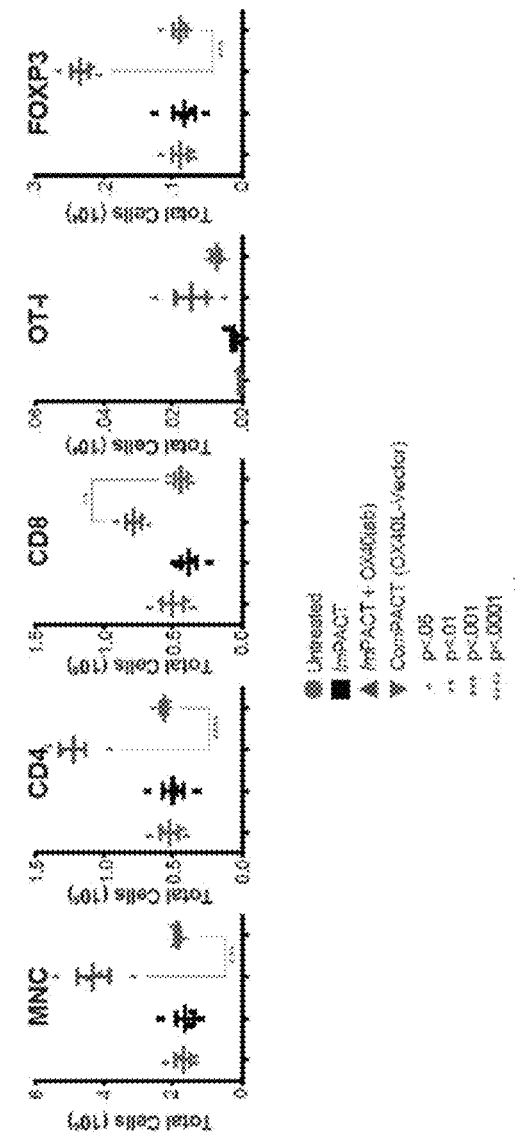
Figure 9C:
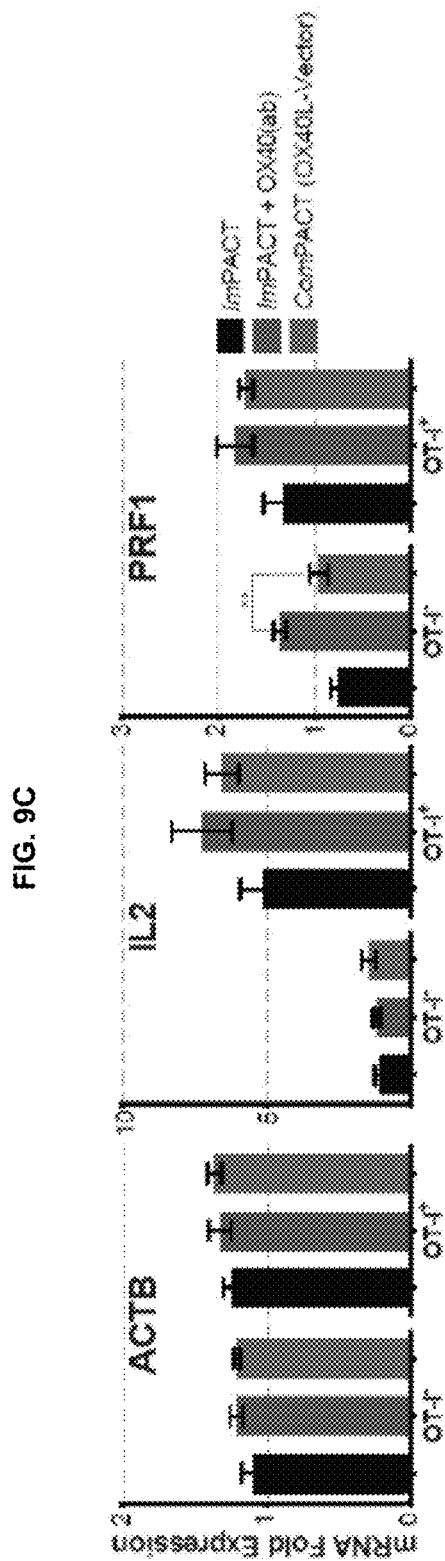

It was possible that the reason for increased primary and boost responses in the antigen-specific CD8 compartment with locally provided OX40L was due to decreased off-target activation provided by systemic administration of OX40 agonist antibodies. To test this hypothesis, peritoneal cells, splenocytes and tumor draining lymph node (TDLN) cells were isolated on day 8 from mice that were immunized with ImPACT+/−OX40 agonist antibody or ComPACT and analyzed by flow cytometry and quantitative RT-PCR (qRT-PCR) to distinguish between off-target immune activation and an antigen-specific response. Analysis of peritoneal cells isolated on day 8 following primary immunization indicated increased numbers of total mononuclear, OT-I, and OT-II cells in ComPACT treated mice, but also increased numbers of total CD4 cells in mice treated with OX40 agonist antibodies (FIG. 8A). Increased levels of total CD4+ cells and FOXP3+ regulatory T cells (Treg) were detected in the peritoneal cavity, spleen and TDLN in mice treated with OX40 agonist antibodies (FIGS. 8A and 8E). In contrast, ComPACT treated mice specifically amplified antigen-specific OT-I (CD8+) and OT-II (CD4+) cells with no apparent stimulation of Treg cells (FIGS. 8A and 8E). Similar findings also were observed in the spleen and lymph nodes, indicating systemic expansion of total CD4 cells as well as antigen-specific CD4 cells (FIGS. 9A and 9B). CD4+ FoxP3+ regulatory T cells (Treg) also were increased for OX40 agonist, but not ComPACT treated animals Serum cytokine analysis further demonstrated a systemic increase in IFNγ, TNFα, IL-5 and IL-6 in mice treated with OX40 agonist antibodies (FIG. 8C). To investigate the cellular source of the systemic cytokine increase, RT-PCR was performed on either total CD8+ cells or OT-I cells on day 8 following immunization. ComPACT treated mice showed an increase in IFNγ, TNFα and granzyme-B that was isolated to the OT-I population, whereas mice treated with OX40 agonist antibodies showed an increase in both the OT-I and the total CD8 population (FIG. 8D).

These data indicate that OX40L fusion proteins can be locally provided by stable transfection of a plasmid co-expressing a heat shock protein gp96-Ig based vaccine. Initial feasibility related to whether sufficient concentrations of Fc-OX40L were secreted to provide costimulation demonstrated that this was achievable, and surprisingly, more effective than systemic administration of OX40 agonist antibodies. The costimulated OT-I cells produced equivalent levels of effector cytokines as OX40 antibody costimulated OT-I cells, and would be expected to exert increased cytotoxic activity against a target cell.

Figure 10A:
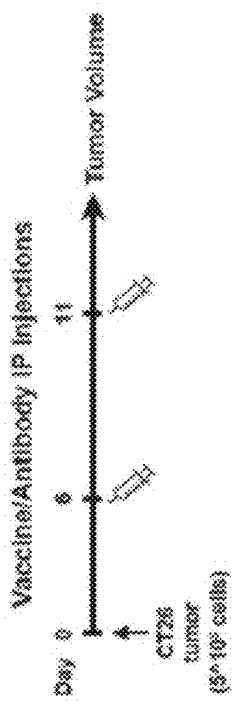
FIGS. 10A-10C show that in tumor bearing mice, ComPACT (in this figure, Gp96-Ig/OX40L-Fc) treatment resulted in the maximum number of tumor invading lymphocytes and tumor regression.
Figure 10B:
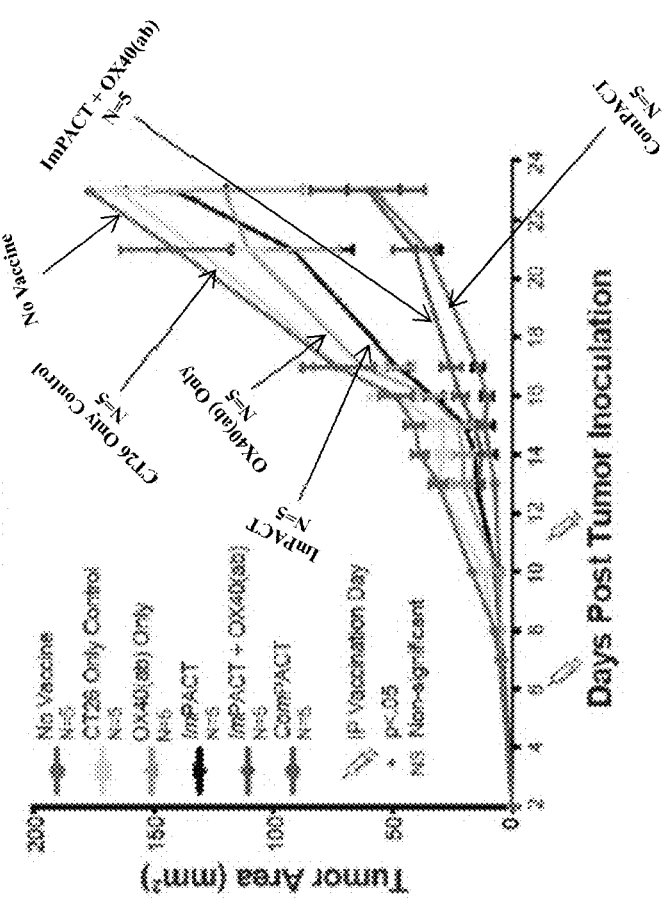
Figure 10C:
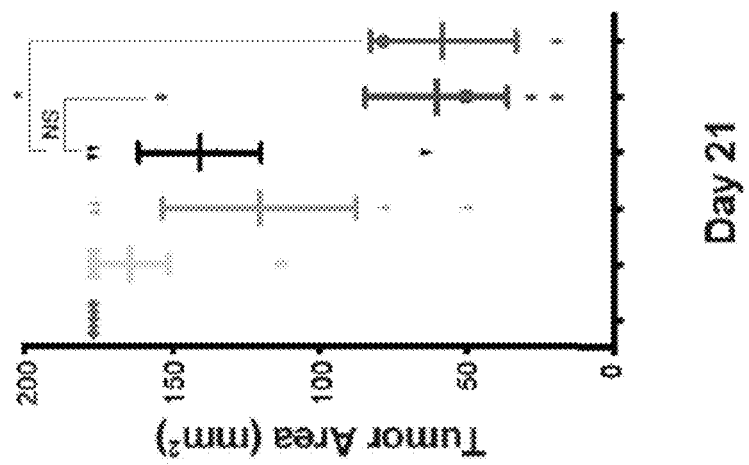

To investigate the functional activity of ImPACT+/−OX40 antibodies versus ComPACT in a murine tumor model, CT26 cells were stably transfected with these constructs as outlined for 3T3 cells in FIG. 7 (FIGS. 10A-10C). In one set of experiments, mice were inoculated with CT26 cells on day 0, and then treated with mitomycin-C treated CT26 cells, CT26-gp96-Ig, CT26-gp96-Ig combined with OX40 agonist antibodies or with CT26 ComPACT on days 6 and 11 post tumor inoculation. In a second set of experiments, mice were inoculated with CT26 cells on day 0, and then immunized with mitomycin-C treated CT26 cells, CT26-ImPACT, CT26-ImPACT combined with OX40 agonist antibody or with CT26-ComPACT cells on days 4, 7 and 10 post tumor inoculation (FIG. 11A). Quantitative RT-PCR on tumor tissue isolated on day 12 post-tumor inoculation revealed increased expression of CD8a, IL-2 and IFNγ in OX40 agonist antibody, ImPACT, ComPACT and ImPACT+OX40 agonist antibody combination treated groups, indicating immune cell activation and tumor infiltration. As expected, only mice receiving OX40 agonist antibodies (either alone or together with ImPACT) showed increased CD4 and FoxP3 expression within the tumor (FIG. 11B). CT26 antigen-specific CD8+ expansion, as detected by AH1-tetramer staining, was significantly elevated approximately 4-fold in ImPACT+OX40 antibody and approximately 5-fold in ComPACT treated mice compared with the untreated group (FIG. 11B). Tumor progression was shown to be strongly blocked in mice receiving either ImPACT+OX40 agonist or ComPACT treatments as compared to the control or monotherapy arms (FIG. 11D). This led to a significant increase in long-term survival and a higher rate of complete tumor rejection in ComPACT treated mice (FIG. 11E, 80% and approximately 47%, respectively) compared to what we observed with the B16.F10 tumor model. Accordingly, ComPACT generates potent antigen-specific T cell expansion and tumor infiltration, delays in tumor growth and significant survival benefits.

The B16.F10 mouse melanoma tumor model is an aggressive tumor and is not typically treated effectively with OX40 agonist antibody. In order to assess gp96-Ig based vaccines in the B16.F10 tumor model, a B16.F10-ova cell line was generated. In addition, B16.F10-ova-ImPACT and -ComPACT vaccines were subsequently generated by stable transfection of gp96-Ig and gp96-Ig-Fc-OX40L vectors, respectively. Comparable levels of gp96-Ig secretion from the B16.F10-ImPACT and -ComPACT cell lines were confirmed by ELISA and Fc-OX40L expression in the B16.F10-ova-ComPACT cell line was also confirmed by qRT-PCR. Mice were adoptively transferred with OT-I cells a day prior to B16.F10-ova tumor inoculation (indicating day −1, FIG. 12A). Next, the antigen specific response of OT-I cells was investigated in mice following vaccination on days 4, 7 and 10 with mitomycin-C treated B16. F10-ova cells, B16. F10-ova-ImPACT, B16. F10-ova-ImPACT combined with OX40 agonist antibodies or with B16.F10-ova-ComPACT (FIG. 12B). Consistent with the data obtained with the 3T3-ova model system, B16.F10-ova-ComPACT treated mice exhibited a robust expansion of OT-I cells between days 10 and 19 (which corresponded to days 6 through 15 following the initial vaccination), that was greater than that seen with ImPACT+/−OX40 agonist antibodies, with similar durable kinetics in the contraction phase to what was observed previously. Accordingly, B16.F10-ova-ComPACT vaccinated mice displayed a more potent anti-tumor effect than both ImPACT+/−OX40 agonist antibody vaccinations (FIG. 12C). The long term survival in ComPACT treated mice was approximately 78%, with 11% of the mice demonstrating complete rejection of their aggressive tumors. In comparison ImPACT alone vaccinated mice and ImPACT+OX40 agonist Ab treated mice showed overall survival rates of 50% and 62.5%, respectively (FIG. 12D).

Figure 13:
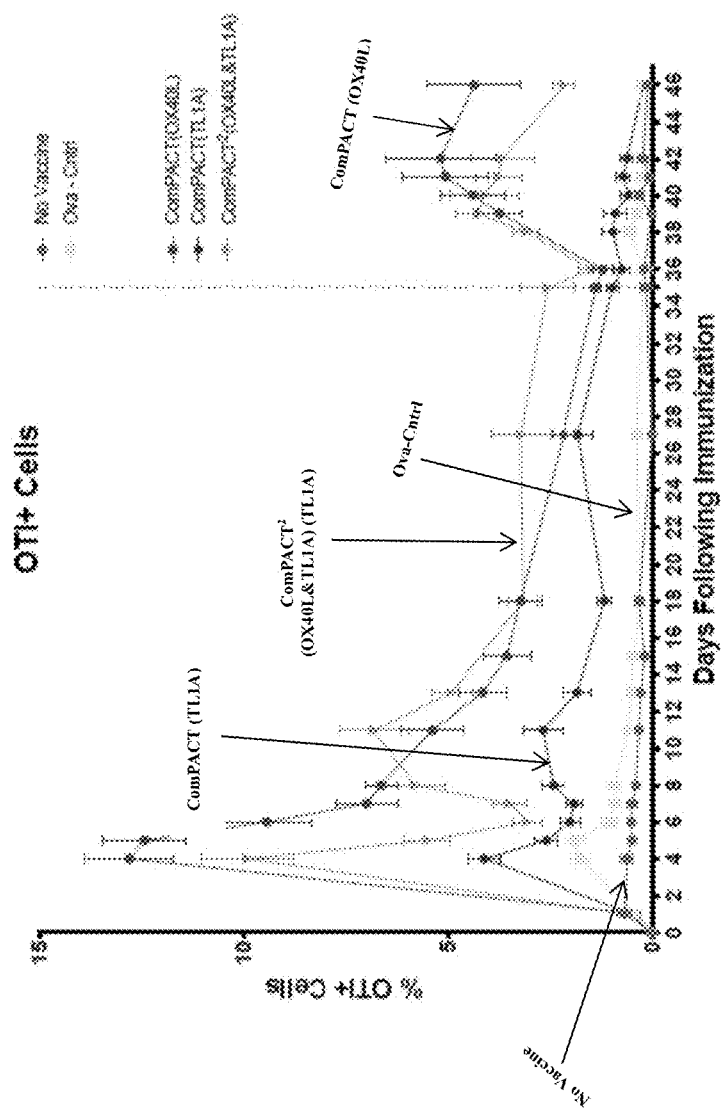
FIG. 13 is a graph plotting the OT-1 expansion timecourse (similar to FIGS. 5D and 6C), using FOXP3-RFP mice seeded with OT-1 (CD8) cells on day −1. OT-1/GFP cells were analyzed by flow cytometry in mice treated with No Vaccine, Ova only control cells, ComPACT (96-Ig/OX40L or gp96-Ig/TL1A) or ComPACT$^2$ (96-Ig/OX40L+TL1A), over 46 days, with initial vaccination on day 0 and a boost on day 35. Plotted values represent the mean and error is SEM. ComPACT² (gp96-Ig/OX40L+TL1A) represents a combination injection including ComPACT-OX40L and ComPACT-TL1A (i.e., two different cell lines in the same syringe).
Figure 14:
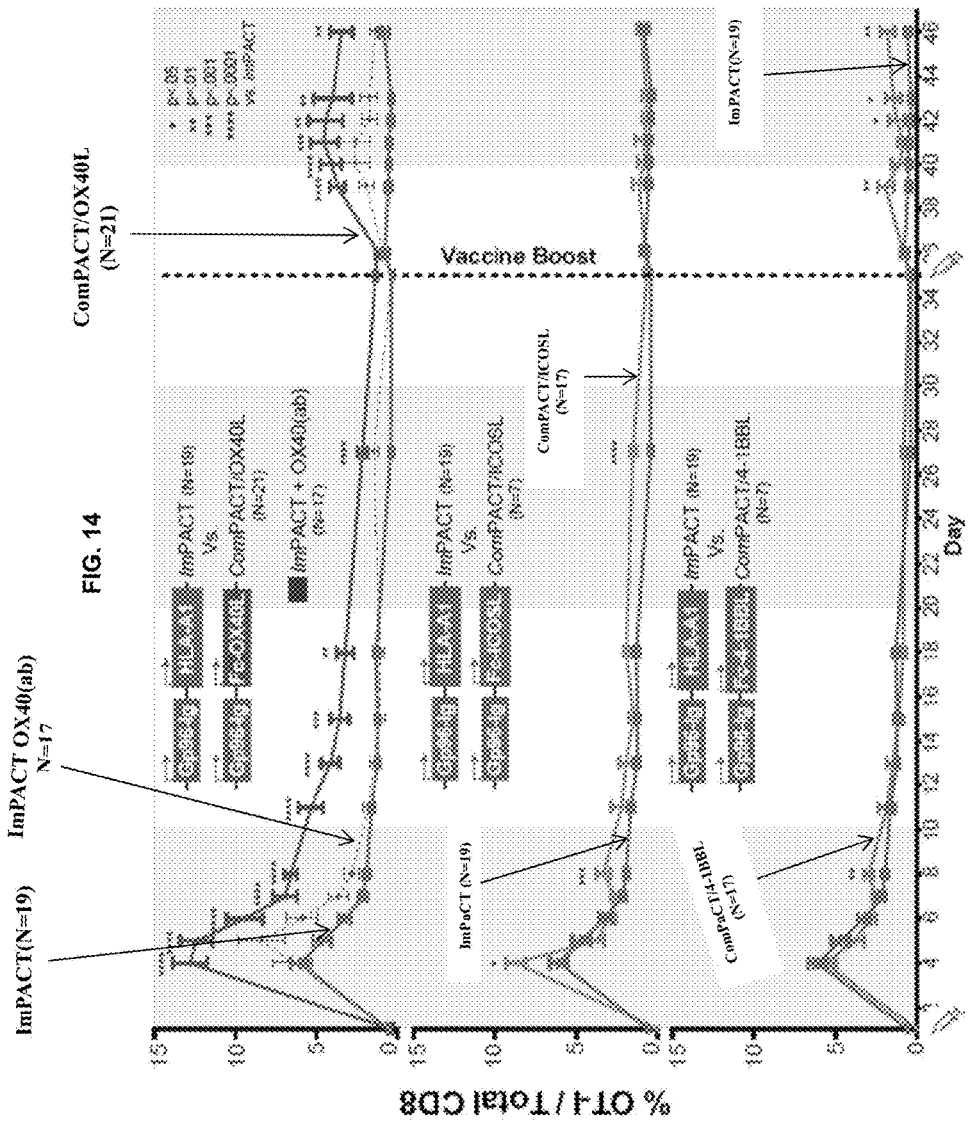
FIG. 14 is a graph showing the effects of ComPACT on the proliferation and activation of ovalbumin specific CD8+ T cells (OTI). C57BL/6 mice were immunized with ImPACT alone or ComPACT (gp96-Ig/OX40L), ComPACT (96-Ig/4-ICOSL), or ComPACT (gp96-Ig/4-1BBL) at day 0. The frequency of OT-I was monitored in the peripheral blood on the indicated days.

The functional activities of additional ComPACTs were investigated using the previously described immunization assay as well as the OT-I transfer assay. Specifically, OT-1/GFP cells were analyzed by flow cytometry in mice treated with No Vaccine, Ova only control cells, ComPACT (gp96-Ig/OX40L or gp96-Ig/TL1A) or ComPACT$^2$ (gp96-Ig/OX40L+TL1A), which is a mixture of a ComPACT-OX40L cell line and a ComPACT-TL1A cell line, over 46 days, with initial vaccination on day 0 and a boost on day 35 (FIG. 13). Both prime and memory responses were strong in mice treated with ComPACT (96-Ig/OX40L or gp96-Ig/TL1A) or ComPACT$^2$ (gp96-Ig/OX40L+TL1A). ComPACT or ComPACT$^2$ mice also surprisingly retained elevated OT-1 levels throughout the time-course (~days 7-20). Additionally, C57BL/6 mice were immunized with ImPACT alone or ComPACT (gp96-OX40L, gp96-Ig/4-1BBL or gp96-Ig/ICOS-L) at day 0 (FIG. 14). Results indicate that the various ComPACTS enhanced the proliferation of OTI cells compared to ImPACT.

The in vivo activities of the additional ComPACTS were further investigated in the CT26 colorectal carcinoma model. Specifically, mice were either untreated or vaccinated on days 4, 7 and 10 with CT26 parental cells, ImPACT alone, ImPACT+the TNFRSF25 agonist (4C12 ab), 4C12 (ab) alone, PD-1 (ab) alone, 4C12 (ab) and PD-1 (ab), ComPACT (gp96-Ig/OX40L or gp96-Ig/TL1A), ComPACT (gp96-Ig/OX40L)+PD-1 (ab), or ComPACT$^2$ (gp96-Ig/OX40L+TL1A) (FIG. 15). Results indicate that ComPACT treatment alone (gp96-Ig/OX40L or gp96-Ig/TL1A) and in combination with PD-1 significantly reduced tumor growth. As shown in FIG. 16, ComPACT treatment alone (gp96-Ig/OX40L or gp96-Ig/TL1A) and in combination with PD-1 also significantly enhanced mice survival.

Expression of ComPACT in human cancer cell lines was tested. Specifically, ComPACT (gp96-Ig/OX40L) was transfected into a human prostate cancer cell line (e.g., PC-3) or a human lung adenocarcinoma cell line (e.g., AD100). See FIGS. 17 and 18, respectively. Results indicate that both cell lines produced and excreted OX40L.

Altogether, these data demonstrated that combination immunotherapy may be approached by incorporating multiple complementary modalities, in this case a vaccine and T cell costimulatory fusion protein, in a single compound. Provision of T cell costimulation by vector-encoded and cell-secreted Fc-OX40L was feasible, and led to enhanced proliferation of antigen-specific CD8+ T cells at the time of both priming and boosting as compared to OX40 agonistic antibodies. T cells activated by the combined vaccine and costimulator produced IFNγ, IL-2, TNFα, and granzyme-B, and were not accompanied by off-target T cell proliferation and systemic inflammatory cytokine increases observed with OX40 agonist antibodies. Importantly, this approach also enhanced therapeutic tumor immunity in an established murine colon cancer model. Together, these results provide a strategy for implementing combination immunotherapy that may not rely on double or triple antibody combinations, and which may provide greater safety and efficacy for patients due to reduced off-target T cell activation.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The content of any individual section may be equally applicable to all sections.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in anyway.

The invention claimed is:

1. An expression vector comprising a first nucleotide sequence that encodes a secretable gp96-Ig fusion protein, and a second nucleotide sequence that encodes a T cell costimulatory fusion protein comprising OX40L-Ig, wherein:
the OX40L-Ig fusion protein comprises SEQ ID NO:11 and
enhances activation of antigen-specific T cells when administered to a subject.

2. The expression vector of claim 1, wherein the vector is a mammalian expression vector.

3. The expression vector of claim 1, wherein the gp96-Ig fusion protein lacks the gp96 KDEL (SEQ ID NO:3) sequence.

4. The expression vector of claim 3, wherein the Ig tag in the gp96-Ig fusion protein comprises the Fc region of human IgGl, IgG2, IgG3, or IgG4.

5. The expression vector of claim 1, wherein the expression vector comprises DNA.

6. The expression vector of claim 1, wherein the expression vector comprises RNA.

7. The expression vector of claim 1, wherein the expression vector is incorporated into a virus or virus-like particle.

8. The expression vector of claim 1, wherein the expression vector is incorporated into a human tumor cell.

9. The composition of claim 8, wherein the human tumor cell is a cell from an established NSCLC, bladder cancer, melanoma, ovarian cancer, renal cell carcinoma, prostate carcinoma, sarcoma, breast carcinoma, squamous cell carcinoma, head and neck carcinoma, hepatocellular carcinoma, pancreatic carcinoma, or colon carcinoma cell line.

10. The expression vector of claim 1, wherein the gp96 of the said gp96-Ig fusion comprises the first 799 amino acids of SEQ ID NO: 2, such that it lacks a C-terminal KDEL (SEQ ID NO:3) sequence.

11. The expression vector of claim 1, wherein the Ig tag of said gp96-Ig is a CH2-CH3 domain of a human IgG.

12. The expression vector of claim 11, wherein said human IgG is human IgG1.

13. A human tumor cell comprising the expression vector of claim 1.

* * * * *

SEQUENCE LISTING

<160> NUMBER OF SEQ ID NOS: 49

<210> SEQ ID NO 1
<211> LENGTH: 2412
<212> TYPE: DNA
<213> ORGANISM: Homo sapiens

<400> SEQUENCE: 1

| | | | | | |
|---|---|---|---|---|---|
| atgagggccc | tgtgggtgct | gggcctctgc | tgcgtcctgc | tgaccttcgg | gtcggtcaga | 60 |
| gctgacgatg | aagttgatgt | ggatggtaca | gtagaagagg | atctgggtaa | aagtagagaa | 120 |
| ggatcaagga | cggatgatga | agtagtacag | agagaggaag | aagctattca | gttggatgga | 180 |
| ttaaatgcat | cacaaataag | agaacttaga | gagaagtcgg | aaaagtttgc | cttccaagcc | 240 |
| gaagttaaca | gaatgatgaa | acttatcatc | aattcattgt | ataaaaataa | agagattttc | 300 |
| ctgagagaac | tgatttcaaa | tgcttctgat | gctttagata | agataaggct | aatatcactg | 360 |
| actgatgaaa | atgctctttc | tggaaatgag | gaactaacag | tcaaaattaa | gtgtgataag | 420 |
| gagaagaacc | tgctgcatgt | cacagacacc | ggtgtaggaa | tgaccagaga | agagttggtt | 480 |
| aaaaaccttg | gtaccatagc | caaatctggg | acaagcgagt | ttttaaacaa | aatgactgaa | 540 |
| gcacaggaag | atggccagtc | aacttctgaa | ttgattggcc | agtttggtgt | cggtttctat | 600 |
| tccgccttcc | ttgtagcaga | taaggttatt | gtcacttcaa | aacacaacaa | cgatacccag | 660 |
| cacatctggg | agtctgactc | caatgaattt | tctgtaattg | ctgacccaag | aggaaacact | 720 |
| ctaggacggg | gaacgacaat | tacccttgtc | ttaaaagaag | aagcatctga | ttaccttgaa | 780 |
| ttggatacaa | ttaaaaatct | cgtcaaaaaa | tattcacagt | tcataaactt | tcctatttat | 840 |
| gtatggagca | gcaagactga | aactgttgag | gagcccatgg | aggaagaaga | agcagccaaa | 900 |
| gaagagaaag | aagaatctga | tgatgaagct | gcagtagagg | aagaagaaga | agaaaagaaa | 960 |
| ccaaagacta | aaaaagttga | aaaaactgtc | tgggactggg | aacttatgaa | tgatatcaaa | 1020 |
| ccaatatggc | agagaccatc | aaaagaagta | gaagaagatg | aatacaaagc | tttctacaaa | 1080 |
| tcattttcaa | aggaaagtga | tgaccccatg | gcttatattc | actttactgc | tgaaggggaa | 1140 |
| gttaccttca | aatcaatttt | atttgtaccc | acatctgctc | cacgtggtct | gtttgacgaa | 1200 |
| tatggatcta | aaaagagcga | ttacattaag | ctctatgtgc | gccgtgtatt | catcacagac | 1260 |
| gacttccatg | atatgatgcc | taaatacctc | aattttgtca | agggtgtggt | ggactcagat | 1320 |
| gatctcccct | tgaatgtttc | ccgcgagact | cttcagcaac | ataaactgct | taaggtgatt | 1380 |

-continued

```
aggaagaagc ttgttcgtaa aacgctggac atgatcaaga agattgctga tgataaatac    1440
aatgatactt tttggaaaga atttggtacc aacatcaagc ttggtgtgat tgaagaccac    1500
tcgaatcgaa cacgtcttgc taaacttctt aggttccagt cttctcatca tccaactgac    1560
attactagcc tagaccagta tgtggaaaga atgaaggaaa acaagacaaa atctacttc    1620
atggctgggt ccagcagaaa agaggctgaa tcttctccat ttgttgagcg acttctgaaa    1680
aagggctatg aagttattta cctcacagaa cctgtggatg aatactgtat tcaggcccttt  1740
cccgaatttg atgggaagag gttccagaat gttgccaagg aaggagtgaa gttcgatgaa    1800
agtgagaaaa ctaaggagag tcgtgaagca gttgagaaaa atttgagcc tctgctgaat    1860
tggatgaaag ataaagccct taaggacaag attgaaaagg ctgtggtgtc tcagcgcctg    1920
acagaatctc cgtgtgcttt ggtggccagc cagtacggat ggtctggcaa catggagaga    1980
atcatgaaag cacaagcgta ccaaacgggc aaggacatct ctacaaatta ctatgcgagt    2040
cagaagaaaa catttgaaat taatcccaga cacccgctga tcagagacat gcttcgacga    2100
attaaggaag atgaagatga taaaacagtt ttggatcttg ctgtggtttt gtttgaaaca    2160
gcaacgcttc ggtcagggta tcttttacca gacactaaag catatggaga tagaatagaa    2220
agaatgcttc gcctcagttt gaacattgac cctgatgcaa aggtggaaga gagcccgaa    2280
gaagaacctg aagagacagc agaagacaca acagaagaca cagagcaaga cgaagatgaa    2340
gaaatggatg tgggaacaga tgaagaagaa gaaacagcaa ggaatctac agctgaaaaa     2400
gatgaattgt aa                                                       2412

<210> SEQ ID NO 2
<211> LENGTH: 803
<212> TYPE: PRT
<213> ORGANISM: Homo sapiens

<400> SEQUENCE: 2

Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Ala Ile Gln Leu Asp Gly Leu Asn Ala Ser
    50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190
```

```
Gly Gln Phe Gly Val Gly Phe Tyr Ser Ala Phe Leu Val Ala Asp Lys
            195                 200                 205

Val Ile Val Thr Ser Lys His Asn Asn Asp Thr Gln His Ile Trp Glu
210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
                260                 265                 270

Gln Phe Ile Asn Phe Pro Ile Tyr Val Trp Ser Ser Lys Thr Glu Thr
            275                 280                 285

Val Glu Glu Pro Met Glu Glu Glu Ala Ala Lys Glu Glu Lys Glu
        290                 295                 300

Glu Ser Asp Asp Glu Ala Ala Val Glu Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
            340                 345                 350

Asp Glu Tyr Lys Ala Phe Tyr Lys Ser Phe Ser Lys Glu Ser Asp Asp
            355                 360                 365

Pro Met Ala Tyr Ile His Phe Thr Ala Glu Gly Glu Val Thr Phe Lys
        370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
                405                 410                 415

Phe Ile Thr Asp Asp Phe His Asp Met Met Pro Lys Tyr Leu Asn Phe
            420                 425                 430

Val Lys Gly Val Val Asp Ser Asp Asp Leu Pro Leu Asn Val Ser Arg
        435                 440                 445

Glu Thr Leu Gln Gln His Lys Leu Leu Lys Val Ile Arg Lys Lys Leu
    450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
            500                 505                 510

Gln Ser Ser His His Pro Thr Asp Ile Thr Ser Leu Asp Gln Tyr Val
            515                 520                 525

Glu Arg Met Lys Glu Lys Gln Asp Lys Ile Tyr Phe Met Ala Gly Ser
        530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Val Ala
            580                 585                 590

Lys Glu Gly Val Lys Phe Asp Glu Ser Glu Lys Thr Lys Glu Ser Arg
            595                 600                 605
```

```
Glu Ala Val Glu Lys Glu Phe Glu Pro Leu Leu Asn Trp Met Lys Asp
            610                 615                 620
Lys Ala Leu Lys Asp Lys Ile Glu Lys Ala Val Val Ser Gln Arg Leu
625                 630                 635                 640
Thr Glu Ser Pro Cys Ala Leu Val Ala Ser Gln Tyr Gly Trp Ser Gly
                645                 650                 655
Asn Met Glu Arg Ile Met Lys Ala Gln Ala Tyr Gln Thr Gly Lys Asp
            660                 665                 670
Ile Ser Thr Asn Tyr Tyr Ala Ser Gln Lys Lys Thr Phe Glu Ile Asn
            675                 680                 685
Pro Arg His Pro Leu Ile Arg Asp Met Leu Arg Arg Ile Lys Glu Asp
        690                 695                 700
Glu Asp Asp Lys Thr Val Leu Asp Leu Ala Val Val Leu Phe Glu Thr
705                 710                 715                 720
Ala Thr Leu Arg Ser Gly Tyr Leu Leu Pro Asp Thr Lys Ala Tyr Gly
                725                 730                 735
Asp Arg Ile Glu Arg Met Leu Arg Leu Ser Leu Asn Ile Asp Pro Asp
            740                 745                 750
Ala Lys Val Glu Glu Pro Glu Glu Pro Glu Glu Thr Ala Glu
            755                 760                 765
Asp Thr Thr Glu Asp Thr Glu Gln Asp Glu Asp Glu Met Asp Val
        770                 775                 780
Gly Thr Asp Glu Glu Glu Thr Ala Lys Glu Ser Thr Ala Glu Lys
785                 790                 795                 800
Asp Glu Leu

<210> SEQ ID NO 3
<211> LENGTH: 4
<212> TYPE: PRT
<213> ORGANISM: Homo sapiens

<400> SEQUENCE: 3

Lys Asp Glu Leu
1

<210> SEQ ID NO 4
<211> LENGTH: 1455
<212> TYPE: DNA
<213> ORGANISM: Artificial Sequence
<220> FEATURE:
<223> OTHER INFORMATION: Synthetic sequence

<400> SEQUENCE: 4
atgagactgg gaagccctgg cctgctgttt ctgctgttca gcagcctgag agccgacacc      60
caggaaaaag aagtgcgggc catggtggga agcgacgtgg aactgagctg cgcctgtcct     120
gagggcagca gattcgacct gaacgacgtg tacgtgtact ggcagaccag cgagagcaag     180
accgtcgtga cctaccacat cccccagaac agctccctgg aaaacgtgga cagccggtac     240
agaaaccggg ccctgatgtc tcctgccggc atgctgagag gcgacttcag cctgcggctg     300
ttcaacgtga cccccaggac gagcagaaa ttccactgcc tggtgctgag ccagagcctg     360
ggcttccagg aagtgctgag cgtggaagtg acactgcacg tggccgccaa tttcagcgtg     420
ccagtggtgt ctgcccccca gcccttcct caggatgagc tgaccttcac ctgtaccagc     480
atcaacggct accccagacc caatgtgtac tggatcaaca agaccgacaa cagcctgctg     540
gaccaggccc tgcagaacga taccgtgttc ctgaacatgc ggggcctgta cgacgtggtg     600
```

```
tccgtgctga gaatcgccag aaccccagc gtgaacatcg gctgctgcat cgagaacgtg      660
ctgctgcagc agaacctgac cgtgggcagc cagaccggca acgacatcgg cgagagagac      720
aagatcaccg agaaccccgt gtccaccggc gagaagaatg ccgccacctc taagtacggc      780
cctccctgcc cttcttgccc agccctgaa tttctgggcg acccctccgt gtttctgttc      840 ccccaaagc ccaaggacac cctgatgatc agccggaccc ccgaagtgac ctgcgtggtg      900
gtggatgtgt cccaggaaga tcccgaggtg cagttcaatt ggtacgtgga cggggtggaa      960
gtgcacaacg ccaagaccaa gcccagagag gaacagttca acagcaccta ccgggtggtg     1020
tctgtgctga ccgtgctgca ccaggattgg ctgagcggca agagtacaa gtgcaaggtg     1080 tccagcaagg gcctgcccag cagcatcgaa aagaccatca gcaacgccac cggccagccc     1140
agggaacccc aggtgtacac actgccccct agccaggaag atgaccaa gaaccaggtg     1200 tccctgacct gtctcgtgaa gggcttctac ccctccgata tcgccgtgga atgggagagc     1260
aacggccagc cagagaacaa ctacaagacc ccccccag tgctggacag cgacggctca     1320
ttcttcctgt actcccggct gacagtggac aagagcagct ggcaggaagg caacgtgttc     1380
agctgcagcg tgatgcacga agccctgcac aaccactaca cccagaagtc cctgtctctg     1440
tccctgggca atga                                                       1455
```

<210> SEQ ID NO 5
<211> LENGTH: 484
<212> TYPE: PRT
<213> ORGANISM: Artificial Sequence
<220> FEATURE:
<223> OTHER INFORMATION: Synthetic sequence

<400> SEQUENCE: 5

```
Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
            20                  25                  30

Val Glu Leu Ser Cys Ala Cys Pro Glu Gly Ser Arg Phe Asp Leu Asn
        35                  40                  45

Asp Val Tyr Val Tyr Trp Gln Thr Ser Glu Ser Lys Thr Val Val Thr
    50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
    130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
        195                 200                 205
```

```
Pro Ser Val Asn Ile Gly Cys Cys Ile Glu Asn Val Leu Leu Gln Gln
    210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Ser Lys Tyr Gly Pro Pro Cys Pro Ser Cys Pro Ala Pro Glu Phe Leu
                260                 265                 270

Gly Gly Pro Ser Val Phe Leu Phe Pro Pro Lys Pro Lys Asp Thr Leu
            275                 280                 285

Met Ile Ser Arg Thr Pro Glu Val Thr Cys Val Val Val Asp Val Ser
290                 295                 300

Gln Glu Asp Pro Glu Val Gln Phe Asn Trp Tyr Val Asp Gly Val Glu
305                 310                 315                 320

Val His Asn Ala Lys Thr Lys Pro Arg Glu Glu Gln Phe Asn Ser Thr
                325                 330                 335

Tyr Arg Val Val Ser Val Leu Thr Val Leu His Gln Asp Trp Leu Ser
                340                 345                 350

Gly Lys Glu Tyr Lys Cys Lys Val Ser Ser Lys Gly Leu Pro Ser Ser
            355                 360                 365

Ile Glu Lys Thr Ile Ser Asn Ala Thr Gly Gln Pro Arg Glu Pro Gln
370                 375                 380

Val Tyr Thr Leu Pro Pro Ser Gln Glu Glu Met Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
                420                 425                 430

Pro Val Leu Asp Ser Asp Gly Ser Phe Phe Leu Tyr Ser Arg Leu Thr
            435                 440                 445

Val Asp Lys Ser Ser Trp Gln Glu Gly Asn Val Phe Ser Cys Ser Val
450                 455                 460

Met His Glu Ala Leu His Asn His Tyr Thr Gln Lys Ser Leu Ser Leu
465                 470                 475                 480

Ser Leu Gly Lys

<210> SEQ ID NO 6
<211> LENGTH: 1305
<212> TYPE: DNA
<213> ORGANISM: Artificial Sequence
<220> FEATURE:
<223> OTHER INFORMATION: Synthetic sequence

<400> SEQUENCE: 6
atgtctaagt acggccctcc ctgccctagc tgccctgccc ctgaatttct gggcggaccc      60
agcgtgttcc tgttcccccc aaagcccaag gacaccctga tgatcagccg gacccccgaa     120
gtgacctgcg tggtggtgga tgtgtcccag gaagatcccg aggtgcagtt caattggtac     180
gtggacggcg tggaagtgca caacgccaag accaagccca gagaggaaca gttcaacagc     240
acctaccggg tggtgtccgt gctgaccgtg ctgcaccagg attggctgag cggcaaagag     300
tacaagtgca aggtgtccag caagggcctg cccagcagca tcgagaaaac catcagcaac     360
gccaccggcc agcccaggga accccaggtg tacacactgc ccctagcca ggaagagatg      420 accaagaacc aggtgtccct gacctgtctc gtgaagggct tctacccctc cgatatcgcc     480
```

```
gtggaatggg agagcaacgg ccagcctgag aacaactaca agaccacccc cccagtgctg    540
gacagcgacg gctcattctt cctgtacagc agactgaccg tggacaagag cagctggcag    600
gaaggcaacg tgttcagctg cagcgtgatg cacgaggccc tgcacaacca ctacacccag    660
aagtccctgt ctctgagcct gggcaaggcc tgtccatggg ctgtgtctgg cgctagagcc    720
tctcctggat ctgccgccag ccccagactg agagagggac ctgagctgag ccccgatgat    780
cctgccggac tgctggatct gagacagggc atgttcgccc agctggtggc ccagaacgtg    840
ctgctgatcg atggccccct gagctggtac agcgatcctg gactggctgg cgtgtcactg    900
acaggcggcc tgagctacaa agaggacacc aaagaactgg tggtggccaa ggccggcgtg    960
tactacgtgt tctttcagct ggaactgcgg agagtggtgg ccggcgaagg atccggctct    1020
gtgtctctgg ctctgcatct gcagcccctg agatctgctg ctggcgctgc tgctctggcc    1080
ctgacagtgg acctgcctcc tgcctctagc gaggccagaa acagcgcatt cgggtttcaa    1140
ggcagactgc tgcacctgtc tgccggccag agactgggag tgcatctgca cacagaggcc    1200
agagccaggc acgcctggca gctgactcag ggcgctacag tgctgggcct gttcagagtg    1260 accccccgaga ttccagccgg cctgcctagc cccagatccg aatga                    1305
```

<210> SEQ ID NO 7
<211> LENGTH: 434
<212> TYPE: PRT
<213> ORGANISM: Artificial Sequence
<220> FEATURE:
<223> OTHER INFORMATION: Synthetic sequence

<400> SEQUENCE: 7

```
Met Ser Lys Tyr Gly Pro Pro Cys Pro Ser Cys Pro Ala Pro Glu Phe
 1               5                  10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
 65                  70                  75                  80

Thr Tyr Arg Val Val Ser Val Leu Thr Val Leu His Gln Asp Trp Leu
                85                  90                  95

Ser Gly Lys Glu Tyr Lys Cys Lys Val Ser Ser Lys Gly Leu Pro Ser
            100                 105                 110

Ser Ile Glu Lys Thr Ile Ser Asn Ala Thr Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Ser Trp Gln Glu Gly Asn Val Phe Ser Cys Ser
        195                 200                 205

Val Met His Glu Ala Leu His Asn His Tyr Thr Gln Lys Ser Leu Ser
    210                 215                 220
```

```
Leu Ser Leu Gly Lys Ala Cys Pro Trp Ala Val Ser Gly Ala Arg Ala
225                 230                 235                 240

Ser Pro Gly Ser Ala Ala Ser Pro Arg Leu Arg Glu Gly Pro Glu Leu
            245                 250                 255

Ser Pro Asp Asp Pro Ala Gly Leu Leu Asp Leu Arg Gln Gly Met Phe
        260                 265                 270

Ala Gln Leu Val Ala Gln Asn Val Leu Leu Ile Asp Gly Pro Leu Ser
    275                 280                 285

Trp Tyr Ser Asp Pro Gly Leu Ala Gly Val Ser Leu Thr Gly Gly Leu
290                 295                 300

Ser Tyr Lys Glu Asp Thr Lys Glu Leu Val Ala Lys Ala Gly Val
305                 310                 315                 320

Tyr Tyr Val Phe Phe Gln Leu Glu Leu Arg Arg Val Val Ala Gly Glu
                325                 330                 335

Gly Ser Gly Ser Val Ser Leu Ala Leu His Leu Gln Pro Leu Arg Ser
            340                 345                 350

Ala Ala Gly Ala Ala Ala Leu Ala Leu Thr Val Asp Leu Pro Pro Ala
        355                 360                 365

Ser Ser Glu Ala Arg Asn Ser Ala Phe Gly Phe Gln Gly Arg Leu Leu
    370                 375                 380

His Leu Ser Ala Gly Gln Arg Leu Gly Val His Leu His Thr Glu Ala
385                 390                 395                 400

Arg Ala Arg His Ala Trp Gln Leu Thr Gln Gly Ala Thr Val Leu Gly
                405                 410                 415

Leu Phe Arg Val Thr Pro Glu Ile Pro Ala Gly Leu Pro Ser Pro Arg
            420                 425                 430

Ser Glu

<210> SEQ ID NO 8
<211> LENGTH: 1284
<212> TYPE: DNA
<213> ORGANISM: Artificial Sequence
<220> FEATURE:
<223> OTHER INFORMATION: Synthetic sequence

<400> SEQUENCE: 8
atgtctaagt acggccctcc ctgccctagc tgccctgccc ctgaatttct gggcggaccc        60
agcgtgttcc tgttcccccc aaagcccaag acaccctga tgatcagccg gaccccgaa       120 gtgacctgcg tggtggtgga tgtgtcccag gaagatcccg aggtgcagtt caattggtac       180
gtggacggcg tggaagtgca caacgccaag accaagccca gagaggaaca gttcaacagc       240
acctaccggg tggtgtccgt gctgaccgtg ctgcaccagg attggctgag cggcaaagag       300
tacaagtgca aggtgtccag caagggcctg cccagcagca tcgagaaaac catcagcaac       360
gccaccggcc agcccaggga accccaggtg tacacactgc ccctagcca ggaagagatg       420 accaagaacc aggtgtccct gacctgtctc gtgaagggct ctaccccctc cgatatcgcc       480
gtggaatggg agagcaacgg ccagcctgag aacaactaca agaccacccc cccagtgctg       540
gacagcgacg gctcattctt cctgtacagc agactgaccg tggacaagag cagctggcag       600
gaaggcaacg tgttcagctg cagcgtgatg cacgaggccc tgcacaacca ctacacccag       660
aagtccctgt ctctgagcct gggcaagatc gagggccgga tggatagagc ccagggcgaa       720
gcctgcgtgc agttccaggc tctgaagggc caggaattcg cccccagcca ccagcaggtg       780
tacgccccct ctgagagccga cggcgataag cctagagccc acctgacagt cgtgcggcag       840
```

```
acccctaccc agcacttcaa gaatcagttc cccgccctgc actgggagca cgaactgggc      900
ctggccttca ccaagaacag aatgaactac accaacaagt ttctgctgat ccccgagagc      960
ggcgactact tcatctacag ccaagtgacc ttccggggca tgaccagcga gtgcagcgag     1020
atcagacagg ccggcagacc taacaagccc gacagcatca ccgtcgtgat caccaaagtg     1080
accgacagct accccgagcc cacccagctg ctgatgggca ccaagagcgt gtgcgaagtg     1140
ggcagcaact ggttccagcc catctacctg ggcgccatgt ttagtctgca agagggcgac     1200
aagctgatgg tcaacgtgtc cgacatcagc ctggtggatt acaccaaaga ggacaagacc     1260
ttcttcggcg cctttctgct ctga                                            1284
```

<210> SEQ ID NO 9  
<211> LENGTH: 427  
<212> TYPE: PRT  
<213> ORGANISM: Artificial Sequence  
<220> FEATURE:  
<223> OTHER INFORMATION: Synthetic sequence

<400> SEQUENCE: 9

```
Met Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Ser Gly Lys Glu Tyr Lys Cys Lys Val Ser Ser Lys Gly Leu Pro Ser
            100                 105                 110

Ser Ile Glu Lys Thr Ile Ser Asn Ala Thr Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Ser Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Ile Glu Gly Arg Met Asp Arg Ala Gln Gly Glu
225                 230                 235                 240

Ala Cys Val Gln Phe Gln Ala Leu Lys Gly Gln Glu Phe Ala Pro Ser
                245                 250                 255

His Gln Gln Val Tyr Ala Pro Leu Arg Ala Asp Gly Asp Lys Pro Arg
            260                 265                 270

Ala His Leu Thr Val Val Arg Gln Thr Pro Thr Gln His Phe Lys Asn
```

```
                    275                 280                 285
        Gln Phe Pro Ala Leu His Trp Glu His Glu Leu Gly Leu Ala Phe Thr
                290                 295                 300

Lys Asn Arg Met Asn Tyr Thr Asn Lys Phe Leu Leu Ile Pro Glu Ser
        305                 310                 315                 320

Gly Asp Tyr Phe Ile Tyr Ser Gln Val Thr Phe Arg Gly Met Thr Ser
                        325                 330                 335

Glu Cys Ser Glu Ile Arg Gln Ala Gly Arg Pro Asn Lys Pro Asp Ser
                    340                 345                 350

Ile Thr Val Val Ile Thr Lys Val Thr Asp Ser Tyr Pro Glu Pro Thr
                355                 360                 365

Gln Leu Leu Met Gly Thr Lys Ser Val Cys Glu Val Gly Ser Asn Trp
            370                 375                 380

Phe Gln Pro Ile Tyr Leu Gly Ala Met Phe Ser Leu Gln Glu Gly Asp
        385                 390                 395                 400

Lys Leu Met Val Asn Val Ser Asp Ile Ser Leu Val Asp Tyr Thr Lys
                        405                 410                 415

Glu Asp Lys Thr Phe Phe Gly Ala Phe Leu Leu
                    420                 425

<210> SEQ ID NO 10
<211> LENGTH: 1107
<212> TYPE: DNA
<213> ORGANISM: Artificial Sequence
<220> FEATURE:
<223> OTHER INFORMATION: Synthetic sequence

<400> SEQUENCE: 10
atgtctaagt acggccctcc ctgccctagc tgccctgccc ctgaatttct gggcggaccc      60
agcgtgttcc tgttcccccc aaagcccaag acaccctga  tgatcagccg gaccccgaa     120 gtgacctgcg tggtggtgga tgtgtcccag gaagatcccg aggtgcagtt caattggtac    180
gtggacggcg tggaagtgca caacgccaag accaagccca gagaggaaca gttcaacagc    240
acctaccggg tggtgtccgt gctgaccgtg ctgcaccagg attggctgag cggcaaagag    300
tacaagtgca aggtgtccag caagggcctg cccagcagca tcgagaaaac catcagcaac    360
gccaccggcc agcccaggga accccaggtg tacacactgc ccctagcca ggaagagatg     420 accaagaacc aggtgtccct gacctgtctc gtgaagggct  tctacccctc cgatatcgcc   480
gtggaatggg agagcaacgg ccagcctgag aacaactaca agaccacccc cccagtgctg    540
gacagcgacg gctcattctt cctgtacagc agactgaccg tggacaagag cagctggcag    600
gaaggcaacg tgttcagctg cagcgtgatg cacgaggccc tgcacaacca ctacacccag    660
aagtccctgt ctctgagcct gggcaagatc gagggccgga tggatcaggt gtcacacaga    720 taccccccgga tccagagcat caaagtgcag tttaccgagt acaagaaaga agggcttt     780 atcctgacca gccagaaaga ggacgagatc atgaaggtgc agaacaacag cgtgatcatc    840
aactgcgacg ggttctacct gatcagcctg aagggctact cagtcagga agtgaacatc     900 agcctgcact accagaagga cgaggaaccc ctgttccagc tgaagaaagt gcggagcgtg    960
aacagcctga tggtggcctc tctgacctac aaggacaagg tgtacctgaa cgtgaccacc   1020
gacaacacca gcctggacga cttccacgtg aacggcggcg agctgatcct gattcaccag   1080
aaccccggcg agttctgcgt gctctga                                       1107

<210> SEQ ID NO 11
```

<211> LENGTH: 368
<212> TYPE: PRT
<213> ORGANISM: Artificial Sequence
<220> FEATURE:
<223> OTHER INFORMATION: Synthetic sequence

<400> SEQUENCE: 11

```
Met Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Ser Gly Lys Glu Tyr Lys Cys Lys Val Ser Ser Lys Gly Leu Pro Ser
            100                 105                 110

Ser Ile Glu Lys Thr Ile Ser Asn Ala Thr Gly Gln Pro Arg Glu Pro
        115                 120                 125

Gln Val Tyr Thr Leu Pro Pro Ser Gln Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Ser Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys Ile Glu Gly Arg Met Asp Gln Val Ser His Arg
225                 230                 235                 240

Tyr Pro Arg Ile Gln Ser Ile Lys Val Gln Phe Thr Glu Tyr Lys Lys
                245                 250                 255

Glu Lys Gly Phe Ile Leu Thr Ser Gln Lys Glu Asp Glu Ile Met Lys
            260                 265                 270

Val Gln Asn Asn Ser Val Ile Ile Asn Cys Asp Gly Phe Tyr Leu Ile
        275                 280                 285

Ser Leu Lys Gly Tyr Phe Ser Gln Glu Val Asn Ile Ser Leu His Tyr
290                 295                 300

Gln Lys Asp Glu Glu Pro Leu Phe Gln Leu Lys Lys Val Arg Ser Val
305                 310                 315                 320

Asn Ser Leu Met Val Ala Ser Leu Thr Tyr Lys Asp Lys Val Tyr Leu
                325                 330                 335

Asn Val Thr Thr Asp Asn Thr Ser Leu Asp Asp Phe His Val Asn Gly
            340                 345                 350

Gly Glu Leu Ile Leu Ile His Gln Asn Pro Gly Glu Phe Cys Val Leu
        355                 360                 365
```

<210> SEQ ID NO 12

<211> LENGTH: 1588
<212> TYPE: DNA
<213> ORGANISM: Homo sapiens

<400> SEQUENCE: 12

```
tcccaagtag ctgggactac aggagcccac caccacccccc ggctaatttt ttgtatttttt    60
agtagagacg gggtttcacc gtgttagcca agatggtctt gatcacctga cctcgtgatc   120
cacccgcctt ggcctcccaa agtgctggga ttacaggcat gagccaccgc gcccggcctc   180
cattcaagtc tttattgaat atctgctatg ttctacacac tgttctaggt gctggggatg   240
caacagggga caaaataggc aaaatccctg tccttttggg gttgacattc tagtgactct   300
tcatgtagtc tagaagaagc tcagtgaata gtgtctgtgg ttgttaccag ggacacaatg   360
acaggaacat tcttgggtag agtgagaggc ctggggaggg aagggtctct aggatggagc   420
agatgctggg cagtcttagg gagcccctcc tggcatgcac cccctcatcc ctcaggccac   480
ccccgtccct gcaggagca ccctggggag ctgtccagag cgctgtgccg ctgtctgtgg   540
ctggaggcag agtaggtggt gtgctgggaa tgcgagtggg agaactggga tggaccgagg   600
ggaggcgggt gaggaggggg gcaaccaccc aacacccacc agctgctttc agtgttctgg   660
gtccaggtgc tcctggctgg ccttgtggtc cccctcctgc ttggggccac cctgacctac   720
acataccgcc actgctggcc tcacaagccc ctggttactg cagatgaagc tgggatggag   780
gctctgaccc caccaccggc cacccatctg tcacccttgg acagcgccca cacccttcta   840
gcacctcctg acagcagtga gaagatctgc accgtccagt tggtgggtaa cagctggacc   900
cctggctacc ccgagaccca ggaggcgctc tgcccgcagg tgacatggtc ctgggaccag   960
ttgcccagca gagctcttgg ccccgctgct gcgcccacac tctcgccaga gtccccagcc  1020
ggctcgccag ccatgatgct gcagccgggc ccgcagctct acgacgtgat ggacgcggtc  1080
ccagcgcggc gctggaagga gttcgtgcgc acgctggggc tgcgcgaggc agagatcgaa  1140
gccgtggagg tggagatcgg ccgcttccga gaccagcagt acgagatgct caagcgctgg  1200
cgccagcagc agcccgcggg cctcggagcc gtttacgcgg ccctggagcg catggggctg  1260
gacggctgcg tggaagactt gcgcagccgc ctgcagcgcg gccgtgaca cggcgcccac  1320
ttgccaccta ggcgctctgg tggcccttgc agaagcccta agtacggtta cttatgcgtg  1380
tagacatttt atgtcactta ttaagccgct ggcacggccc tgcgtagcag caccagccgg  1440
ccccaccccct gctcgccct atcgctccag ccaaggcgaa gaagcacgaa cgaatgtcga  1500
gagggggtga agacatttct caacttctcg gccggagttt ggctgagatc gcggtattaa  1560
atctgtgaaa gaaacaaaa caaaacaa                                       1588
```

<210> SEQ ID NO 13
<211> LENGTH: 426
<212> TYPE: PRT
<213> ORGANISM: Homo sapiens

<400> SEQUENCE: 13

```
Met Glu Gln Arg Pro Arg Gly Cys Ala Ala Val Ala Ala Ala Leu Leu
1               5                   10                  15

Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
        35                  40                  45

Arg Gly Cys Pro Ala Gly His Tyr Leu Lys Ala Pro Cys Thr Glu Pro
    50                  55                  60
```

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
        115                 120                 125

Gln Cys Val Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Pro Pro Ser Leu Ala Gly Ala Pro Trp Gly
            180                 185                 190

Ala Val Gln Ser Ala Val Pro Leu Ser Val Ala Gly Arg Val Gly
        195                 200                 205

Val Phe Trp Val Gln Val Leu Leu Ala Gly Leu Val Pro Leu Leu
210                 215                 220

Leu Gly Ala Thr Leu Thr Tyr Thr Tyr Arg His Cys Trp Pro His Lys
225                 230                 235                 240

Pro Leu Val Thr Ala Asp Glu Ala Gly Met Glu Ala Leu Thr Pro Pro
                245                 250                 255

Pro Ala Thr His Leu Ser Pro Leu Asp Ser Ala His Thr Leu Leu Ala
                260                 265                 270

Pro Pro Asp Ser Ser Glu Lys Ile Cys Thr Val Gln Leu Val Gly Asn
                275                 280                 285

Ser Trp Thr Pro Gly Tyr Pro Glu Thr Gln Glu Ala Leu Cys Pro Gln
    290                 295                 300

Val Thr Trp Ser Trp Asp Gln Leu Pro Ser Arg Ala Leu Gly Pro Ala
305                 310                 315                 320

Ala Ala Pro Thr Leu Ser Pro Glu Ser Pro Ala Gly Ser Pro Ala Met
                325                 330                 335

Met Leu Gln Pro Gly Pro Gln Leu Tyr Asp Val Met Asp Ala Val Pro
                340                 345                 350

Ala Arg Arg Trp Lys Glu Phe Val Arg Thr Leu Gly Leu Arg Glu Ala
        355                 360                 365

Glu Ile Glu Ala Val Glu Val Glu Ile Gly Arg Phe Arg Asp Gln Gln
        370                 375                 380

Tyr Glu Met Leu Lys Arg Trp Arg Gln Gln Pro Ala Gly Leu Gly
385                 390                 395                 400

Ala Val Tyr Ala Ala Leu Glu Arg Met Gly Leu Asp Gly Cys Val Glu
                405                 410                 415

Asp Leu Arg Ser Arg Leu Gln Arg Gly Pro
                420                 425

<210> SEQ ID NO 14
<211> LENGTH: 20
<212> TYPE: DNA
<213> ORGANISM: Artificial sequence
<220> FEATURE:
<223> OTHER INFORMATION: Synthetic sequence

<400> SEQUENCE: 14
ctgccacggc acagtcattg 20

<210> SEQ ID NO 15
<211> LENGTH: 20
<212> TYPE: DNA
<213> ORGANISM: Artificial sequence
<220> FEATURE:
<223> OTHER INFORMATION: Synthetic sequence

<400> SEQUENCE: 15
gccagttcct ccagatatcc 20

<210> SEQ ID NO 16
<211> LENGTH: 20
<212> TYPE: DNA
<213> ORGANISM: Artificial sequence
<220> FEATURE:
<223> OTHER INFORMATION: Synthetic sequence

<400> SEQUENCE: 16
ccacgctctt ctgtctactg 20

<210> SEQ ID NO 17
<211> LENGTH: 21
<212> TYPE: DNA
<213> ORGANISM: Artificial sequence
<220> FEATURE:
<223> OTHER INFORMATION: Synthetic sequence

<400> SEQUENCE: 17
gccatagaac tgatgagagg g 21

<210> SEQ ID NO 18
<211> LENGTH: 21
<212> TYPE: DNA
<213> ORGANISM: Artificial sequence
<220> FEATURE:
<223> OTHER INFORMATION: Synthetic sequence

<400> SEQUENCE: 18
ctactgctga ccttgtctct g 21

<210> SEQ ID NO 19
<211> LENGTH: 20
<212> TYPE: DNA
<213> ORGANISM: Artificial sequence
<220> FEATURE:
<223> OTHER INFORMATION: Synthetic sequence

<400> SEQUENCE: 19
agtaaggcca tgtagggtcg 20

<210> SEQ ID NO 20
<211> LENGTH: 24
<212> TYPE: DNA
<213> ORGANISM: Artificial sequence
<220> FEATURE:
<223> OTHER INFORMATION: Synthetic sequence

<400> SEQUENCE: 20
ctgcggcatg ttctggattt gact 24

<210> SEQ ID NO 21
<211> LENGTH: 24
<212> TYPE: DNA

<213> ORGANISM: Artificial sequence
<220> FEATURE:
<223> OTHER INFORMATION: Synthetic sequence

<400> SEQUENCE: 21
agtccaccac agttgctgac tcat                                              24

<210> SEQ ID NO 22
<211> LENGTH: 21
<212> TYPE: DNA
<213> ORGANISM: Artificial sequence
<220> FEATURE:
<223> OTHER INFORMATION: Synthetic sequence

<400> SEQUENCE: 22
gacacagtag agtgtcgcat g                                                 21

<210> SEQ ID NO 23
<211> LENGTH: 20
<212> TYPE: DNA
<213> ORGANISM: Artificial sequence
<220> FEATURE:
<223> OTHER INFORMATION: Synthetic sequence

<400> SEQUENCE: 23
aagcatgctc tgtggagctg                                                   20

<210> SEQ ID NO 24
<211> LENGTH: 20
<212> TYPE: DNA
<213> ORGANISM: Artificial sequence
<220> FEATURE:
<223> OTHER INFORMATION: Synthetic sequence

<400> SEQUENCE: 24
aaggccaacc gtgaaaagat                                                   20

<210> SEQ ID NO 25
<211> LENGTH: 21
<212> TYPE: DNA
<213> ORGANISM: Artificial sequence
<220> FEATURE:
<223> OTHER INFORMATION: Synthetic sequence

<400> SEQUENCE: 25
gtggtacgac cagaggcata c                                                 21

<210> SEQ ID NO 26
<211> LENGTH: 5
<212> TYPE: PRT
<213> ORGANISM: Artificial Sequence
<220> FEATURE:
<223> OTHER INFORMATION: Synthetic sequence

<400> SEQUENCE: 26

Gly Gly Gly Gly Ser
1               5

<210> SEQ ID NO 27
<211> LENGTH: 5
<212> TYPE: PRT
<213> ORGANISM: Artificial sequence
<220> FEATURE:
<223> OTHER INFORMATION: Synthetic sequence

<400> SEQUENCE: 27

Gly Gly Gly Gly Ser
1               5

<210> SEQ ID NO 28
<211> LENGTH: 8
<212> TYPE: PRT
<213> ORGANISM: Artificial sequence
<220> FEATURE:
<223> OTHER INFORMATION: Synthetic sequence

<400> SEQUENCE: 28

Gly Gly Gly Gly Gly Gly Gly Gly
1               5

<210> SEQ ID NO 29
<211> LENGTH: 6
<212> TYPE: PRT
<213> ORGANISM: Artificial sequence
<220> FEATURE:
<223> OTHER INFORMATION: Synthetic sequence

<400> SEQUENCE: 29

Gly Gly Gly Gly Gly Gly
1               5

<210> SEQ ID NO 30
<211> LENGTH: 5
<212> TYPE: PRT
<213> ORGANISM: Artificial sequence
<220> FEATURE:
<223> OTHER INFORMATION: Synthetic sequence

<400> SEQUENCE: 30

Glu Ala Ala Ala Lys
1               5

<210> SEQ ID NO 31
<211> LENGTH: 7
<212> TYPE: PRT
<213> ORGANISM: Artificial sequence
<220> FEATURE:
<223> OTHER INFORMATION: Synthetic sequence

<400> SEQUENCE: 31

Ala Glu Ala Ala Ala Lys Ala
1               5

<210> SEQ ID NO 32
<211> LENGTH: 12
<212> TYPE: PRT
<213> ORGANISM: Artificial sequence
<220> FEATURE:
<223> OTHER INFORMATION: Synthetic sequence

<400> SEQUENCE: 32

Ala Glu Ala Ala Ala Lys Glu Ala Ala Ala Lys Ala
1               5                   10

<210> SEQ ID NO 33
<211> LENGTH: 46
<212> TYPE: PRT
<213> ORGANISM: Artificial sequence
<220> FEATURE:
<223> OTHER INFORMATION: Synthetic sequence

<400> SEQUENCE: 33

Ala Glu Ala Ala Ala Lys Glu Ala Ala Ala Lys Glu Ala Ala Ala Lys

```
                1               5                   10                  15
Glu Ala Ala Ala Lys Ala Leu Glu Ala Glu Ala Ala Lys Glu Ala
                20                  25                  30
Ala Ala Lys Glu Ala Ala Ala Lys Glu Ala Ala Ala Lys Ala
                35                  40                  45
```

<210> SEQ ID NO 34
<211> LENGTH: 5
<212> TYPE: PRT
<213> ORGANISM: Artificial sequence
<220> FEATURE:
<223> OTHER INFORMATION: Synthetic sequence

<400> SEQUENCE: 34

```
Pro Ala Pro Ala Pro
1               5
```

<210> SEQ ID NO 35
<211> LENGTH: 18
<212> TYPE: PRT
<213> ORGANISM: Artificial sequence
<220> FEATURE:
<223> OTHER INFORMATION: Synthetic sequence

<400> SEQUENCE: 35

```
Lys Glu Ser Gly Ser Val Ser Ser Glu Gln Leu Ala Gln Phe Arg Ser
1               5                   10                  15

Leu Asp
```

<210> SEQ ID NO 36
<211> LENGTH: 14
<212> TYPE: PRT
<213> ORGANISM: Artificial sequence
<220> FEATURE:
<223> OTHER INFORMATION: Synthetic sequence

<400> SEQUENCE: 36

```
Glu Gly Lys Ser Ser Gly Ser Gly Ser Glu Ser Lys Ser Thr
1               5                   10
```

<210> SEQ ID NO 37
<211> LENGTH: 12
<212> TYPE: PRT
<213> ORGANISM: Artificial sequence
<220> FEATURE:
<223> OTHER INFORMATION: Synthetic sequence

<400> SEQUENCE: 37

```
Gly Ser Ala Gly Ser Ala Ala Gly Ser Gly Glu Phe
1               5                   10
```

<210> SEQ ID NO 38
<211> LENGTH: 852
<212> TYPE: DNA
<213> ORGANISM: Homo sapiens

<400> SEQUENCE: 38

```
atggagcctc ctggagactg ggggcctcct ccctggagat ccaccccaa aaccgacgtc      60 ttgaggctgg tgctgtatct caccttcctg ggagccccct gctacgcccc agctctgccg     120
tcctgcaagg aggacgagta cccagtgggc tccgagtgct gccccaagtg cagtccaggt     180
tatcgtgtga aggaggcctg cggggagctg acgggcacag tgtgtgaacc ctgccctcca     240
ggcacctaca ttgcccacct caatggccta agcaagtgtc tgcagtgcca aatgtgtgac     300
```

```
ccagccatgg gcctgcgcgc gagccggaac tgctccagga cagagaacgc cgtgtgtggc      360
tgcagcccag gccacttctg catcgtccag gacggggacc actgcgccgc gtgccgcgct      420
tacgccacct ccagcccggg ccagagggtg cagaagggag gcaccgagag tcaggacacc      480
ctgtgtcaga actgccccc ggggaccttc tctcccaatg ggaccctgga ggaatgtcag       540
```

```
ccagccatgg gcctgcgcgc gagccggaac tgctccagga cagagaacgc cgtgtgtggc      360
tgcagcccag gccacttctg catcgtccag gacggggacc actgcgccgc gtgccgcgct      420
tacgccacct ccagcccggg ccagagggtg cagaagggag gcaccgagag tcaggacacc      480
ctgtgtcaga actgccccc ggggaccttc tctcccaatg ggaccctgga ggaatgtcag       540
caccagacca agtgcagctg gctggtgacg aaggccggag ctgggaccag cagctcccac      600
tgggtatggt ggtttctctc agggagcctc gtcatcgtca ttgtttgctc acagttggc       660 ctaatcatat gtgtgaaaag aagaaagcca aggggtgatg tagtcaaggt gatcgtctcc      720
gtccagcgga aaagacagga ggcagaaggt gaggccacag tcattgaggc cctgcaggcc      780
cctccggacg tcaccacggt ggccgtggag gagacaatac cctcattcac ggggaggagc      840
ccaaaccatt aa                                                         852
```

<210> SEQ ID NO 39
<211> LENGTH: 283
<212> TYPE: PRT
<213> ORGANISM: Homo sapiens

<400> SEQUENCE: 39

```
Met Glu Pro Pro Gly Asp Trp Gly Pro Pro Trp Arg Ser Thr Pro
1               5                   10                  15

Lys Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Trp Trp Phe Leu Ser Gly
        195                 200                 205

Ser Leu Val Ile Val Ile Val Cys Ser Thr Val Gly Leu Ile Ile Cys
    210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
            260                 265                 270
```

Ile Pro Ser Phe Thr Gly Arg Ser Pro Asn His
        275                 280

<210> SEQ ID NO 40
<211> LENGTH: 4900
<212> TYPE: DNA
<213> ORGANISM: Homo sapiens

<400> SEQUENCE: 40

| | | | | | |
|---|---|---|---|---|---|
| taaagtcatc | aaaacaacgt | tatatcctgt | gtgaaatgct | gcagtcagga | tgccttgtgg | 60 |
| tttgagtgcc | ttgatcatgt | gccctaaggg | gatggtggcg | gtggtggtgg | ccgtggatga | 120 |
| cggagactct | caggccttgg | caggtgcgtc | tttcagttcc | cctcacactt | cgggttcctc | 180 |
| ggggaggagg | ggctggaacc | ctagcccatc | gtcaggacaa | agatgctcag | gctgctcttg | 240 |
| gctctcaact | tattcccttc | aattcaagta | acaggaaaca | agattttggt | gaagcagtcg | 300 |
| cccatgcttg | tagcgtacga | caatgcggtc | aaccttagct | gcaagtattc | ctacaatctc | 360 |
| ttctcaaggg | agttccgggc | atcccttcac | aaaggactgg | atagtgctgt | ggaagtctgt | 420 |
| gttgtatatg | ggaattactc | ccagcagctt | caggtttact | caaaaacggg | gttcaactgt | 480 |
| gatgggaaat | tgggcaatga | atcagtgaca | ttctacctcc | agaatttgta | tgttaaccaa | 540 |
| acagatattt | acttctgcaa | aattgaagtt | atgtatcctc | ctccttacct | agacaatgag | 600 |
| aagagcaatg | gaaccattat | ccatgtgaaa | gggaaacacc | tttgtccaag | tccctatttt | 660 |
| cccggacctt | ctaagccctt | tgggtgctg | gtggtggttg | gtggagtcct | ggcttgctat | 720 |
| agcttgctag | taacagtggc | ctttattatt | ttctgggtga | ggagtaagag | gagcaggctc | 780 |
| ctgcacagtg | actacatgaa | catgactccc | cgccgccccg | ggcccacccg | caagcattac | 840 |
| cagcccctatg | ccccaccacg | cgacttcgca | gcctatcgct | cctgacacgg | acgcctatcc | 900 |
| agaagccagc | cggctggcag | ccccatctg | ctcaatatca | ctgctctgga | taggaaatga | 960 |
| ccgccatctc | cagccggcca | cctcaggccc | ctgttgggcc | accaatgcca | attttctcg | 1020 |
| agtgactaga | ccaaatatca | agatcatttt | gagactctga | atgaagtaa | aagagatttc | 1080 |
| ctgtgacagc | ccaagtctta | cagtgccatg | gcccacattc | caacttacca | tgtacttagt | 1140 |
| gacttgactg | agaagttagg | gtagaaaaca | aaaagggagt | ggattctggg | agcctcttcc | 1200 |
| ctttctcact | cacctgcaca | tctcagtcaa | gcaaagtgtg | gtatccacag | acattttagt | 1260 |
| tgcagaagaa | aggctaggaa | atcattcctt | ttggttaaat | gggtgtttaa | tcttttggtt | 1320 |
| agtgggttaa | acggggtaag | ttagagtagg | gggagggata | ggaagacata | tttaaaaacc | 1380 |
| attaaaacac | tgtctcccac | tcatgaaatg | agccacgtag | ttcctattta | atgctgtttt | 1440 |
| cctttagttt | agaaatacat | agacattgtc | ttttatgaat | tctgatcata | tttagtcatt | 1500 |
| ttgaccaaat | gagggatttg | gtcaaatgag | ggattccctc | aaagcaatat | caggtaaacc | 1560 |
| aagttgcttt | cctcactccc | tgtcatgaga | cttcagtgtt | aatgttcaca | atatactttc | 1620 |
| gaaagaataa | aatagttctc | ctacatgaag | aaagaatatg | tcaggaaata | aggtcacttt | 1680 |
| atgtcaaaat | tatttgagta | ctatgggacc | tggcgcagtg | gctcatgctt | gtaatcccag | 1740 |
| cactttggga | ggccgaggtg | ggcagatcac | ttgagatcag | gaccagcctg | gtcaagatgg | 1800 |
| tgaaactccg | tctgtactaa | aaatacaaaa | tttagcttgg | cctggtggca | ggcacctgta | 1860 |
| atcccagctg | cccaagaggc | tgaggcatga | gaatcgcttg | aacctggcag | gcggaggttg | 1920 |
| cagtgagccg | agatagtgcc | acagctctcc | agcctgggcg | acagagtgag | actccatctc | 1980 |
| aaacaacaac | aacaacaaca | acaacaacaa | caaaccacaa | aattatttga | gtactgtgaa | 2040 |

```
ggattatttg tctaacagtt cattccaatc agaccaggta ggagctttcc tgtttcatat    2100
gtttcagggt tgcacagttg gtctctttaa tgtcggtgtg gagatccaaa gtgggttgtg    2160
gaaagagcgt ccataggaga agtgagaata ctgtgaaaaa gggatgttag cattcattag    2220
agtatgagga tgagtcccaa gaaggttctt tggaaggagg acgaatagaa tggagtaatg    2280
aaattcttgc catgtgctga ggagatagcc agcattaggt gacaatcttc cagaagtggt    2340
caggcagaag gtgccctggt gagagctcct ttacagggac tttatgtggt ttagggctca    2400
gagctccaaa actctgggct cagctgctcc tgtaccttgg aggtccattc acatgggaaa    2460
gtattttgga atgtgtcttt tgaagagagc atcagagttc ttaagggact gggtaaggcc    2520
tgaccctgaa atgaccatgg atattttctc acctacagtt tgagtcaact agaatatgcc    2580
tggggacctt gaagaatggc ccttcagtgg ccctcaccat tgttcatgc ttcagttaat     2640 tcaggtgttg aaggagctta ggttttagag gcacgtagac ttggttcaag tctcgttagt    2700
agttgaatag cctcaggcaa gtcactgccc acctaagatg atggttcttc aactataaaa    2760
tggagataat ggttacaaat gtctcttcct atagtataat ctccataagg gcatggccca    2820
agtctgtctt tgactctgcc tatccctgac atttagtagc atgcccgaca tacaatgtta    2880
gctattggta ttattgccat atagataaat tatgtataaa aattaaactg gcaatagcc     2940 taagaagggg ggaatattgt aacacaaatt taaacccact acgcagggat gaggtgctat    3000
aatatgagga ccttttaact tccatcattt tcctgtttct tgaaatagtt tatcttgtaa    3060
tgaaatataa ggcacctccc acttttatgt atagaaagag gtcttttaat ttttttttaa    3120
tgtgagaagg aagggaggag taggaatctt gagattccag atcgaaaata ctgtactttg    3180
gttgattttt aagtgggctt ccattccatg gatttaatca gtcccaagaa gatcaaactc    3240
agcagtactt gggtgctgaa gaactgttgg atttaccctg gcacgtgtgc cacttgccag    3300
cttcttgggc acacagagtt cttcaatcca agttatcaga ttgtatttga aaatgacaga    3360
gctggagagt ttttttgaaat ggcagtggca ataaataaa tactttttt taaatggaaa     3420 gacttgatct atggtaataa atgattttgt tttctgactg gaaaaatagg cctactaaag    3480
atgaatcaca cttgagatgt ttcttactca ctctgcacag aaacaaagaa gaaatgttat    3540
acagggaagt ccgttttcac tattagtatg aaccaagaaa tggttcaaaa acagtggtag    3600
gagcaatgct ttcatagttt cagatatggt agttatgaag aaaacaatgt catttgctgc    3660
tattattgta agagtcttat aattaatggt actcctataa ttttgattg tgagctcacc      3720 tatttgggtt aagcatgcca atttaaagag accaagtgta tgtacattat gttctacata    3780
ttcagtgata aaattactaa actactatat gtctgcttta aatttgtact ttaatattgt    3840
cttttggtat taagaaagat atgctttcag aatagatatg cttcgctttg gcaaggaatt    3900
tggatagaac ttgctattta aaagaggtgt ggggtaaatc cttgtataaa tctccagttt    3960
agcctttttt gaaaaagcta gactttcaaa tactaatttc acttcaagca gggtacgttt    4020
ctggtttgtt tgcttgactt cagtcacaat ttcttatcag accaatggct gacctctttg    4080
agatgtcagg ctaggcttac ctatgtgttc tgtgtcatgt gaatgctgag aagtttgaca    4140
gagatccaac ttcagccttg accccatcag tccctcgggt taactaactg agccaccggt    4200
cctcatggct attttaatga gggtattgat ggttaaatgc atgtctgatc ccttatccca    4260
gccatttgca ctgccagctg ggaactatac cagacctgga tactgatccc aaagtgttaa    4320
attcaactac atgctggaga ttagagatgg tgccaataaa ggacccagaa ccaggatctt    4380
```

```
gattgctata gacttattaa taatccaggt caaagagagt gacacacact ctctcaagac      4440
ctggggtgag ggagtctgtg ttatctgcaa ggccatttga ggctcagaaa gtctctcttt      4500
cctatagata tatgcatact ttctgacata taggaatgta tcaggaatac tcaaccatca      4560
caggcatgtt cctacctcag ggcctttaca tgtcctgttt actctgtcta gaatgtcctt      4620
ctgtagatga cctggcttgc ctcgtcaccc ttcaggtcct tgctcaagtg tcatcttctc      4680
ccctagttaa actaccccac accctgtctg ctttccttgc ttattttcct ccatagcatt      4740
ttaccatctc ttacattaga cattttctt atttatttgt agtttataag cttcatgagg       4800
caagtaactt tgctttgttt cttgctgtat ctccagtgcc cagagcagtg cctggtatat      4860
aataaatatt tattgactga gtgaaaaaaa aaaaaaaaa                             4900
```

<210> SEQ ID NO 41
<211> LENGTH: 220
<212> TYPE: PRT
<213> ORGANISM: Homo sapiens

<400> SEQUENCE: 41

```
Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220
```

<210> SEQ ID NO 42
<211> LENGTH: 1906
<212> TYPE: DNA
<213> ORGANISM: Homo sapiens

<400> SEQUENCE: 42

```
ccaagtcaca tgattcagga ttcagggga gaatccttct tggaacagag atgggcccag        60
aactgaatca gatgaagaga gataaggtgt gatgtgggga agactatata aagaatggac      120
```

```
ccagggctgc agcaagcact caacggaatg gcccctcctg agacacagc catgcatgtg      180 ccggcgggct ccgtggccag ccacctgggg accacgagcc gcagctattt ctatttgacc      240
acagccactc tggctctgtg ccttgtcttc acggtggcca ctattatggt gttggtcgtt      300
cagaggacgg actccattcc caactcacct gacaacgtcc ccctcaaagg aggaaattgc      360
tcagaagacc tcttatgtat cctgaaaaga gctccattca agaagtcatg gcctacctc       420 caagtggcaa agcatctaaa caaaaccaag ttgtcttgga acaaagatgg cattctccat      480
ggagtcagat atcaggatgg gaatctggtg atccaattcc ctggtttgta cttcatcatt      540
tgccaactgc agtttcttgt acaatgccca ataattctg tcgatctgaa gttggagctt       600
ctcatcaaca agcatatcaa aaacaggcc ctggtgacag tgtgtgagtc tggaatgcaa       660
acgaaacacg tataccagaa tctctctcaa ttcttgctgg attacctgca ggtcaacacc      720
accatatcag tcaatgtgga tacattccag tacatagata caagcacctt tcctcttgag      780
aatgtgttgt ccatcttctt atacagtaat tcagactgaa cagtttctct tggccttcag      840
gaagaaagcg cctctctacc atacagtatt tcatccctcc aaacacttgg gcaaaaagaa      900
aactttagac caagacaaac tacacagggt attaaatagt atacttctcc ttctgtctct      960
tggaaagata cagctccagg gttaaaaaga gagttttttag tgaagtatct ttcagatagc    1020
aggcagggaa gcaatgtagt gtggtgggca gagccccaca cagaatcaga agggatgaat    1080
ggatgtccca gcccaaccac taattcactg tatggtcttg atctatttct tctgttttga    1140
gagcctccag ttaaaatggg gcttcagtac cagagcagct agcaactctg ccctaatggg    1200
aaatgaaggg gagctgggtg tgagtgttta cactgtgccc ttcacgggat acttctttta    1260
tctgcagatg gcctaatgct tagttgtcca agtcgcgatc aaggactctc tcacacagga    1320
aacttcccta tactggcaga tacacttgtg actgaaccat gcccagttta tgcctgtctg    1380
actgtcactc tggcactagg aggctgatct tgtactccat atgaccccac ccctaggaac    1440
ccccagggaa aaccaggctc ggacagcccc ctgttcctga gatggaaagc acaaatttaa    1500
tacaccacca caatggaaaa caagttcaaa gacttttact tacagatcct ggacagaaag    1560
ggcataatga gtctgaaggg cagtcctcct tctccaggtt acatgaggca ggaataagaa    1620
gtcagacaga gacagcaaga cagttaacaa cgtaggtaaa gaaatagggt gtggtcactc    1680
tcaattcact ggcaaatgcc tgaatggtct gtctgaagga agcaacagag aagtggggaa    1740
tccagtctgc taggcaggaa agatgcctct aagttcttgt ctctggccag aggtgtggta    1800
tagaaccaga aacccatatc aagggtgact aagcccggct tccggtatga gaaattaaac    1860
ttgtatacaa aatggttgcc aaggcaacat aaaattataa gaattc                     1906
```

<210> SEQ ID NO 43
<211> LENGTH: 234
<212> TYPE: PRT
<213> ORGANISM: Homo sapiens

<400> SEQUENCE: 43

```
Met Asp Pro Gly Leu Gln Gln Ala Leu Asn Gly Met Ala Pro Pro Gly
1               5                   10                  15

Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
        35                  40                  45

Cys Leu Val Phe Thr Val Ala Thr Ile Met Val Leu Val Val Gln Arg
```

```
                50                  55                  60
Thr Asp Ser Ile Pro Asn Ser Pro Asp Asn Val Pro Leu Lys Gly Gly
 65                  70                  75                  80

Asn Cys Ser Glu Asp Leu Leu Cys Ile Leu Lys Arg Ala Pro Phe Lys
                 85                  90                  95

Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
        115                 120                 125

Gly Asn Leu Val Ile Gln Phe Pro Gly Leu Tyr Phe Ile Ile Cys Gln
    130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
        195                 200                 205

Asp Thr Phe Gln Tyr Ile Asp Thr Ser Thr Phe Pro Leu Glu Asn Val
    210                 215                 220

Leu Ser Ile Phe Leu Tyr Ser Asn Ser Asp
225                 230

<210> SEQ ID NO 44
<211> LENGTH: 1629
<212> TYPE: DNA
<213> ORGANISM: Homo sapiens

<400> SEQUENCE: 44
tttcctgggc ggggccaagg ctggggcagg ggagtcagca gaggcctcgc tcgggcgccc      60
agtggtcctg ccgcctggtc tcacctcgct atggttcgtc tgcctctgca gtgcgtcctc     120
tggggctgct tgctgaccgc tgtccatcca gaaccaccca ctgcatgcag agaaaaacag     180
tacctaataa acagtcagtg ctgttctttg tgccagccag acagaaaact ggtgagtgac     240
tgcacagagt tcactgaaac ggaatgcctt ccttgcggtg aaagcgaatt cctagacacc     300
tggaacagag agacacactg ccaccagcac aaatactgcg accccaacct agggcttcgg     360
gtccagcaga agggcacctc agaaacagac accatctgca cctgtgaaga aggctggcac     420
tgtacgagtg aggcctgtga gagctgtgtc ctgaccgct catgctcgcc cggctttggg     480
gtcaagcaga ttgctacagg ggtttctgat accatctgcg agccctgccc agtcggcttc     540
ttctccaatg tgtcatctgc tttcgaaaaa tgtcacccct tggacaagctg tgagaccaaa     600
gacctggttg tgcaacaggc aggcacaaac aagactgatg ttgtctgtgg tccccaggat     660
cggctgagag ccctggtggt gatccccatc atcttcggga tcctgtttgc catcctcttg     720
gtgctggtct ttatcaaaaa ggtggccaag aagccaacca taaggccccc cacccccaag     780
caggaacccc aggagatcaa ttttcccgac gatcttcctg ctccaacac tgctgctcca     840
gtgcaggaga ctttacatgg atgccaaccg gtcacccagg aggatggcaa agagagtcgc     900
atctcagtgc aggagagaca gtgaggctgc acccacccag gagtgtggcc acgtgggcaa     960
acaggcagtt ggccagagag cctggtgctg ctgctgctgt ggcgtgaggg tgaggggctg    1020
gcactgactg ggcatagctc cccgcttctg cctgcacccc tgcagtttga gacaggagac    1080
```

```
ctggcactgg atgcagaaac agttcacctt gaagaacctc tcacttcacc ctggagccca    1140
tccagtctcc caacttgtat taaagacaga ggcagaagtt tggtggtggt ggtgttgggg    1200
tatggtttag taatatccac cagaccttcc gatccagcag tttggtgccc agagaggcat    1260
catggtggct tccctgcgcc caggaagcca tatacacaga tgcccattgc agcattgttt    1320
gtgatagtga caactggaa gctgcttaac tgtccatcag caggagactg gctaaataaa    1380
attagaatat atttatacaa cagaatctca aaaacactgt tgagtaagga aaaaaggca    1440 tgctgctgaa tgatgggtat ggaactttt aaaaaagtac atgcttttat gtatgtatat    1500
tgcctatgga tatatgtata aatacaatat gcatcatata ttgatataac aagggttctg    1560
gaagggtaca cagaaaaccc acagctcgaa gagtggtgac gtctggggtg gggaagaagg    1620
gtctggggg                                                             1629
```

```
<210> SEQ ID NO 45
<211> LENGTH: 277
<212> TYPE: PRT
<213> ORGANISM: Homo sapiens

<400> SEQUENCE: 45
```

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
          275

<210> SEQ ID NO 46
<211> LENGTH: 913
<212> TYPE: DNA
<213> ORGANISM: Homo sapiens

<400> SEQUENCE: 46

| | | | | | |
|---|---|---|---|---|---|
| ccagagaggg | gcaggctggt | ccctgacag | gttgaagcaa | gtagacgccc | aggagccccg | 60 |
| ggagggggct | gcagtttcct | tccttccttc | tcggcagcgc | tccgcgcccc | catcgcccct | 120 |
| cctgcgctag | cggaggtgat | cgccgcggcg | atgccgagg | agggttcggg | ctgctcggtg | 180 |
| cggcgcaggc | cctatgggtg | cgtcctgcgg | gctgctttgg | tcccattggt | cgcgggcttg | 240 |
| gtgatctgcc | tcgtggtgtg | catccagcgc | ttcgcacagg | ctcagcagca | gctgccgctc | 300 |
| gagtcacttg | ggtgggacgt | agctgagctg | cagctgaatc | acacaggacc | tcagcaggac | 360 |
| cccaggctat | actggcaggg | gggcccagca | ctgggccgct | ccttcctgca | tggaccagag | 420 |
| ctggacaagg | ggcagctacg | tatccatcgt | gatggcatct | acatggtaca | catccaggtg | 480 |
| acgctggcca | tctgctcctc | cacgacggcc | tccaggcacc | accccaccac | cctgccgtg | 540 |
| ggaatctgct | ctcccgcctc | ccgtagcatc | agcctgctgc | gtctcagctt | ccaccaaggt | 600 |
| tgtaccattg | cctcccagcg | cctgacgccc | tggcccgag | ggacacact | ctgcaccaac | 660 |
| ctcactggga | cactttgcc | ttcccgaaac | actgatgaga | ccttctttgg | agtgcagtgg | 720 |
| gtgcgcccct | gaccactgct | gctgattagg | gttttttaaa | ttttattta | ttttatttaa | 780 |
| gttcaagaga | aaaagtgtac | acacaggggc | caccgggt | tggggtggga | gtgtggtggg | 840 |
| gggtagtggt | ggcaggacaa | gagaaggcat | tgagcttttt | ctttcattt | cctattaaaa | 900 |
| aatacaaaaa | tca | | | | | 913 |

<210> SEQ ID NO 47
<211> LENGTH: 193
<212> TYPE: PRT
<213> ORGANISM: Homo sapiens

<400> SEQUENCE: 47

Met Pro Glu Glu Gly Ser Gly Cys Ser Val Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
            85                  90                  95

Arg Ile His Arg Asp Gly Ile Tyr Met Val His Ile Gln Val Thr Leu
        100                 105                 110

Ala Ile Cys Ser Ser Thr Thr Ala Ser Arg His His Pro Thr Thr Leu
    115                 120                 125

Ala Val Gly Ile Cys Ser Pro Ala Ser Arg Ser Ile Ser Leu Leu Arg
        130                 135                 140

Leu Ser Phe His Gln Gly Cys Thr Ile Ala Ser Gln Arg Leu Thr Pro

```
                145                 150                 155                 160
Leu Ala Arg Gly Asp Thr Leu Cys Thr Asn Leu Thr Gly Thr Leu Leu
                    165                 170                 175

Pro Ser Arg Asn Thr Asp Glu Thr Phe Phe Gly Val Gln Trp Val Arg
                    180                 185                 190

Pro

<210> SEQ ID NO 48
<211> LENGTH: 723
<212> TYPE: DNA
<213> ORGANISM: Homo sapiens

<400> SEQUENCE: 48
atggaggaga gtgtcgtacg gccctcagtg tttgtggtgg atggacagac cgacatccca     60
ttcacgaggc tgggacgaag ccaccggaga cagtcgtgca gtgtggcccg ggtgggtctg    120
ggtctcttgc tgttgctgat gggggccggg ctggccgtcc aaggctggtt cctcctgcag    180
ctgcactggc gtctaggaga gatggtcacc cgcctgcctg acggacctgc aggctcctgg    240
gagcagctga tacaagagcg aaggtctcac gaggtcaacc cagcagcgca tctcacaggg    300
gccaactcca gcttgaccgg cagcgggggg ccgctgttat gggagactca gctgggcctg    360
gccttcctga ggggcctcag ctaccacgat ggggcccttg tggtcaccaa agctggctac    420
tactacatct actccaaggt gcagctgggc ggtgtgggct gccgctgggc cctggccagc    480
accatcaccc acggcctcta caagcgcaca ccccgctacc ccgaggagct ggagctgttg    540
gtcagccagc agtcaccctg cggacgggcc accagcagct cccgggtctg gtgggacagc    600
agcttcctgg gtggtgtggt acacctggag gctggggagg aggtggtcgt ccgtgtgctg    660
gatgaacgcc tggttcgact gcgtgatggt acccggtctt acttcggggc tttcatggtg    720
tga                                                                  723

<210> SEQ ID NO 49
<211> LENGTH: 240
<212> TYPE: PRT
<213> ORGANISM: Homo sapiens

<400> SEQUENCE: 49

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
                20                  25                  30

Cys Ser Val Ala Arg Val Gly Leu Gly Leu Leu Leu Leu Leu Met Gly
                35                  40                  45

Ala Gly Leu Ala Val Gln Gly Trp Phe Leu Leu Gln Leu His Trp Arg
        50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
                100                 105                 110

Leu Trp Glu Thr Gln Leu Gly Leu Ala Phe Leu Arg Gly Leu Ser Tyr
            115                 120                 125

His Asp Gly Ala Leu Val Val Thr Lys Ala Gly Tyr Tyr Tyr Ile Tyr
        130                 135                 140
```

-continued

```
Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Glu Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240
```